(12) United States Patent
Eggers et al.

(10) Patent No.: US 6,923,804 B2
(45) Date of Patent: Aug. 2, 2005

(54) ELECTROSURGICAL GENERATOR

(75) Inventors: Philip E. Eggers, Dublin, OH (US);
John Kociecki, Powell, OH (US);
Mark A. Mayerchak, Bothell, WA (US)

(73) Assignee: Neothermia Corporation, Natick, MA (US)

( * ) Notice: Subject to any disclaimer, the term of this patent is extended or adjusted under 35 U.S.C. 154(b) by 109 days.

(21) Appl. No.: 10/633,031

(22) Filed: Aug. 1, 2003

(65) Prior Publication Data

US 2004/0030328 A1 Feb. 12, 2004

Related U.S. Application Data

(63) Continuation-in-part of application No. 09/904,412, filed on Jul. 12, 2001, now Pat. No. 6,740,079.

(51) Int. Cl.[7] .............................................. A61B 18/12
(52) U.S. Cl. .......................................... 606/34; 606/39
(58) Field of Search ............................... 606/34, 37–40

(56) References Cited

U.S. PATENT DOCUMENTS 3,952,748 A * 4/1976 Kaliher et al. ................ 606/37
5,647,869 A * 7/1997 Goble et al. .................. 606/37
6,277,114 B1 * 8/2001 Bullivant et al. ............. 606/41
6,416,509 B1 * 7/2002 Goble et al. .................. 606/37

FOREIGN PATENT DOCUMENTS

EP          0754437       *  1/1997

* cited by examiner

*Primary Examiner*—Lee S. Cohen
(74) *Attorney, Agent, or Firm*—Mueller and Smith, LPA

(57) ABSTRACT

An electrosurgical generator which provides a constant power output particularly suited for cutting arc formation at an active electrode which exhibits a dynamic active surface area of varying geometry. Essentially constant power-based control is achieved through the utilization of a d.c. link voltage the level of which functions to establish the amplitude of the output of an RF resonant inverter. A dual loop feedback control is described wherein output power based control signals are slowly introduced at low gain, while link voltage based controls are comparatively rapidly applied. Enhanced development of a controlling d.c. link voltage is achieved through the utilization of an input network incorporating a power factor correction stage.

64 Claims, 38 Drawing Sheets

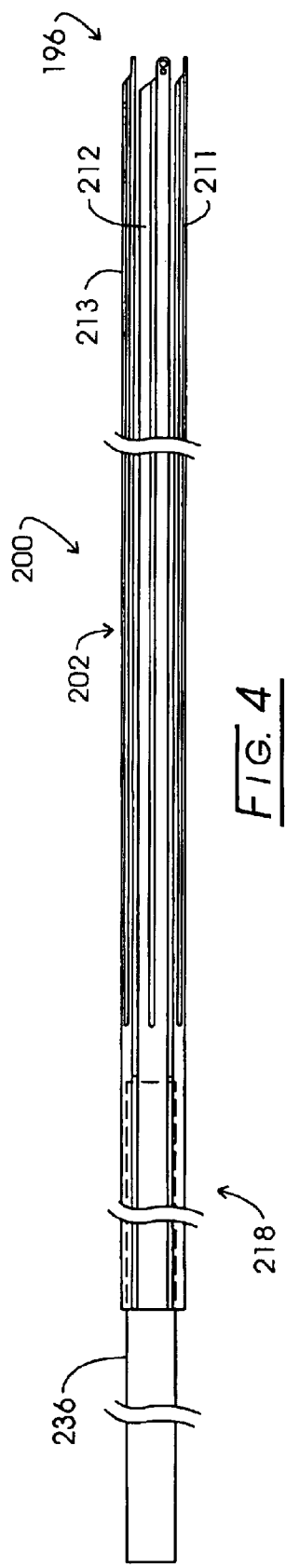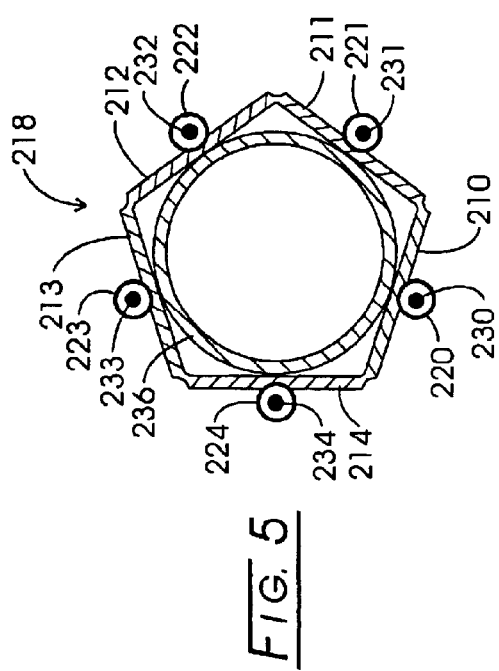

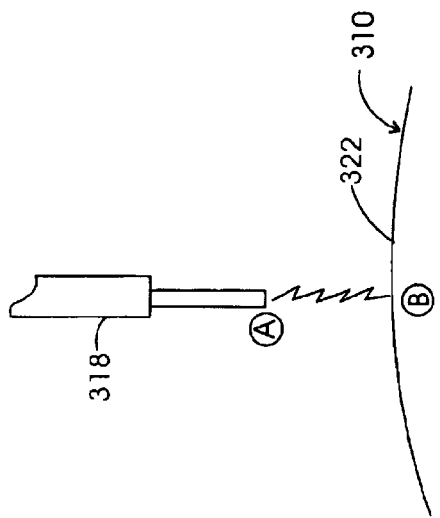
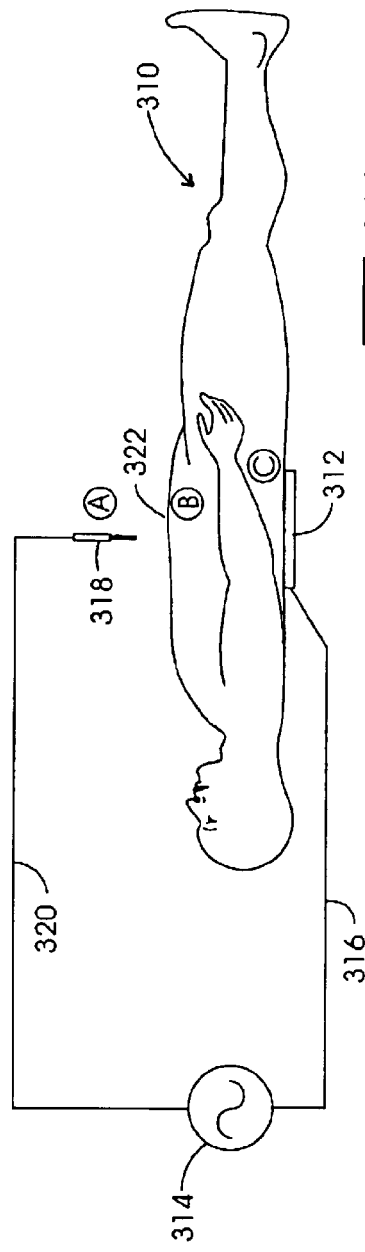
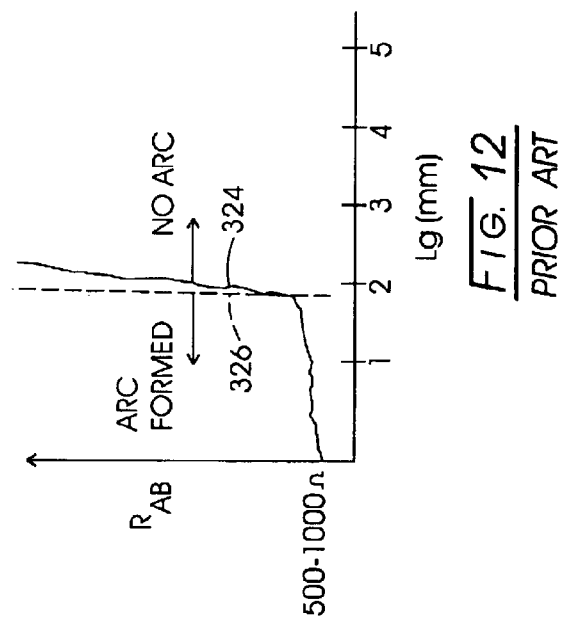
FIG. 11B
PRIOR ART
FIG. 11A
PRIOR ART
FIG. 12
PRIOR ART

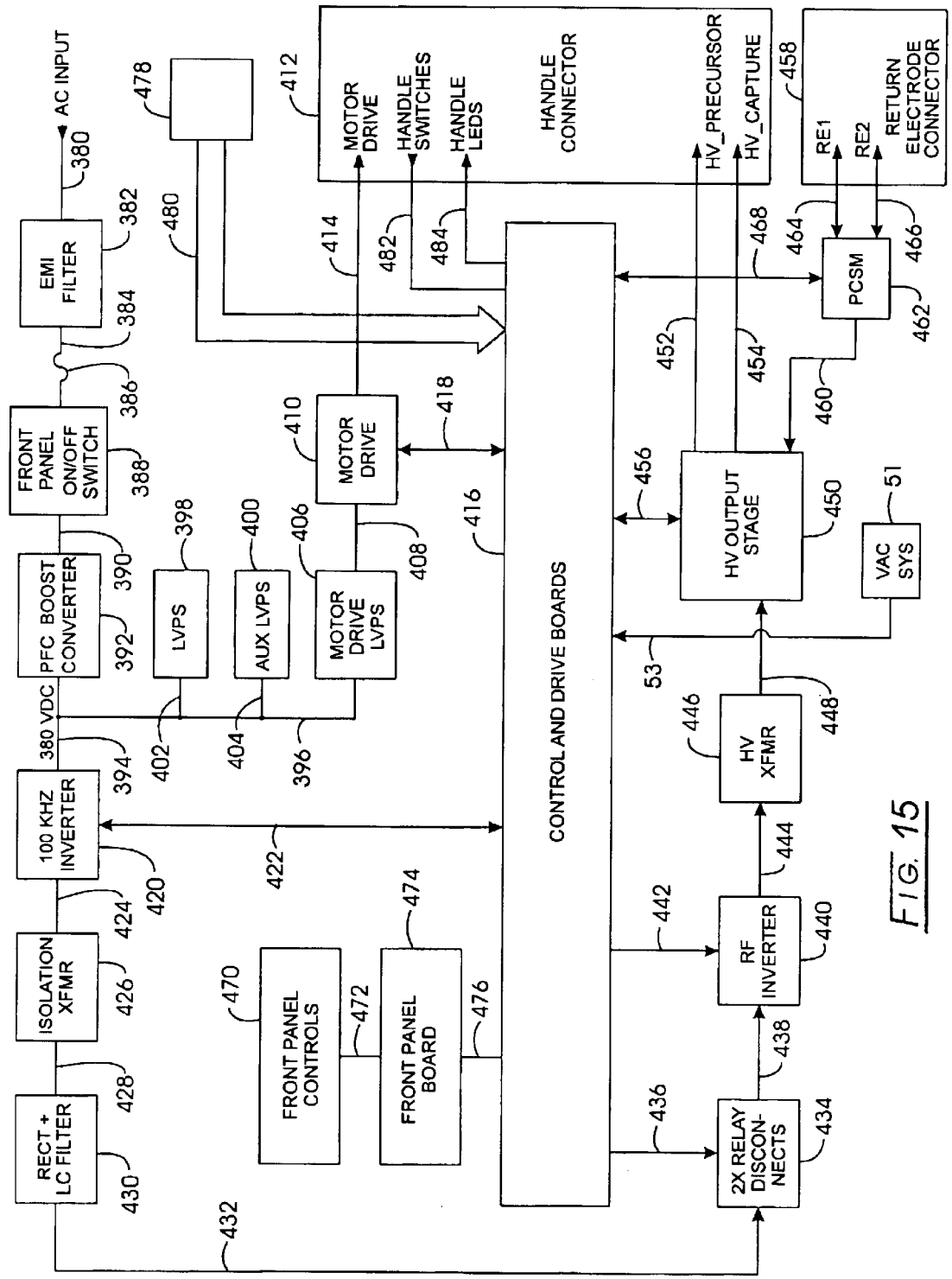

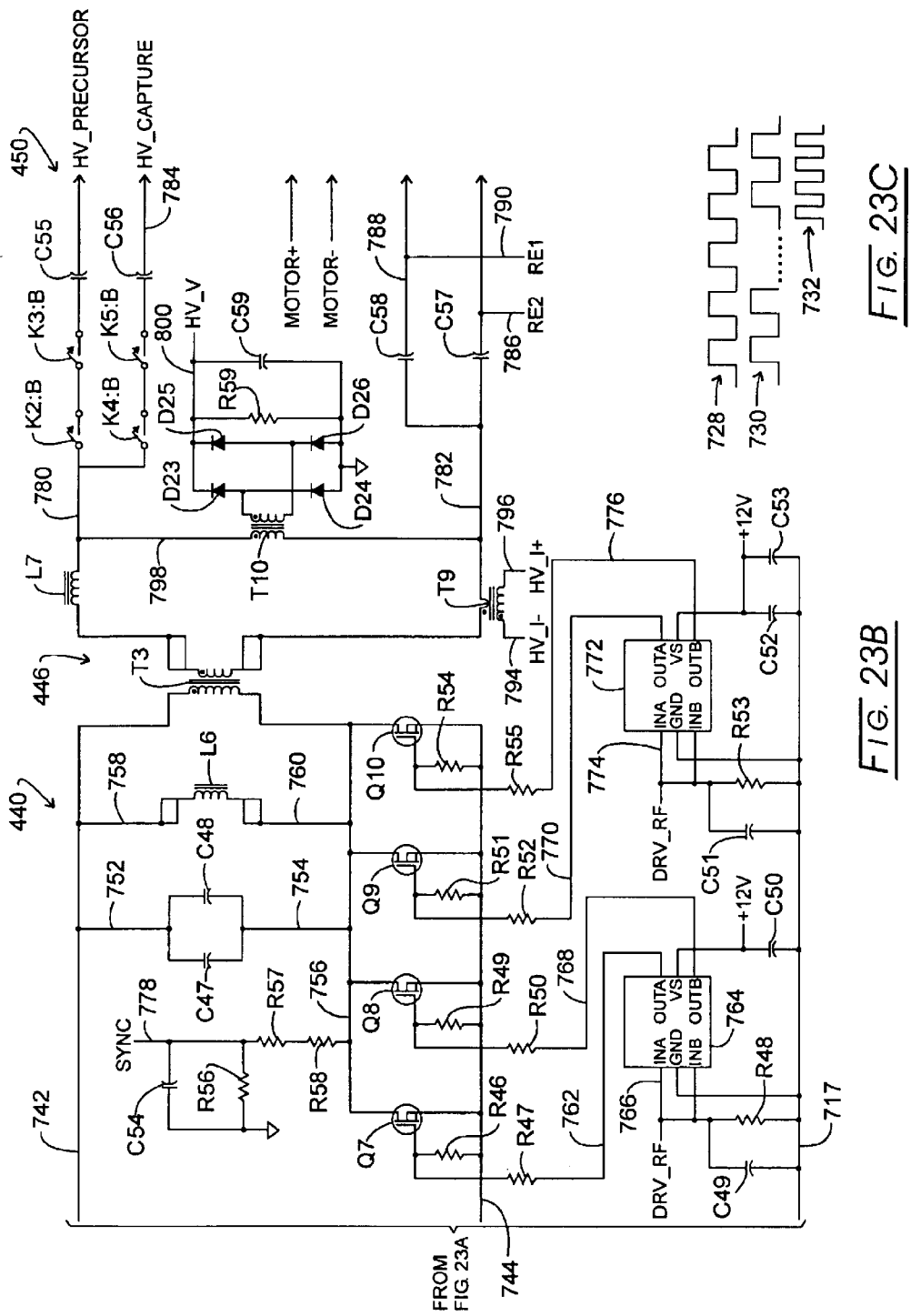

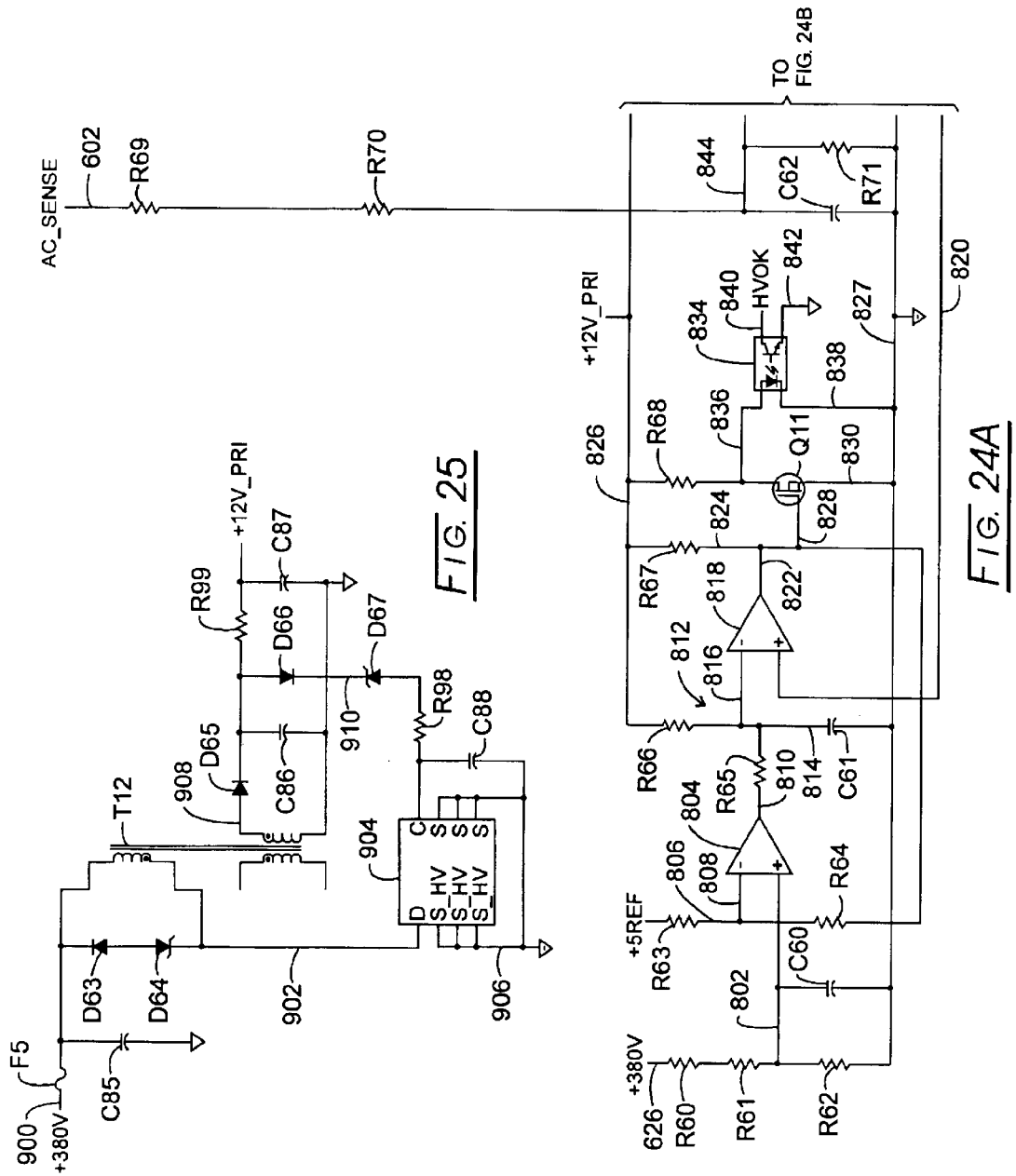

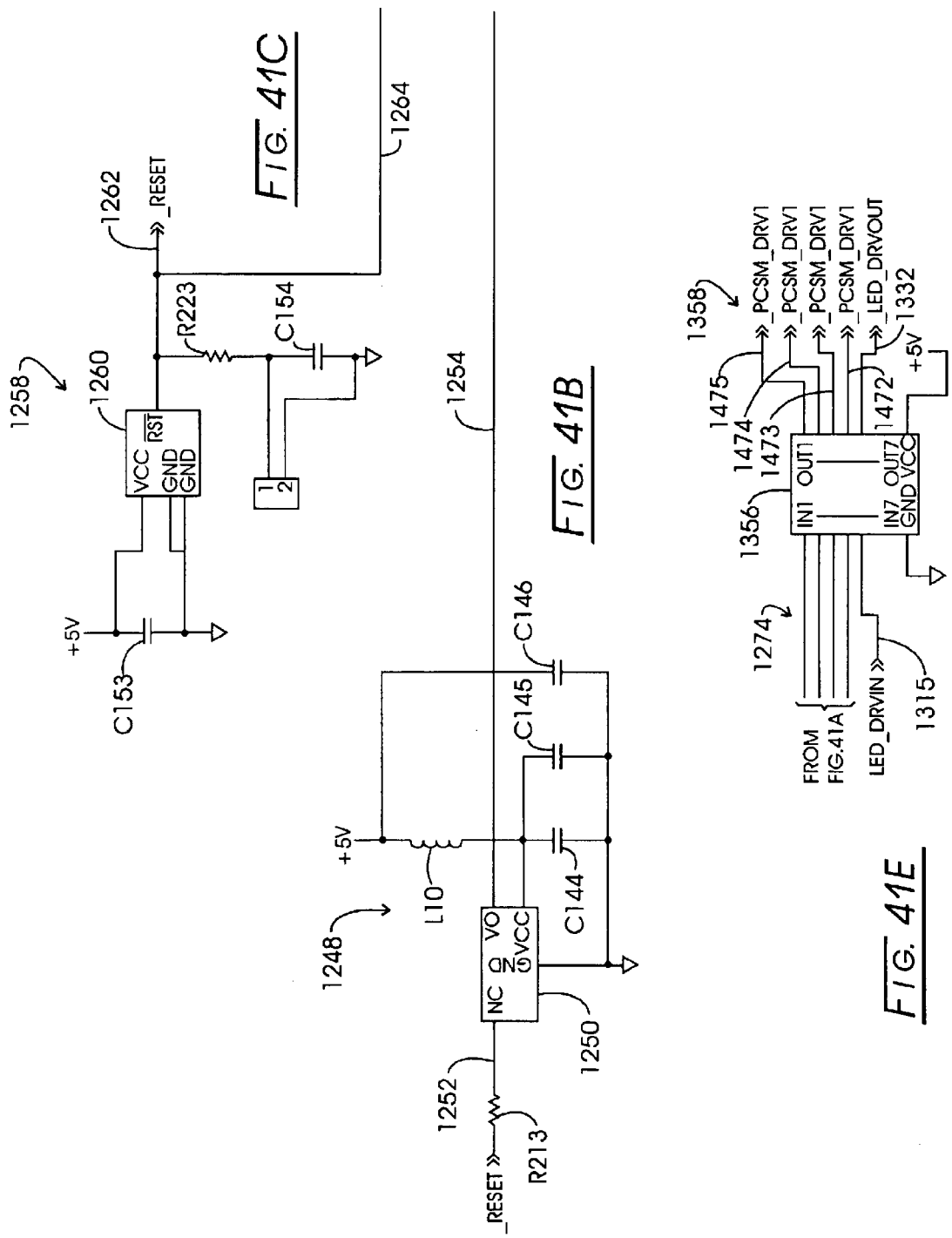

ELECTROSURGICAL GENERATOR

CROSS-REFERENCE TO RELATED APPLICATIONS

This application is a continuation-in-part of U.S. application Ser. No. 09/904,412 filed Jul. 12, 2001. U.S. Pat. No. 6,740,079 B1.

STATEMENT REGARDING FEDERALLY SPONSORED RESEARCH

Not applicable.

BACKGROUND OF THE INVENTION

The use of electrotherapy by medical investigators historically reaches back to the eighteenth century. In that era, electrotherapy static generators were the subject of substantial interest. As the twentieth century was approached, experimentation applying high frequency currents to living tissue took place, d'Arsonal being considered the first to use high frequency currents therapeutically. The use of high frequency currents for the purpose of carrying out electrosurgical cutting and the like was actively promoted in the 1920s by Cushing and Bovie. In the 1970s, solid state electrosurgical generators were introduced, and a variety of such generators now are available in essentially all operating theatres.

When high frequency currents are used for cutting and coagulating, the tissue at the surgical site is subjected to controlled damage. Cutting is achieved by disrupting or ablating the tissue in immediate apposition to the excited cutting electrode, i.e., slightly spaced before it so as to achieve the formation of a cutting arc. Continuous sine waveforms generally are employed to carry out the cutting function where tissue cells adjacent to the electrode are vaporized. An advantage of this electrosurgical cutting procedure over the use of the cold scalpel resides both in an ease of cutting and a confinement of tissue damage to very small and shallow regions. In the latter regard, cells adjacent the cutting electrode arc are vaporized and cells only a few layers deeper are essentially undamaged. These cutting systems, in general, are employed in a monopolar manner wherein the cutting electrode is considered the active one and surgical current is returned from a large, dual component dispersive electrode coupled with the skin of the patient at a remote location.

Coagulation also may be carried out using a high frequency generator source and is accomplished by denaturation of tissue proteins due to thermal damage. Interrupted or discontinuous waveforms typically are employed to carry out coagulation. Coagulation is considered generically as including:

(1) fulguration in which tissue is carbonized by arc strikes,
(2) desiccation in which the cells are dehydrated, and
(3) white coagulation in which tissue is more slowly heated to a coagulum.

The interrupted wave based coagulation procedure has been carried out with both monopolar and bipolar systems.

In order to obtain cutting with hemostasis to arrest bleeding, present day electrosurgical generators may be controlled to blend cutting and coagulating waveforms. To achieve this blend, for instance, a lower amplitude continuous sine waveform is combined with higher amplitude coagulate pulses prior to output voltage elevation by power amplification procedures or the like.

The electrosurgical cutting reaction has been the subject of considerable study. In this regard, some investigators observed that cutting is achieved as the electrical conduction of current heats the tissue up to boiling temperatures and the cells are basically exploded as a result of the phase change. Another, parallel mechanism has been described wherein, as an intense electromagnetic field impinges on absorbing tissue, an acoustic wave is generated by the thermal elastic properties of the tissue. The origin of the pressure wave lies in the inability of the tissue to maintain thermodynamic equilibrium when rapidly heated. See generally:

"Electrosurgery" by J. A. Pierce, John Wiley & Sons New York, N.Y.

Paramount to the cutting procedure is the generation of an arc within the evoked vapor phase. When cutting is being performed, the cutting electrode is not in mechanical contact with tissue, but rather rides on a vapor film as it is moved through the tissue. Thus, it is the separation between the cutting electrode and tissue which allows the possibility for arc formation while cutting. With the existence of this arc, current flow is highly confined, arcs by their nature being quite localized in both space and time, consisting of very short high current density discharges.

Electrosurgical generators generally are configured to derive a requisite arc formation with an active electrode of fixed geometry. For instance, the active electrodes may take the shape of a rod or spade-shaped scalpel. Arc formation requires technique on the part of the surgeon, the electrode being gradually moved toward target tissue until the spacing-based impedance is suited for striking an arc. The energy creating the arc typically is generated by a resonant inverter operating at an RF frequency. Control over such inverters is problematic, inasmuch as the arc represents a negative dynamic impedance. In general, some regulation of voltage feeding the RF invertors is carried out, however, overall output control is based upon a power level selection. Inverter control by output voltage feedback generally has been avoided due principally to the above-noted load characteristics of the necessary arc. Such attempted control usually evolves an oscillatory instability. Accordingly, power-based control is employed with marginal but medically acceptable output performance.

Currently developing electrosurgically implemented medical instrumentation, however, has called for active cutting electrodes of highly elaborate configuration with a geometry which alters in active surface area during a procedure. Generators exhibiting a relatively constant power output cannot sustain an arc under such operational conditions. In this regard, the power output must be variable to track the changing shape and size of the active electrode. This, in effect, calls for an electrosurgical generator capable of producing an RF cutting output under constant voltage control and variable power conditions.

Another developing operational requirement for the electrosurgical generator is a concern for initial arc formation. Applications of the newly contemplated systems call for arc start-up when the active electrode is embedded within and in contact with the tissue to be cut. No preliminary impedance defining spacing otherwise attained by the technique of the surgeon is available to achieve initial arc formation.

BRIEF SUMMARY OF THE INVENTION

The present invention is addressed to an electrosurgical generator capable of forming and sustaining a cutting arc at an active electrode exhibiting dynamic active surface area characteristics. Studies have revealed that human, as opposed to porcine, tissue exhibits a quite expanded range of resistances or impedances. Thus, earlier contemplated constant voltage control designs tended to overpower the system when encountering low load resistance. This resulted in excessive artifacts in the recovered tissue specimens. On the other hand, the very high resistance encountered with very dense tissue resulted in excessively diminished power. Thus, the instant feedback regulated constant power approach evolved. In effect the present system performs to provide a substantially uniform electrothermal cutting action over a broadened tissue resistance range of from about 100 to about 2000 ohms.

The electrosurgical generator incorporates an input treatment network which includes a power factor control stage functioning to align incoming current and voltage with the attendant traditional advantages. However, this input stage both permits use of the generator on a universal, worldwide basis notwithstanding variations in utility power specifications, and, importantly, establishes an interim regulated voltage level which is advantageously utilized by a d.c. link inverter deriving a controlled d.c. link voltage.

Other objects of the invention will in part, be obvious and will, in part, appear hereinafter. The invention, accordingly, comprises the apparatus and method possessing the construction, combination of elements, arrangement of parts and steps which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 4 is a top view of a leaf assembly employed with the instrument shown in FIG. 2;

FIG. 5 is a general sectional view of a capture component and associated drive tube;

FIG. 11A is a schematic representation of a patient and an electrosurgical system provided to demonstrate tissue impedance and total impedance;

FIG. 11B is a schematic representation of a portion of the illustration of FIG. 11A;

FIG. 12 is a schematic chart demonstrating the formation of an arc with a conventional electrosurgically active electrode of fixed geometry;

FIG. 15 is a block schematic diagram of the electrosurgical generator and control features of the invention;

FIGS. 23A and 23B combine as labeled thereon to provide an electrical circuit diagram of a 100 KHz inverter, an isolation transformer, a rectifier, an LC filter, relay disconnects, an RF inverter, a high voltage transformer and a high voltage output stage shown in block diagrammatic fashion in FIG. 15;

FIG. 23C is a schematic pulse diagram illustrating the operation-of the resonant transition phase shift converter shown in FIG. 23A;

FIGS. 24A and 24B combine as labeled thereon to provide an electrical schematic diagram of a link voltage evaluation circuit and a controller for a power factor correction boost converter with associated enablement circuitry;

FIG. 25 is an electrical schematic diagram of a primary side power supply;

FIGS. 41A–41E combine as labeled thereon to describe a programmable logic device-based circuit with associated output buffering and filtering;

DETAILED DESCRIPTION OF THE INVENTION

In the discourse to follow, the electrosurgical generator of the invention with it's attendant boost voltage feature is described in conjunction with a topology selected for use with an electrosurgically supported tissue capture instrument. The embodiment of that instrument is one which employs only electrosurgical cutting current sine waveforms, a cauterization attribute not being incorporated with the discussion. However, the instrument, along with variations including those calling for cauterization are described in U.S. Pat. No. 6,277,083 entitled "Minimally Invasive Intact Recovery of Tissue", by Eggers, et al., issued Aug. 21, 2001 and in U.S. Pat. No. 6,471,659 issued Oct. 29, 2002 entitled "Minimally Invasive Intact Recovery of Tissue, by Eggers, et al. The electrosurgical generator of the invention is described with a configuration based upon a constant voltage attribute dominating at higher load impedances and a constant power output dominating at low load impedances. This combination achieves substantially constant power output over a somewhat expanded tissue resistance range, i.e., reaching down to about 100 ohms and extending upwardly to about 2000 ohms.

Figure 1:
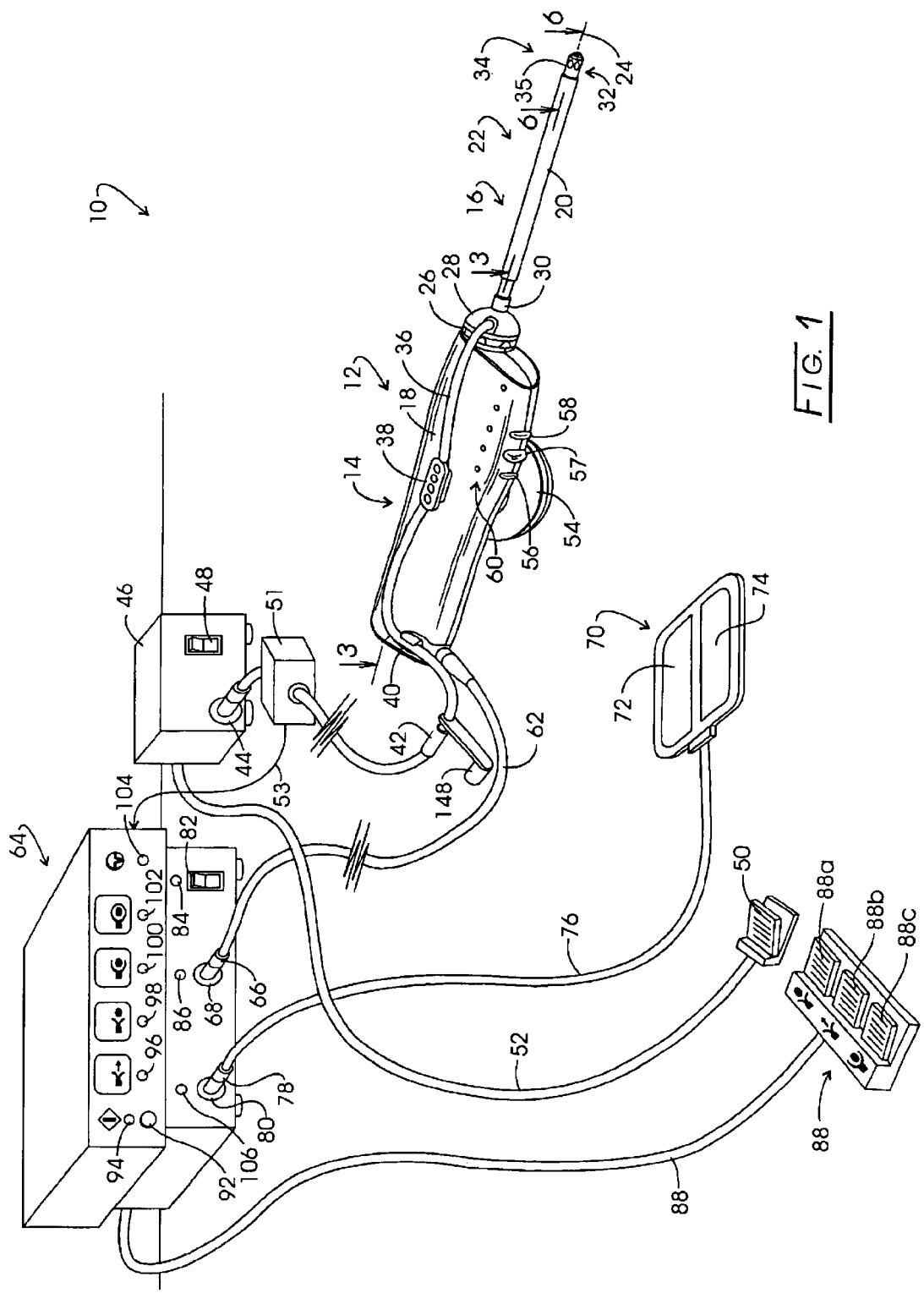
FIG. 1 is a perspective view of the system incorporating the electrosurgical generator of the invention.

Referring to FIG. 1, the electrosurgical generator of the invention is depicted as a component of an electrosurgical intact tissue recovery system shown generally at 10. System 10 includes a tissue retrieval instrument represented generally at 12 which includes a reusable component represented generally at 14 and a disposable component represented generally at 16, the rearward portion of which is removably mounted within component 14. The reusable component 14 includes a polymeric housing 18.

Disposable component 16 includes an elongate delivery cannula represented generally at 22 having a heat shield 20 and which extends along a longitudinal cannula or instrument axis 24. The distal end of the delivery cannula 22 extends through a rotatable threaded connector 26 which is threadably engaged with the housing 18, as well as through a freely rotatable suction manifold 28 which is retained in position by a collar 30. The forward region of the cannula 22, as represented at 32 extends to a distal end or tip represented generally at 34. A flexible suction conduit providing a smoke/steam evacuation function is shown at 36 extending from manifold 28 into press fit connection with a connector 38 as well as through a connector 40 and intermediate releasable connector 42 to the suction input 44 of the housing or console of a vacuum system 46. Housing 46 includes an on/off switch 48 and is actuated to provide smoke/steam/body fluid clearing suction at conduit 36 by a footswitch 50 coupled to the console 46 via a cable 52. Smoke/steam evacuation from distal end 34 is called for to avoid thermal injury to tissue due to a migration of steam back along the exterior surface of cannula 22. The vacuum system extends to tip region 32. In this regard, located at end 32 are four smoke/steam collection or suction intake ports as are represented at 35. Cannula 22 is thermally insulated by the insulative sheath 20 to avoid external tissue damage. Such thermal insulation is described in copending application for U.S. patent Ser. No. 10/630,100 filed Jul. 30, 2003 and entitled. "Electrosurgical Accessing of Tissue With Controlled Collateral Thermal Phenomena".

Grip connectors as 38 are positioned on each side of the housing 18 and function additionally to support a stabilizer handgrip, for example, the annulus-shaped grip represented at 54. Positioned at the forward portion of the housing 18 are three button switches 56–58 which will be seen to function respectively as an arm/disarm switch; an energize position switch; and a start tissue capture switch. Immediately above the switches 56–58 on each side of the housing 18 are linear arrays of LED-based indicator or cueing lights, one such array being represented generally at 60. The visual cues provided by the indicators at 60, from front to rear, provide a start/reset cue as a green light; a tissue capture complete cue provided as a green light; a start tissue capture cue (above switch 58) provided as a yellow light; an energize position cue (above switch 57) provided as a yellow light; and an arm/disarm tissue capture cue (above switch 56) provided as a green light. Energization and control is provided to the instrument 12 via a multi-strand cable 62 which connects with a combined control assembly and electrosurgical generator console represented generally at 64. Connection is shown through a multi-lead connector 66 which is coupled to a console connector 68. The electrosurgical active electrode assembly of the instrument 12 performs in monopolar fashion. Thus, a conventional, relatively large, dispersive return electrode assembly as at 70 is positioned adjacent the skin surface of the patient. Assembly 70 is configured as having two electrode components 72 and 74 which are connected via cable 76 and connector 78 to a console connector 80. Alternatively, a return electrode may be positioned on the surface of delivery cannula 22 near its distal end in place of the illustrated use of return 70.

Power is supplied to the circuitry at console 64 upon actuation of an on/off switch 82. When switch 82 is in an "on" orientation, a green visual indicator LED 84 located above the switch is energized. Proper connection of the cable 62 and connector 66 with console connector 68 is indicated by an illuminated green LED 86 positioned above connector 68. This connection test is carried out by directing current to a coding resistor within housing 18. A three-pedal footswitch represented generally at 88 is coupled via a cable 90 to the rear panel of console 64. The three-pedals, 88a–88c of switch 88 emulate and provide alternative switching with respective button switches 56–58.

Visual cueing corresponding with that at housing 18 LED arrays as at 60 also is provided at the console 64. In this regard, a start/reset switch 92 is operationally associated with an LED indicator light 94 which illuminates in a green color upon actuation of that switch. A yellow position mode visual cue LED representing an energization of the noted precursor electrode is shown at 96. This LED provides a yellow output during the electrosurgical advancement of the delivery cannula tip 34 into confronting adjacency with a targeted tissue volume. Next, a green, arm capture mode visual cue is provided by an LED 98 to represent an arming of the tissue capture feature of instrument 12. Once an arm/disarm switch as at 56 or 88a is depressed the energize position switches as at 57 or 88b are no longer activatable. However, the practitioner may return to the position mode by again depressing an arm/disarm switch. A yellow capture mode visual cue is provided by an LED 100 to represent the start of and carrying out of a tissue capture procedure and upon completion of such capture, a green capture complete mode visual cue is provided by a green LED 102. A pause mode condition is represented by the energization of a green LED 104. In general, the pause mode is entered during a procedure by releasing capture switch 58 or footswitch 88c.

Because of the above-noted opportunity for steam migration, it is preferred that system 10 provide an assurance that the vacuum system as represented at housing or console 46 be actuated. Preferably, the control assembly of console 64 functions to permit commencement of the procedure only upon a turning on of system 46. Such a monitoring of system 46 is accomplished with a vacuum actuated switch shown at block 51 attached within conduit 36. The monitoring output to console 64 is represented at arrow 53.

At the time connector 78 of the return electrode 70 is coupled to console connector 80 and switch 82 is in a power on condition, a patient circuit safety monitor circuit (PCSM) carries out a self test. Upon subsequent actuation of start/reset switch 94, a fault test with respect to the two electrode components 72 and 74 is performed. In the event the latter test fails, then both visual and aural pulsating warning cues are activated, the visual cue being provided at a red LED 106 located adjacent connector 80.

Figure 2:
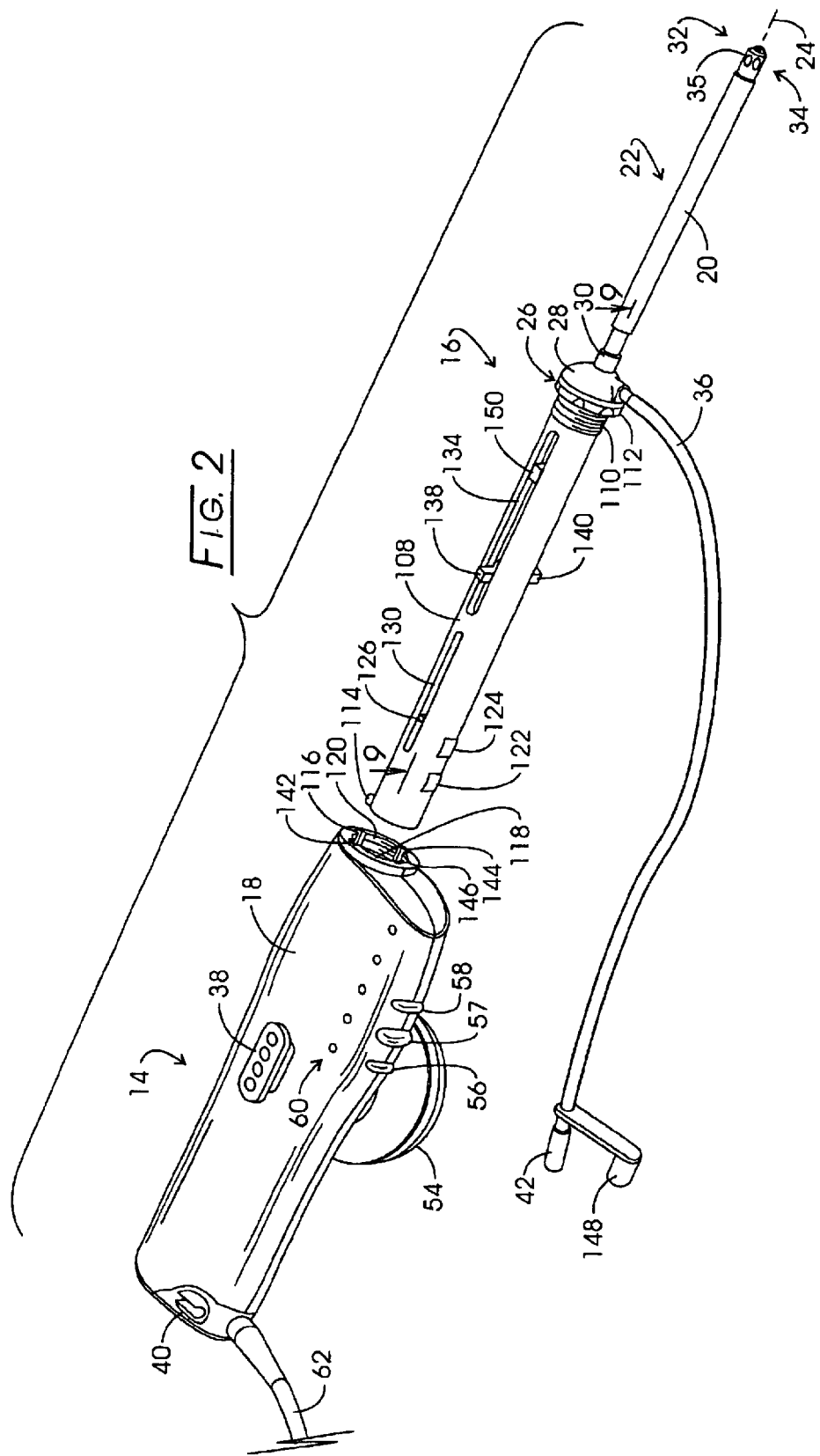
FIG. 2 is a perspective view of the instrument shown in FIG. 1 with a disposable component being shown removed from a reusable housing.

Referring to FIG. 2, the disposable component 16 of instrument 12 is revealed in an orientation prior to insertion within the housing 18 of reusable component 14. In the figure, delivery cannula 22 is again seen extending forwardly from a cylindrically shaped support housing 108. The forward region of support housing 108 supports the rotatable connector 26. In this regard, it may be observed that the connector 26 is configured with external threads 110 which are fixed for rotation with a knurled flange 112. At the rearward end of support housing 108 there is located an upstanding indexing pin 114 which, during installation of the disposable component 16 is slidably received within an upwardly disposed elongate slot 116 extending internally along an elongate receiving cavity 118 within the housing 18. Internal threads 120 within the cavity 118 threadably engage the external threads 110 of connector 26 when the disposable component 16 is inserted within the reusable component 14.

Positioned opposite indexing pin 114 on support housing 108 are two, spaced apart electrical contacts 122 and 124 which are oriented to make wiping contact with corresponding electrical terminals disposed within housing 18 upon insertion of support housing 108 within the receiving cavity 118. Contacts 122 and 124 selectively receive electrosurgical cutting current applied respectively to a precursor electrode assembly at tip 32 and the electrosurgical cutting and pursing cables associated with a capture component. Those cables extend from the capture component within delivery cannula 22 to a cable terminator component having guidance tabs or ears one of which is revealed at 126 slidably mounted within an elongate stabilizer slot 130 arranged in parallel with axis 24. A corresponding guidance tab and slot combination is found at the opposite side of the support housing 108. Located forwardly of the slots as at 130 are two additional elongate drive slots one of which is shown at 134 similarly arranged in parallel with axis 24. The outwardly extending ears or guide tabs of a drive assembly drive member extend from these slots and are seen at 138 and 140. These ears or tabs 138 and 140 support rearwardly disposed driven surfaces which are used to impart forward movement to the drive assembly. This forward movement functions to deploy a capture component from delivery cannula 22. When the support housing 108 is installed within the receiving cavity 118 of housing 18, these tabs 138 and 140 pass through oppositely disposed notches shown respectively at 142 and 144 provided at the forward portion of housing 18. Similarly, a notch 146 is located forwardly within reusable housing 18 to permit passage of the electrical terminals 122 and 124. As is apparent, the procedure for installing the disposable component 16 within the reusable component 14 involves the sliding of disposable support housing 108 within the receiving cavity 118 and rotating knurled portion 112 of connector 26 to provide the engagement of threads 110 with threads 120. The figure also shows a vacuum forming closure plug 148 which is utilized following the procedure for blocking connector 42 of hose or conduit 36 to trap any fluids within the instrument-connected forward component of the latter conduit. Finally, a tab 150 is seen extending through a forward portion of the drive slot 134. This tab is a component of a drive assembly safety stop 304 (FIG. 9) functioning to limit the extent of forward travel permitted by the drive member with ears 138 and 140 in accordance with a pre-selected capture component diametric extent.

Figure 3:
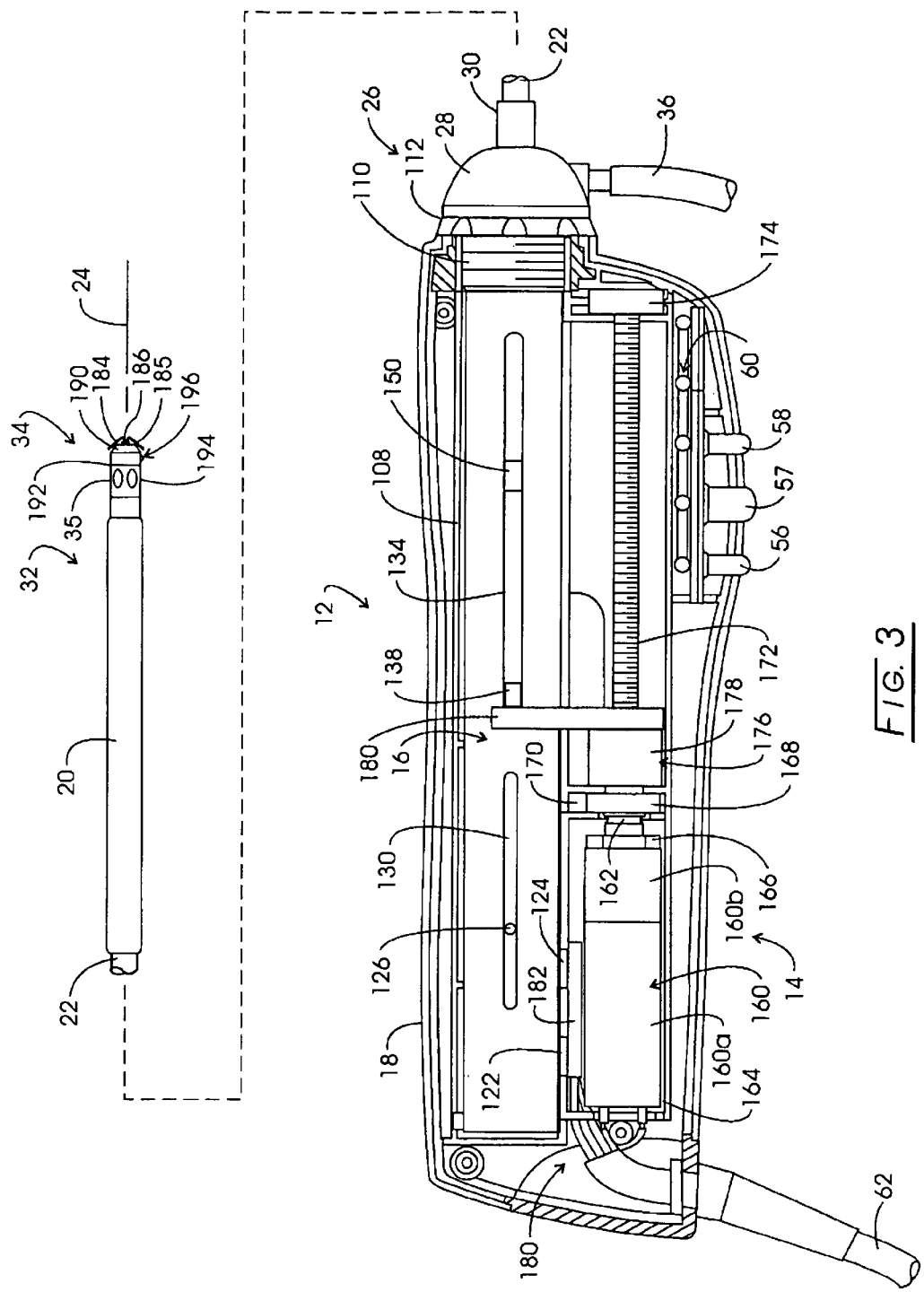
FIG. 3 is a partial sectional view of the instrument of FIG. 2.

Referring to FIG. 3, a sectional view is presented illustrating the operative association of the drive features retained within reusable component 14 and the driven features of disposable component 16. In the figure, a motor assembly is represented generally at 160. The assembly 160 is formed of a d.c. electric motor 160a which is combined with a planetary gear assembly 160b. Assembly 160 provides a rotational output at a stainless steel bellows-shaped somewhat flexible coupler 162 and is located within a motor mount chamber 164. Within that chamber 164, the motor assembly 160 is permitted some self-aligning movement but is restrained from rotational movement by a torque stop component 166. For the instant embodiment coupler 162 extends through a taurus-shaped fluid seal 168 located within a seal chamber 170. This flexible seal 168 does not constrain the coupler 162 and permits the noted self-alignment of the motor assembly 160 with respect to an elongate rod-shaped translation component 172. Component 172 is seen extending forwardly to a rotatable and fixed connection with a thrust bearing 174. Bearing 174 provides support against all of the driving forces imposed from the motor assembly 160. In this regard, the rod-shaped threaded translation component 172 is threadably engaged with a transfer assembly represented generally at 176. Transfer assembly 176 comprises a ball screw or nut component 178 threadably engaged with the threads of component 172 and a generally Y-shaped yoke 180 which is configured having spaced apart drive members configured to extend to a position spaced from but aligned for driven engagement with the tabs or ears 138 and 140 (FIG. 2) of a drive member when the support housing 108 initially is inserted in the receiving cavity 118. To assure non-binding performance of the above drive components, it is necessary to avoid axial creep phenomena and the like which may be manifested as a compression of bellows 162. In general a sleeve is provided over the output drive shaft of assembly 160, while a corresponding stepped-down diameter at component 172 provides a shoulder against which the coupler 162 abuts.

Electrosurgical cutting current as well as control inputs and outputs are introduced from cable 62 to the housing 18. Two of the multi-lead components, certain of which are revealed at 180, extend to a contact clamp 182 which retains two contacts for supplying electrosurgical cutting energy to contacts 122 and 124 of the disposable component 16.

FIG. 3 also reveals some details of the tip 34 of delivery cannula 22. That tip 34 is depicted as it is utilized for relatively smaller tissue volumes, for example, encompassed within a diametric extent of about 10 mm. The tip incorporates four precursor electrode components arranged in a cross shape symmetrically about longitudinal axis 24. Two of the electrosurgical cutting portions of the precursor electrodes are revealed at 184 and 185 located just forwardly of a truncated cone-shaped ceramic (alumina) protective tip 190. Tip 190 functions to provide an arc-resistant or arc isolating tip portion preventing its breakdown. Rearwardly of ceramic tip 190 are polymeric tip components 192 and 194 which are coupled to delivery cannula 22. The latter component 194 is seen to carry the earlier described suction ports 35. The former component 192 provides a ramp structure for a sequence of five thin stainless steel leafs of a capture component, the tips of which carry braided stainless steel pursing cables which are electrosurgically excited for cutting purposes and which create a pursing action cutting to form a cage-like structure around a targeted tissue volume. Alternatively, the precursor electrode, leafs, pursing cable and cannula may be constructed of non-ferromagnetic materials (e.g., titanium, nitinol) to enable use of this device with magnetic resonance image guidance of a biopsy procedure. Drive imparted to these capture component leafs emanates from the yoke 180 and drive member ears 138 and 140. Each of these leafs terminates in eyelets at its leading edge certain of which are represented generally at 196. The polymeric tip components 192 and 194 cooperate to form a guidance assembly represented generally at 198 which functions to direct the leafs, appropriately spaced apart and at a proper attack angle, in a capture maneuver. That attack angle for the instant embodiment is 45°.

Delivery cannula 22 has a relatively small diametric extent, for example, about 5 mm. Within its forward portion 32 there is disposed an earlier-noted capture component comprised of a pentagonally-shaped stainless steel elongate leaf structure with a leading edge formed with dual eyelets which carry a five pursing cable assembly. Referring to FIG. 4, the capture component is represented generally at 200 at a stage in its fabrication prior to the attachment of the noted pursing cables along with polymeric guide tubes. As revealed in the general sectional view of FIG. 5, the capture component 200 has a generally pentagonal cross sectional configuration initially chemically milled from flat stainless steel stock such that the forward portion 202 is formed with a sequence of five leafs having a thickness of 0.003 inch and a widthwise extent of 0.080 inch. The five leafs are shown in these figures at 210–214 and extend from a pentagonal base portion 218 to the noted dual eyelet tips 196. Each of the leafs 210–214 is chemically milled with a somewhat centrally disposed groove extending longitudinally along their lengths. Within this groove, as seen in FIG. 5, there is adhered a polyamide flexible guide tube. These guide tubes are quite small, having, for example, an outside diameter of about 0.020 inch and a wall thickness of about 0.0015 inch. The guide tubes are shown in FIG. 5 at 220–224 as being adhesively attached to respective leafs 210–214. Each of the guide tubes 220–224 slidably guides a pursing cable as shown respectively at 230–234. These multistrand stainless steel cables have a diameter of about 0.006 inch. The polyamide guide tubes 220–224 are attached by initially adhesively coupling them to the noted troughs. Then, the tubes are bonded to a corresponding leaf within the chemically milled groove utilizing an electrically insulating coating material and process which achieves bonding and provides requisite electrical insulation for the entire capture component assembly 200. The coating, which has a thickness of about 0.001 inch, is a vapor-phase-polymerized conformal coating marketed under the trade designation "Parylene". Parylene is the generic name for members of a polymer series. The basic member of the series, called Parylene C is poly-para-xylene, a completely linear, highly crystalline material. Such coatings are available from Parylene coating service companies such as Specialty Coating Systems, (SCS) of Indianapolis, Ind. FIG. 4 reveals the eyelet structure at the leading edge of capture component 200. The leading edges containing the eyelets are bent outwardly from the orientation shown prior to the attachment of cables through them. Further, the capture component 200 is weldably attached to a drive tube or drive rod 236 which extends rearwardly into support housing 108 and into engagement with the drive member associated with the tabs or ears 138 and 140 (FIG. 2).

Figure 6:
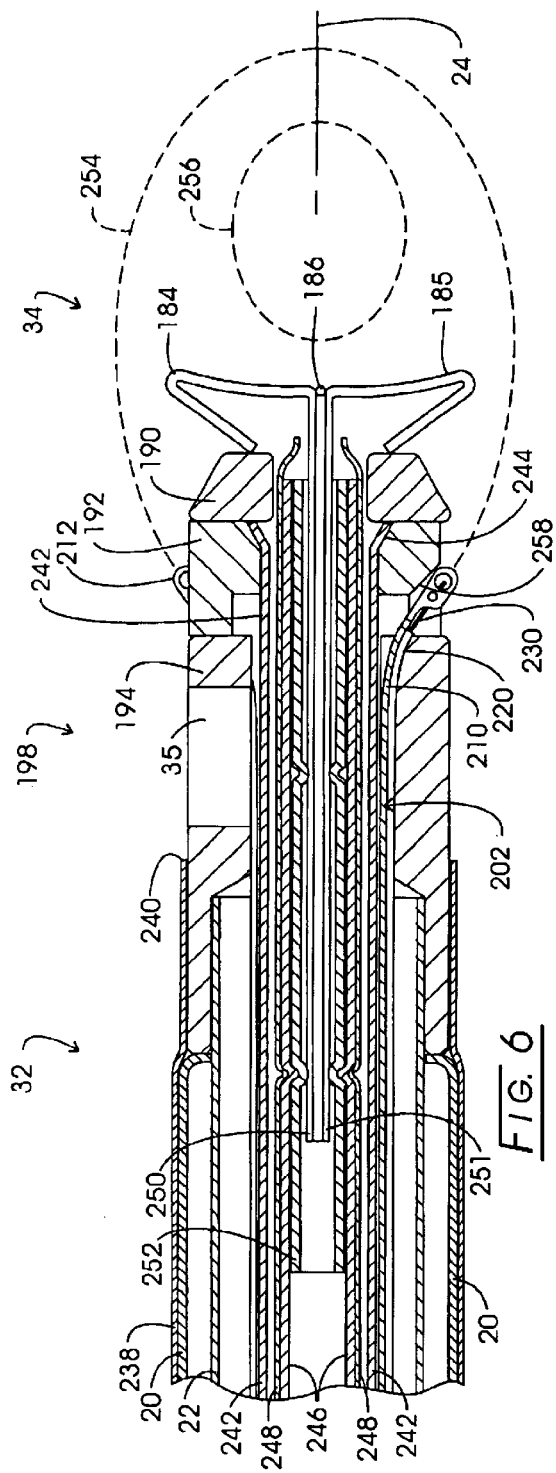
FIG. 6 is a partial sectional view of the forward region of the instrument of FIG. 2.

Referring to FIG. 6, the forward region 32 and tip 34 of the delivery cannula 22 are revealed in sectional detail. In the figure, the delivery cannula 22 with heat shield 20 is seen extending forwardly to the earlier-described polymeric (polyetherimide) tip component 194. Heat shield 20 and portions of cannula 22 are electrically insulated with a 5 mil thick polyolefin shrink tube 238 extending to a border 240 at component 194. Note the insulative air space 21 between heat shield 20 and cannula 22. Inboard from the internal surface of the delivery cannula 22 are the five capture component leafs in pentagonal configuration, portions of two of which are shown at 210 and 212. Extending next inwardly inboard is a stainless steel support tube 242 which is mounted at the rearward portion of the support housing 108 of disposable component 16 and extends forwardly through the delivery cannula 22 to a flared region 244 engaging polymeric tip component 192. This flaring is found to be helpful in permitting the support tube to overcome the rather substantial forwardly directed forces occurring during forward deployment of the capture component leafs and cables. Extending inside the support tube 242 is an electrosurgical precursor electrode tube 246 which also extends to the rearward portion of support housing 108 for purposes of both support and receiving electrosurgical cutting energy transmitted through electrical contact 122 (FIG. 2). As the precursor electrode tube 246 extends rearwardly, it is electrically insulated from support tube 242 by a polymeric shrink wrap 248.

The precursor electrodes are mounted as a subassembly of four stainless steel electrode wires having a generally elongate L-shape, two of which are shown in conjunction with electrodes 184 and 185. In this regard, the elongate components of these electrodes 184 and 185 are shown respectively at 250 and 251 extending into a subassembly tube 252. Four such electrode assemblies are crimped inside this tube 252 and that tube 252, in turn, is crimped within the forward portion of the precursor electrode tube 246. It has been found that the utilization of four cutting surfaces for the electrodes, arranged in a cross-shaped pattern, provides preferable instrument positioning results. Such an arrangement of confronting electrode surfaces is revealed, for example, in connection with FIGS. 7 and 8. In general, the severing portions of the precursor electrodes will be extending normally to the longitudinal axis of the instrument and will be configured to directly confront the tissue being severed during the insertion or placement of the instrument in a confronting relationship to the involved tissue volume. The dimensional extent of the confronting severing portions of these precursor electrodes is selected to provide an effective length less than the corresponding maximum diametric extent developed by the capture component. In FIG. 6, that extent may be observed at stylized dashed locus of movement line 254. In deploying the capture component 200, the forward or leading edge thereof containing the noted arc forming cables will cut a path somewhat similar to that shown at dashed line 254 reaching the capture component predetermined maximum peripheral diametric extent at a point in the deployment when pursing commences as cable forward movement no longer is permitted to effect a contraction and enclosure of an encapsulated tissue volume including a target tissue volume represented symbolically at dashed line 256. Accordingly, power must be supplied to this cutting electrode cable assembly to sustain an arc while accommodating initially for its expanding surface area, i.e., length and then for its contraction toward its procedure terminating very small surface area extent. This may be contrasted with a conventional electrosurgical scalpel having a fixed configuration throughout a cutting procedure. With the instant procedure, both the precursor electrodes 184–187 and the cables 230–234 at their confronting portions are initially and at any re-start embedded in tissue as opposed to being spaced from a tissue surface, a condition ameliorated by the application of a boost voltage level to create an arc at the initiation of electrosurgical cutting, whether at the outset of the procedure, or following a stop in the procedure. Preferably, this boost condition (e.g. 1100 volts, peak-to-peak) is present for only a minimal boost interval sufficient to create a cutting arc. While it is possible to extend this boost interval to the extent of the entire procedure including both the positioning procedure using precursor electrodes and for capturing a specimen with pursing cables, the consequence is the generation of excessive power during the biopsy procedure which results in artifacts at greater depth of thermal injury to the biopsy specimen and surrounding healthy tissue.

FIG. 6 also reveals that polymeric tip component 194 functions as a guide for the leafs 210–214. Similarly, polymeric tip component 192 is configured with five ramps arranged at a 45° angle with respect to the instrument axis 24. One of those ramps is shown at 258 in conjunction with leaf 210. These ramps provide for the 45° angle of attack of leafs 210–214 as they emerge during a capture procedure.

In general, the precursor electrodes 184–187 will have a tissue cutting and confronting length of about 6.5 mm to 7.0 mm for employment with a maximum effective capture diameter for the capture component 200 of 10 mm. Similarly, where that effective diameter expands to 20 mm, the expanse of the precursor electrodes or their lengthwise confronting extent will be about 10 mm. When configured having one of the larger lengthwise extents, the electrodes are slightly canted forwardly and are made resilient so as to be capable of flexing forwardly as the electrosurgically excited pursing cables physically contact the precursor electrodes. During this procedure, the precursor electrodes are open-circuited and permitted to be reenergized as they are urged into alignment with the capture component leafs. This temporary re-energization of the longer precursor electrodes is found to be beneficial as the electrodes retract or bend toward larger tissue samples being captured.

Figure 7:
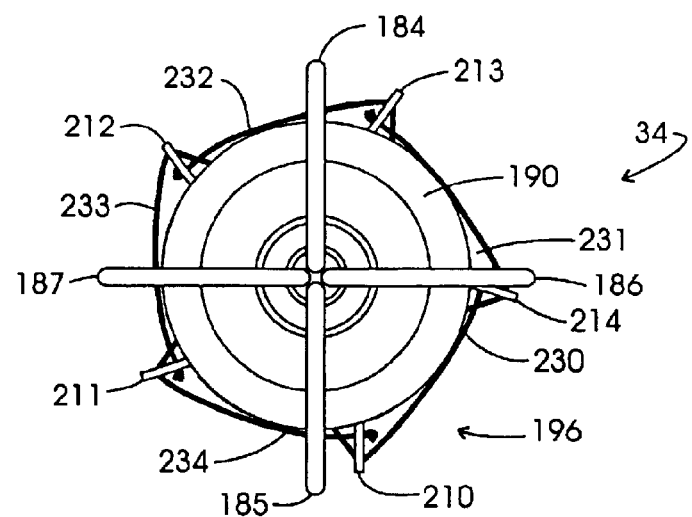
FIG. 7 is a front view of the forward portion of the instrument shown in FIG. 1 with components oriented prior to deployment of capture component leafs.
Figure 8:
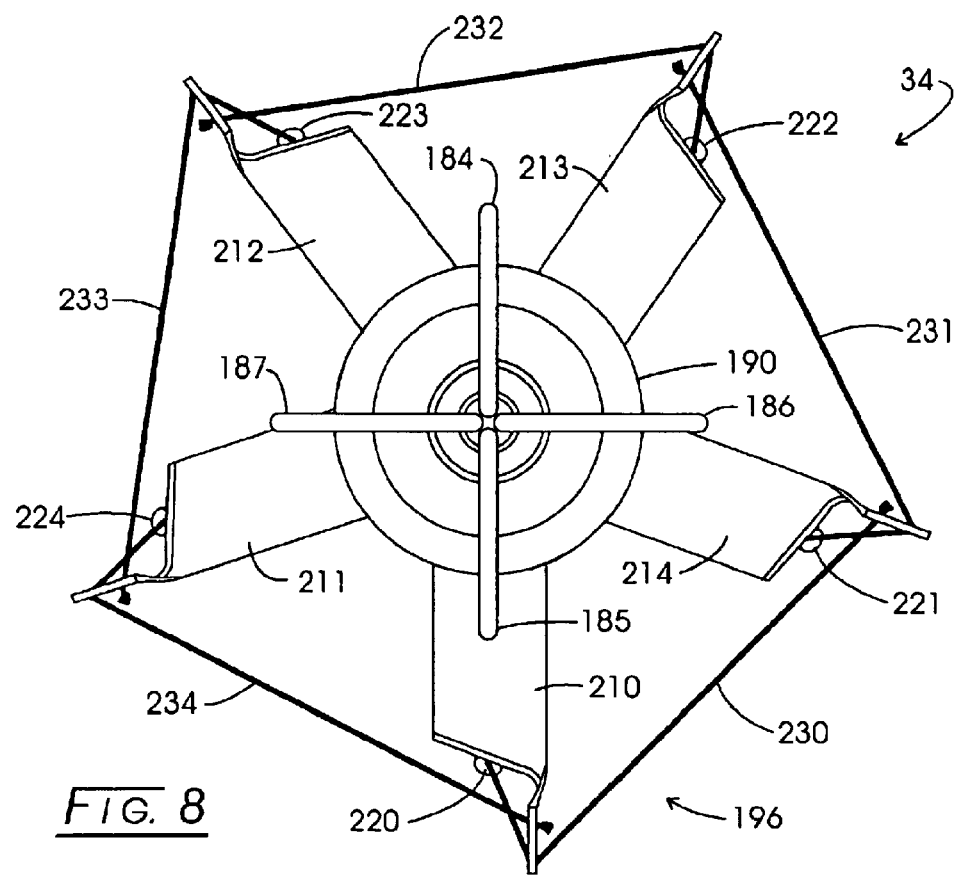
FIG. 8 is a front view of the forward portion of the instrument of FIG. 1 showing the orientation of components as the leafs of its capture component are being deployed.

FIGS. 7 and 8 present front views of the delivery cannula 22 tip 34, illustrating in particular the orientation of the precursor electrodes, as well as the leafs and cables in a retracted state in FIG. 7 and as the leafs and cables emerge in FIG. 8. In the procedure initiation orientation of FIG. 7, the active area extent exhibited by the electrosurgically cutting portions of cables 230–234 is somewhat small but slightly larger than at full pursing at the completion of the procedure. In FIG. 7, the five leaf tips of leafs 210–214 are visible in connection with portions of the pursing cables 230–234. When in this orientation, the precursor electrodes 184–187 will have been excited to form an arc while the instrument 12 is maneuvered into an orientation wherein the tip 34 is in confronting relationship with the targeted tissue volume. The precursor electrode structure then is deactivated (open circuited) and the capture component 200 is deployed in conjunction with the arc forming excitation of pursing cables 230–234 with electrosurgical cutting energy. However, inasmuch as the cables are embedded in tissue, a boost voltage is called for, for a boost interval adequate to evoke formation of a cutting arc between the active portions of cables 230–234 and confronting tissue.

FIG. 8 shows that as the leafs 210–214 are deployed, the pursing cables 230–234 are being "played out" and the effective diametric extent of the capture component is expanding to circumscribe the targeted tissue volume to be removed. To provide the expansion and subsequent pursing arrangement, note that cable 230 slides through guide tube 220 and is attached to the tip of leaf 214. Cable 231 slides through guide tube 221 and is attached to the tip of leaf 213. Cable 232 slides through guide tube 222 and is attached to the tip of leaf 212. Cable 233 slides through guide tube 223 and is attached to the tip of leaf 211; and cable 234 slides through guide tube 224 and is attached to the tip of leaf 210.

Figure 9:
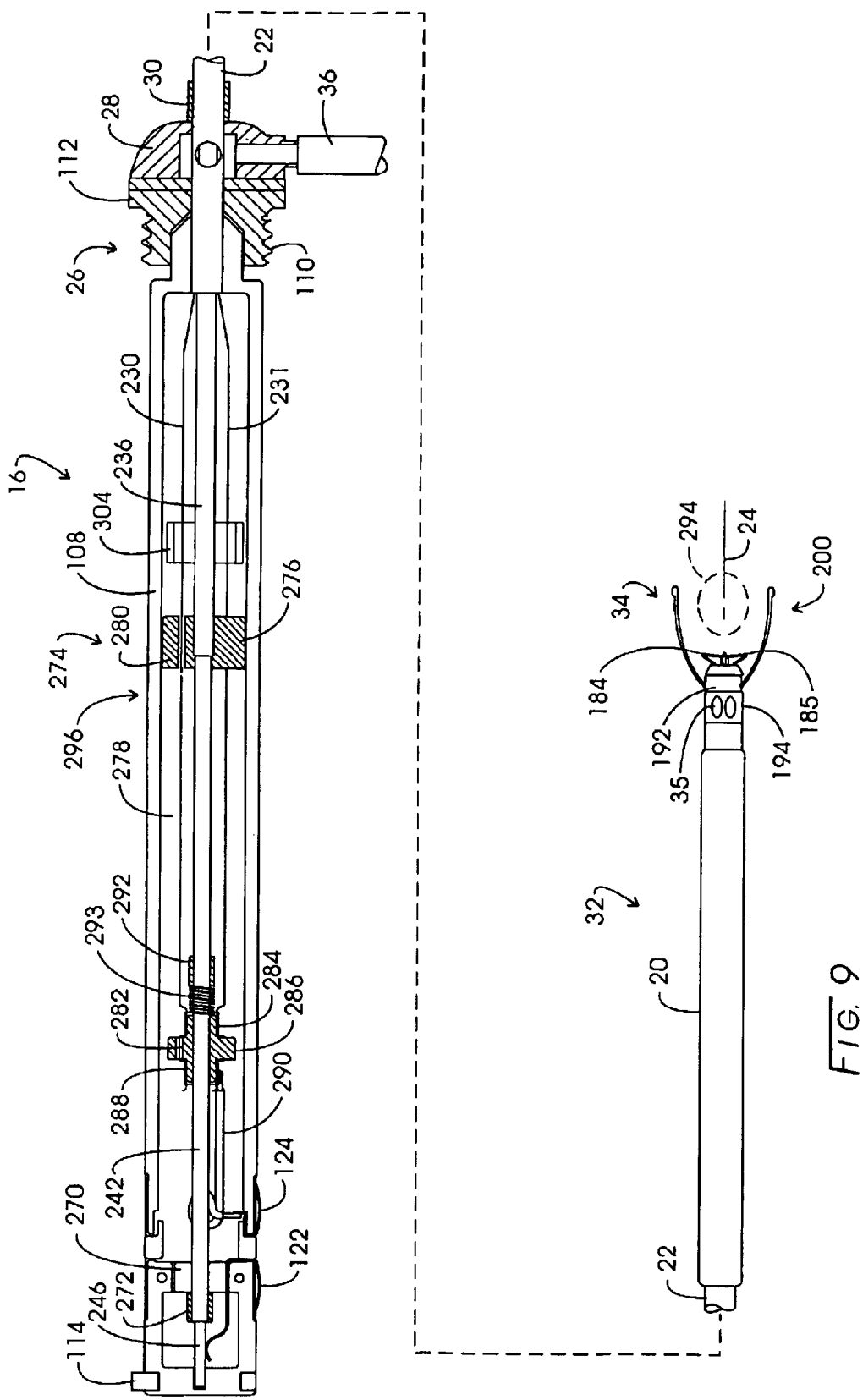
FIG. 9 is a partial sectional view of the disposable component of the instrument shown in FIG. 1 schematically showing a deployment of capture component leafs to a maximum diametric extent.

Referring to FIG. 9, a partial sectional view of the support housing 108 of disposable component 16 is provided. In the figure, the support tube 242 is seen to extend to engagement with a bulkhead 270 at the rearward portion of support housing 108. The tube 270 is retained in position by a collar 272. Extending through the support tube 242 is the earlier-described precursor tube 246 absent the insulative shrink wrap covering 248. Precursor electrode tube 246 is seen to be in abutting contact with electrical contact 122. With this arrangement, electrosurgical cutting energy can be conveyed from the contact 122 into the tube 246 and thence to the precursor electrodes 184–187. The rearward portion of the capture component drive assembly is represented generally at 274 and is seen to include the earlier-described drive tube 236 and a drive member 276. Drive member 276 is shown in a sectional view wherein the integrally formed ears 138 and 140 (FIG. 2) are not seen. However, note that it is coupled to the end of drive tube 236 and both that tube 236 and the drive member 276 slidably move over support tube 242 along the instrument axis 24. The yoke 180 described in connection with FIG. 3 engages the ears 138 and 140 to move drive assembly 274 forwardly by virtue of its abuttable engagement with ears or tabs 138 and 140 (FIGS. 2 and 3).

Pursing cables 230–234 extend rearwardly outboard of the drive tube 236 into the internal cavity 278 of support housing 108. Two of these pursing cables are symbolically represented at 230 and 231. These cables slidably extend through corresponding five channels extending through drive member 276, one of which is shown at 280. The cables 230–234 extend further to a fixed connection with a polymeric cable terminator component 282. Component 282 is slidably mounted upon support tube 242 and includes a forward ferrule or collar 284 which is press-fitted over the cables 230–234. The cables then extend through a central flange portion 286 of component 282 for rigid and electrical connection with a rearward ferrule or collar 288. Collar 288, in turn, is coupled to a flexible electrical cable 290 connected to electrical connector 124, which follows the cable terminator component 282 as it slides forwardly. Accordingly, electrosurgical culling energy is supplied to the cables 230–234 from connector 124, cable 290 and the ferrule 288. Cable terminator component 282 is stabilized by two outwardly extending ears or tabs, one of which is described in connection with FIG. 2 as a tab 126 riding within stabilizer slot 130. Positioned forwardly of cable terminator component 282 is a cable stop 292. The collar-shaped stop 292 is adhesively fixed to support tube 242 at a location defining the maximum diametric extent developed by the leading edge of the capture component 200 leafs. That maximum diametric extent is represented in the instant figure in symbolic fashion as extending over a tissue volume and about halfway over a targeted tissue volume shown in dashed line fashion at 294. It has been determined that a more reliable capture is achieved by positioning a compression spring as at 293 between stop 292 and component 282. This arrangement is described in detail in copending application for U.S. patent Ser. No. 10/630,336 entitled: "Electrosurgical Method and Apparatus With Dense Tissue Recovery Capability" filed Jul. 30, 2003. With the orientation of the capture component 200 shown, the cable terminator component 282 will have commenced to abuttably engage the cable stop 292 through spring 293 to effect a tensioning of the pursing cables 230–234 as the drive assembly 274 continues to be driven forwardly by motor assembly 160, translation component 172 and transfer assembly 176 (FIG. 3). A drive safety stop mechanism comprised of stop member 304 is fixed within cavity 278 to limit the forward movement of drive assembly 274 beyond a location representing a full pursing or contracting of the capture component 200 for the elected maximum diametric extent of capture. Such unwanted movement may occur, for example, with a failure of cable stop 292 to halt forward movement of cable terminator component 282. As drive assembly 274 continues to be driven forwardly and the drive member 276 approaches adjacency with safety stop member 304 the leafs of capture mechanism 200 will be pursed mutually inwardly together to define a confinement structure surrounding the tissue volume to be removed. As this occurs, the relative lengths of active electrode cutting components of the pursing cables commence to diminish to ultimately assume a very small active cutting area. This orientation is revealed in FIG. 10 which shows the positioning of components subsequent to the procedure-based orientations represented in FIG. 9. Drive member 276 and its associated drive tube or rod 236 of drive assembly 274 are seen to have been driven further forwardly, drive member 276 being in spaced adjacency with respect to the drive safety stop mechanism 302. Cable terminator component 282 is in abutting engagement with cable stop 292. This has caused a tensioning of the five cables 230–234 and a pursing encapsulation of the target tissue 294 and surrounding tissue volume which has been carried out by the capture leafs of the capture component 200.

The stress load carried by the cables 230–234 now is of an extent wherein the control features of the control assembly will detect a forward stall condition on the part of motor 160a. As this occurs, cutting energy to the cables 230–234 is terminated and motor assembly 160 is energized to be driven in reverse. Accordingly, yoke 180 will release from freely abutting engagement with tabs or ears 138 and 140 of drive member 276 and that member will return to a home position. The reusable component 14 of the instrument 12 thus is reoriented for a next utilization. In general, the practitioner then decouples coupler 42 of the suction line 36 and traps the fluid therein by inserting the plug 148 within it (FIG. 2). The disposable component 16 then is removed by unscrewing the forward threaded connection at connector 26 and ears or tabs 138 and 140 may be manually returned to abutment with the latch assembly 296. This causes the capture component 200 to approximately reassume the orientation shown in FIG. 9, making the retrieved tissue specimen readily accessible to the practitioner.

Figure 10:
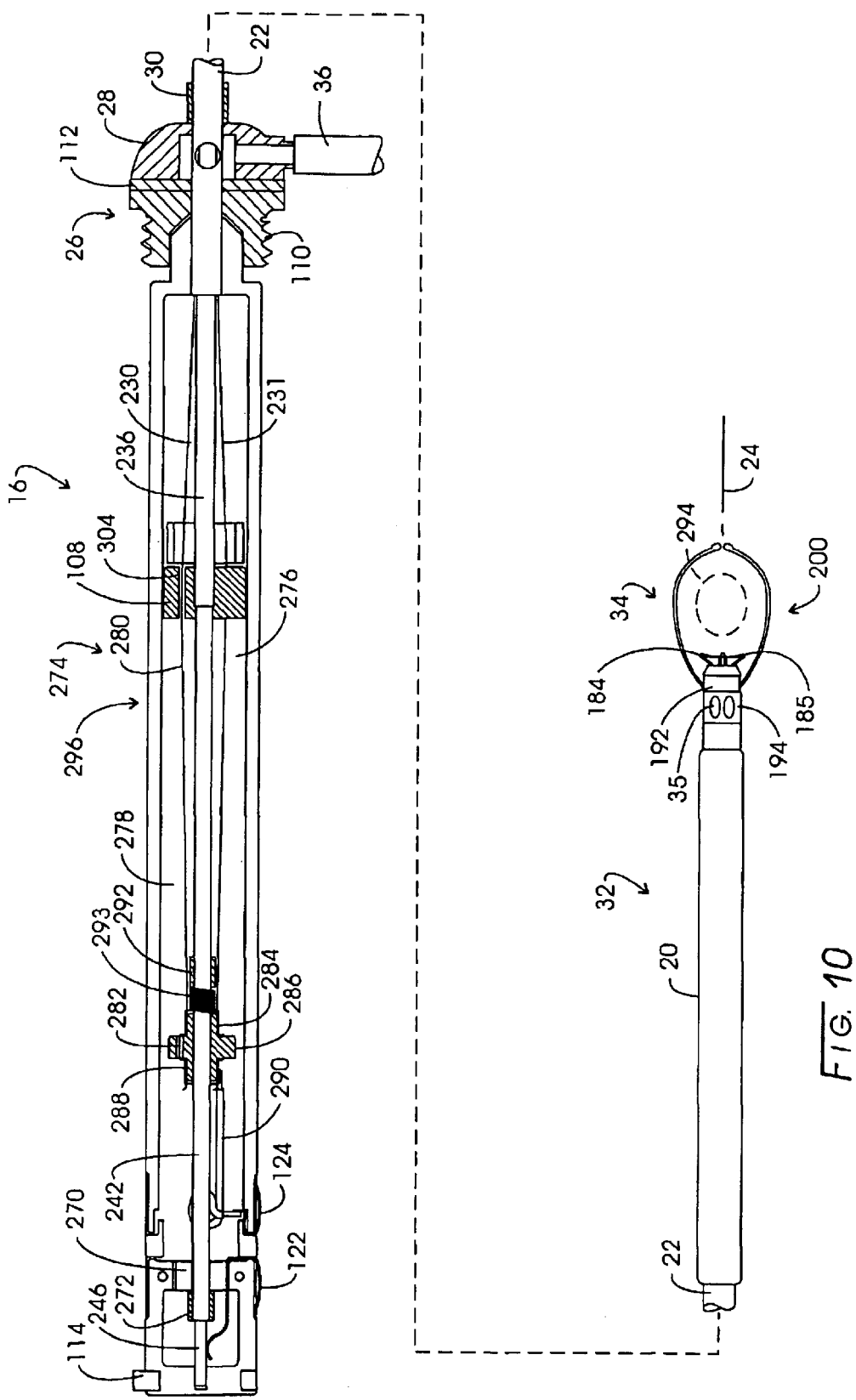
FIG. 10 is a partial sectional view of the instrument of FIG. 9 schematically showing the orientation of the capture component leafs at the completion of capture of a tissue volume.

Referring again to FIG. 1, the procedure carried out with system 10 initially involves the administration of a local anesthetic agent at the skin level in the region of an intended biopsy. Switch 82 is actuated to turn on the console 64 and cable 62 is attached at connector 68. Upon a successful testing of the connection, green LED 86 illuminates. The practitioner presses the start/reset button 92 on console 64, whereupon a patient safety circuit monitor test is carried out, the red LED 106 and an aural cue providing a pulsed output in the event of failure of this test. Disposable component 16 is mounted within the reusable component 14 and a skin incision using a cold scalpel to a depth of about 4 mm and a width of 2 mm wider than the maximum width of the tissue volume to be removed is made. The smoke/steam evacuator 46 is turned on from footswitch 50 and the tip 34 of the delivery cannula 22 is extended into the incision such that the precursor electrodes at its tip are at least 3 mm below the surface of the skin. Thus, these electrodes initially are embedded within the skin. A positioning mode then is commenced with either the depression and continued depression of energize/position footswitch 88b or housing 18 button switch 57 to effect first boost then normal cutting energization of the precursor electrodes. LED 96 is illuminated as well as the corresponding LED at array 60. An aural cue is provided as a steady tone. The tip 34 of the delivery cannula 22 is advanced to a position of confronting adjacency with the tissue volume to be removed. When this position is reached, the positioning mode is terminated (footswitch 88b is released or button switch 57 is released), the arm/disarm tissue capture button or switch 56 or footswitch 88a is depressed momentarily, the LED above that switch as well as LED 98 are illuminated, and the system 10 enters an arm capture mode. During this mode, switches 57 and 88b are disabled. The start capture button or switch 58 or footswitch 88c is then depressed and continues to be depressed, the LED above switch 58 as well as LED 100 are illuminated, a capture mode commences, and the motor 160a (FIG. 3) turns on to advance the yoke assembly 180 forwardly for an interval of one half second during which time motor current is monitored to assure proper operation. As the yoke 180 engages the ears 138 and 140 of drive member 276, motor assembly 160 is turned off. The electrosurgical generator applies first boost, then normal cutting energy to the pursing cables 230–234 (FIG. 7) and following a one half second delay, motor assembly 160 is energized to start deployment of the capture component 200. During energization of pursing cables 230–234 the noted steady tone is provided from console 64. This capture mode continues until the capture component 200 orientation described in connection with FIG. 10 is reached. At that juncture, a forward stall condition is witnessed at motor 160a, forward energization of the motor assembly 160 is terminated and the motor is reversed to withdraw the transfer assembly 176 to its initial home position. LED 102 on console 64 as well as the corresponding LED output at array 60 are illuminated and the tone representing application of electrosurgical current is terminated. Delivery cannula 22 is removed from the patient, plug 148 is attached to vacuum connector 42 and connector 26 is rotated to permit removal of the disposable unit 16. Upon removal of the disposable unit, ears or tabs 138 and 140 may be manually retracted to engagement with the latch assembly 296 to permit capture component 200 to assume an orientation represented at FIG. 9 for tissue specimen access.

Electrosurgical energy is applied at the noted boost voltage level at the initiation of the procedure with respect to both the positioning mode and the capture mode or recommencement following any pause activity that occurs in conjunction with the release of fingerswitch 58 or footswitch 88c and the illumination of LED 104. The extent of this application is for a boost interval extending at least until the commencement of formation of an arc to permit cutting or for some predetermined boost interval based upon experience, for example, three eighths second.

Control over the cutting energy supplied from the electrosurgical generator to the pursing cables 230–234 is predicated, inter alia, upon a conventional design approach wherein the power developed must be effective to sustain an arc so as to cut while not causing excessive damage to tissue adjacent the cut, the instrument, or the recovered tissue specimen. With system 10, however, additional criteria arise. That active electrode manifested as the tissue encountering portions of cables 230–234 is changing in surface area extent during the procedure. It initially commences to be excited under boost voltage having a geometry somewhat resembling a point source. Then it increases in peripheral extent resembling a gradually expanding line source, whereupon it then returns to assume a geometry approaching a point source. Thus, the system 10 generally is involved with a cable-based variable performance requirement. Additionally, at the commencement of the procedure, the active electrode assembly, whether precursor electrodes or capture component cables, is embedded in tissue and boost voltage is called for during the noted boost interval to create a vapor and cause the commencement of an arc extending, for instance, between the cutting portions of cables 230–234 and the tissue being cut. In effect, it is this arc and not the cables per se that creates the cut. The active electrode portions merely slide within a vapor developed from adjacent tissue cell layers. Accordingly, the control must sustain the arc throughout the procedure.

Conventional electrosurgical generators are designed to perform in conjunction with an active electrode of fixed configuration or geometry such as a blade or rod. Development of a necessary cutting arc is achieved by the technique or experience of the surgeon who causes initial arc formation or creation by moving the active electrode toward the targeted tissue until the arc forms, for example, at about one mm spacing. Looking to FIGS. 11A and 11B, this technique is portrayed. A patient is depicted at 310 whose back is abuttingly engaged with a large dispersive electrode 312 which provides a return to an electrosurgical generator 314 as represented at line 316. Generator 314 feeds tissue cutting energy to an active electrode or electrosurgical scalpel 318 of fixed geometry as represented at line 320.

To achieve arc commencement, the electrosurgical generator output must confront an impedance of adequate range, for example, 1300 to 1500 ohms. This impedance is resistant in nature and comprises the resistance, $R_{tissue}$, exhibited by the body of the patient 310, as represented by the distance from B to C, the value ranging from about 300 ohms to about 500 ohms, in combination with the impedance or resistance developed by the active electrode spacing from tissue 322 of patient 310. FIG. 11B illustrates, in enlarged fashion, that spacing, $L_g$, as the distance from A to B. Looking to FIG. 12, this resistance, $R_{AB}$ is plotted at dashed lines 324 and 326 with respect to variations in the distance, $L_g$. Note that at values of $L_g$ greater than about 2 mm as shown at dashed line 324, the resistance $R_{AB}$ approaches infinity and no arc is developed as labeled. However, as the active electrode of fixed configuration approaches a distance, $L_g$ of about 1 mm, a resistance of about 500 ohms to about 1000 ohms is witnessed which, when combined with the resistance, $R_{tissue}$ (B to C) permits an arc to be formed as labeled. With the proper resistance, $R_{total}$, represented from A to C, the cutting arc will be sustained in accordance with the generalized expression: $R_{total} = R_{tissue}$ and $R_{arc}$. With the above arrangement, conventional electrosurgical generators are operated in conjunction with a fixed output power and a variable applied voltage. The output power levels thus are maintained within a safe range, for example, from about 80 watts to about 100 watts. Studies carried out with the instant system reveal that uniform electrothermal power is call for over a substantial tissue resistance range. Human fatty tissue exhibits high resistance while very dense tissue exhibits very low resistance. As a consequence, the system 10 should be capable of uniform performance over a load resistance range of from about 100 ohms to about 2000 ohms. That calls for a substantially constant power output characteristic.

The equivalent of the arc formation otherwise created by manual electrode spacing carried out with the technique of the surgeon is achieved with system 10 even though the active electrode initially and at the time of any restart is embedded in tissue with no initial spacing available. Application of the short term ($t_{boost}$) boost voltage ($V_{boost}$) causes a vaporization of the tissue cell structure adjacent the initially exposed and tissue embedded active portions of cables 230–234 or the precursor electrodes. This evokes the equivalent of an initial spacing to achieve requisite impedances for arc commencement. The interval of application of the boost voltage may be, as noted above, of minimal fixed duration, for example, about 500 milliseconds or less or may be defined by the creation of the arc following the application of this boost voltage. The impedance change, $R_{total}$, at the formation of the arc represents a quite abrupt alteration and results in a corresponding abrupt drop in output current flow. Accordingly, the formation of the arc may be detected readily to carry out boost voltage application termination.

Figure 13:
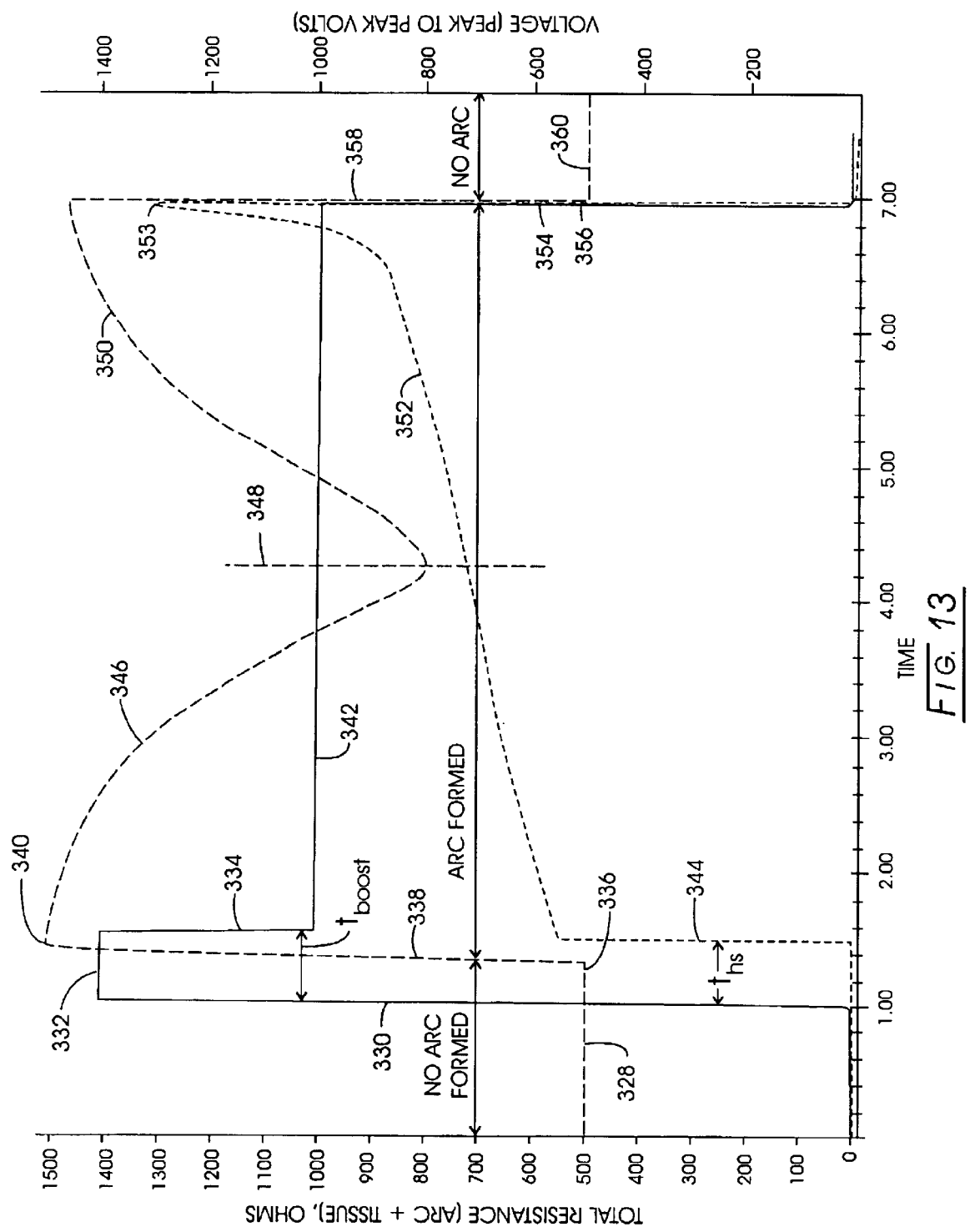
FIG. 13 is a graph relating time with applied voltage and total resistance for an electrosurgical system incorporating the electrosurgical generator of the invention.

Referring to FIG. 13, the performance of system 10 in connection with an experiment carried out using slab bacon and a capture maximum diametric extent of 10 millimeters is portrayed. The experiment utilized a generator exhibiting a constant voltage characteristic as described in copending U.S. application Ser. No. 09/904,412 (supra). In the figure, total resistance in terms of ohms, as computed, is plotted with respect to time. Additionally, applied, peak-to-peak voltage is plotted with respect to that time, and the current witnessed at d.c. motor 160a is plotted. At the commencement of the procedure, prior to the application of boost voltage, the total resistance was equal to the tissue resistance, $R_{tissue}$ as earlier described in connection with distance B-C in FIG. 11A. That 500 ohm level is represented at dashed line segment 328. Boost voltage was applied to the cable electrodes 230–234 to commence the boost interval at a boost voltage of 1400 volts peak-to-peak, as represented at line 330. This boost voltage was imposed for an interval, $T_{boost}$, as represented at line segment 332, of 500 milliseconds, whereupon the applied boost voltage abruptly dropped as represented at solid line segment 334. During the boost interval, following about 200 milliseconds, as represented at dashed line segment 336 and somewhat vertical dashed line segment 338, an arc was formed and total resistance abruptly elevated to about 1500 ohms at a point in time near the termination of the fixed boost interval. This arc formation occasioned the adding of about 1000 ohms of arc resistance to the tissue resistance as the value for $R_{total}$. As represented at line segment 334 the applied voltage was dropped to a normal cutting voltage level represented at horizontal solid line segment 342. This applied normal cutting voltage is seen to have been at a level of 1000 volts peak-to-peak. Essentially simultaneously, as represented at vertical dashed line segment 344, motor 160a was energized following a head start interval, $t_{hs}$ from the application of boost voltage. With the energization of motor assembly 160, the leafs 210–214 commenced to be extended as the cables 230–234 began to be played out toward a peripheral extent of maximum diameter. As this occurred, the length and consequent surface area of the cables engaged in active cutting of tissue expanded and the corresponding total resistance commenced to drop as represented by the dashed curve segment 346. As the maximum peripheral extent of the leaf tip portions and active cable cutting lengths reached the maximum value, as represented at vertical dashed line 348, total resistance for the cut voltage level reached a lowest value. At this juncture, applied current also reached a maximum value with a concomitant power increase.

As the time interval of the procedure continued beyond the time represented at vertical dashed line 348, the active surface area of cables 230–234 employed in cutting tissue reduced as forward contraction or pursing ensued and the effective cable length engaged in tissue cutting reduced. This reduction in active surface area evoked a total resistance increase as represented by the curved dashed line segment 350. During this interval, the d.c. motor current which commenced at line segment 344 gradually increased as represented at dashed line segment 352 until motor stall threshold was reached as represented at the current level 353, whereupon motor current was terminated as represented at dashed line segment 354. Simultaneously, normal cutting voltage was terminated abruptly as represented at dashed line segment 356. Following the procedure, the total resistance, $R_{total}$, returned to the value of the tissue resistance, $R_{tissue}$, as represented at line segments 358 and 360.

Figure 14:
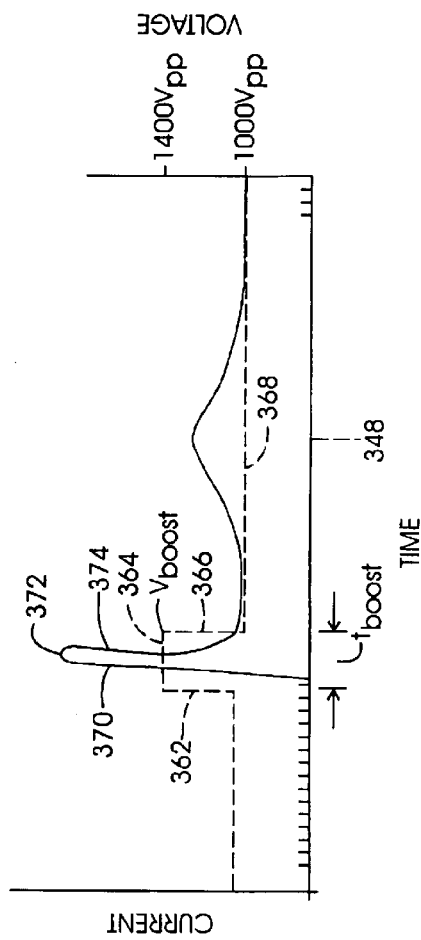
FIG. 14 is a graph showing current levels occurring during the operation of the instrument of FIG. 1.

Referring additionally to FIG. 14, a plot of current output and control timing occurring during the interval represented by the procedure carried out in connection with FIG. 13 is revealed. In the figure, the time of applying voltage, commencing at the noted boost level is represented by vertical dashed line segment 362. The voltage was applied at a boost level and continued as represented at horizontal dashed control line segment 364 and this boost voltage level terminated at the completion of a 500 millisecond boost interval as represented at vertical dashed line segment 366. Applied voltage then was retained at a constant voltage level represented at horizontal control line segment 368. During the application of boost voltage as represented at control line segments 362 and 364, current levels, encountering initial lower tissue impedance, abruptly rose as represented at curve segment 370 and was sustained at the peak level thereof as represented at 372 for an interval of about 200 milliseconds. At the termination of that interval, an arc developed to impose arc resistance occasioning an abrupt current drop represented at curved portion 372. It is during that 200 millisecond interval that the effective initial spacing is carried out by vaporization of tissue cells and the cutting arc is developed. The plot represented by these current levels also may be considered to correspond with power dissipation during the procedure. The current drop represented at curved segment 372 may be detected for purposes of terminating the boost voltage and thus established the boost interval in correspondence with arc formation.

Returning momentarily to FIG. 13, and recalling that with system 10, power applied from the electrosurgical generator is varied in accordance with the application of boost voltage and with the changing of the cable electrode geometry, for the example at hand, power dissipation may be evaluated. The commencement of the application of boost voltage is represented at line 330, a tissue resistance of 500 ohms having been encountered. Accordingly, until the arc was formed, under an applied boost voltage of 1400 volts peak-to-peak, a power dissipation of about 500 watts occurred. However, that power was produced in a highly constricted region for the very short interval occurring until the arc was formed as represented at dashed line 338, for an example, the interval of about 200 milliseconds discussed above. As soon as the arc was formed, as represented at dashed line 338, the impedance represented by the arc was added to the 500 ohm tissue impedance and the power dissipation dropped to about 167 watts which, although slightly high, remained only until the removal of boost voltage as represented at vertical line segment 334. Normal cutting voltage at 1000 volts peak-to-peak then ensued with a power dissipation of about 85 watts. However, now the expansion of the active electrodes commenced, power again rose as the total resistance dropped to about 800 ohms as the cable length enlarged and the maximum peripheral extent of the leading edge of the capture component 200 was reached as represented by dashed locator line 348. Accordingly, the power will have elevated from about 85 watts to about 159 watts. However, the 159 watt power value is one associated with a relatively widely disbursed line source electrode at its maximum linear extent. As pursing activity then ensued, that linear extent diminished toward a point value and power dissipation also diminished to again reach 85 watts at the termination of capture: As is apparent from the foregoing, it is possible to apply electrosurgical energy at the boost voltage level (e.g., 1100 volts, peak-to-peak) continuously throughout the procedure. In effect, the boost interval, $t_{boost}$ is extended to encompass the entire time of the procedure whether positioning with precursor electrodes or capturing with pursing cables. However, the consequence of so expanding the boost interval is the potential generation of excessive power during the biopsy procedure which results in artifacts evidencing greater depth of thermal injury to the biopsy specimen.

The boost voltage is selected within a range extending from about 1000 volts, peak-to-peak to about 2000 volts, peak to peak. Preferably, the boost voltage extends within a range from about 1200 volts, peak-to-peak to about 1500 volts, peak-to-peak. The boost interval will fill within a range of about 100 ms to about 1000 ms, and preferably within a range from about 250 ms to about 500 ms. At the termination of the boost interval, the electrosurgical energy is dropped to a normal cutting voltage level selected within a range extending from about 700 volts, peak-to-peak to about 1200 volts, peak-to-peak, and, preferably, within a range extending from about 800 volts, peak-to-peak, to about 1000 volts, peak-to-peak.

To achieve the above-discussed varying output performance required to sustain a cutting arc, over a quite broad range of tissue resistances the instant electrosurgical generator employs a constant power characteristic approach for non-boost cutting with complimentary voltage and power modes.

Referring to FIG. 15, a generalized block diagrammatic representation of the electrosurgical generation features and the control assembly incorporated with console 64 is presented. In general, the electrosurgical inputs to the pursing cables 230–234 and to the precursor electrodes of the instrument 12 are provided at an operating frequency of about 350 KHz. However the operating frequency may be selected to be in the range from about 250 KHz to about 10 MHz. For bipolar or quasi-bipolar instrument modalities as described in the above-noted U.S. Pat. No. 6,277,083 where the return electrode is located on the shaft or delivery cannula of the disposable component just proximal to the distal end or tip, the operating frequency may be as low as about 100 KHz. Different capture component maximum diametric values and associated lengthwise capture dimensions are based solely on the location of the cable stop 292 (FIGS. 9 and 10). With that arrangement, motor assembly 160 may perform in conjunction with a control which detects forward and rearward stall conditions as well as other load characteristic conditions which will represent fault states. In the figure, a conventional a.c. line input is represented at line 380 extending to an electromagnetic interference (EMI) filter represented at block 382. As represented at line 384 and symbol 386, the filtered output is passed through a fuse and into a front panel power on/off switch function represented at block 388. This switching function is described in connection with FIG. 1 at 82. Switch function 388 passes the filtered input to a power factor correcting (PFC) boost converter as represented at line 390 and block 392. Converter 392 rectifies the a.c. input to it to a d.c. current and boosts the d.c. voltage level to a regulated interim level while also creating a sinusoidal input current waveform which matches the sinusoidal input voltage waveform. This provides for a high power factor to reduce line current harmonics. Converter 392 provides the interim voltage as a 380 volt d.c. bus as represented at lines 394 and 396. The provision of the power factor correction feature at block 392 derives a variety of beneficial attributes. Less current is drawn as compared to conventional electrosurgical generators and the device may be employed universally with power utilities on a worldwide basis. Of additional importance, converter 392 derives a pre-regulated interim voltage at line 394 which permits an optimization of a next following link inverter in the electrosurgical generator function.

Line 396 functions to provide a d.c. input to a primary and auxiliary low voltage power supply (LVPS) as represented respectively at blocks 398 and 400 in connection with respective lines 402 and 404. Redundant low voltage power supplies are employed in view of the criticality of the control system associated with the instrument 12. In this regard, failure of a low voltage power supply otherwise occurring without such redundancy could result in shutting down the entire control system at a point in time during critical intervals in the procedure at hand.

The regulated 380 volts d.c. at lines 394 and 396 also is directed to a low voltage power supply represented at block 406 which functions to provide a very specific motor voltage to the motor drive circuitry as represented at line 408 and block 410. Control over the motor voltage, for example, at a level of around 10 volts is important, inasmuch as it is that voltage level which provides the proper rate of forward travel of the leafs and cable components of the capture component. In this regard, the deployment of the leafs and electrosurgically excited cable is measured in terms of millimeters per second. Should the drive imparted be too rapid, the excited cables will push against tissue and not cut properly which may result in both unwanted tissue necrosis and a false capture stall-based response on the part of the control system. Because the control system operates the motor drive 410 on the basis of detecting, for example, forward stall currents to determine the completion of a pursing activity, accommodation is made for anomalies in the motor drive caused by binding phenomena or the like wherein a forward stall would be detected by the control system before the capture component had been properly actuated. Because the rate of advance of the leafs and associated pursing cables is carefully controlled, it is known, for instance, that any excessive motor current detected before a certain initial test interval of time commencing with an initial motor activation would represent a drive malfunction. Reusable component 14 connector 68, referred to as a "Handle Connector" is represented in the instant figure at block 412 which is shown communicating motor drive inputs as represented by arrow 414 which is coupled with the motor drive function at block 410. Control to the motor drive represented at block 410 initially is provided from a control arrangement which includes control and drive boards as represented at block 416 and dual arrow 418.

Returning to line 394, the regulated 380 volts d.c. output of the converter 392 is introduced to a 100 KHz link inverter represented at block 420 which additionally is shown to be under the control of the control and drive circuit board function of block 416 as represented at dual arrow 422. That control is called upon to effect a constant power regulation of the electrosurgical output energy, achieving an arc-sustaining, non-oscillatory performance. The a.c. (square waveform) output of link inverter 420 is presented, as represented at line 424 to one side of an isolation transformer represented at block 426. Transformer 426 provides an output, as represented at line 428 which is rectified and filtered as represented at block 430 to develop a regulated d.c. link voltage at line 432 having a value of about 100 volts. The amplitude of the link voltage at line 432 is controlled with a circuit topology incorporating a high gain or rapidly responsive internal feedback loop in conjunction with a relatively low gain or slow external feedback loop. Line 432 is directed to two relay disconnects as represented at block 434. These relay disconnects are controlled from the control and drive circuit board 416 as represented by arrow 436. The d.c. link voltage then, as represented at line 438 is directed to an RF resonant inverter as represented at block 440. Inverter 440 operates in controlled relationship with the control and drive circuit boards represented at block 416 as indicated by arrow 442. It may be noted that by positioning the relay disconnects 434 before the RF inverter 440, in case of a fault or other anomaly, input to the RF inverter 440 itself can be disconnected. Inverter 440 is of a conventional resonant tank circuit variety which is tuned to a particular frequency. Its output peak-to-peak voltage amplitude is controlled by the amplitude of the d.c. link voltage.

The output of inverter 440 is directed, as represented by line 444 and block 446 to one side of a high voltage transformer which steps its amplitude from about 800 to about 1000 volts peak-to-peak from the 100 volt d.c. link voltage level. This output of the transformer stage 446 at line 448 is an electrosurgical cutting output which is, in effect, steered by series relays at a high voltage output stage represented at block 450 to either the precursor electrode input as represented at arrow 452 or to the capture component cables as represented at arrow 454. Control over the output stage 450 is indicated by arrow 456. Connector 80 of console 64 which is electrically associated with the dispersive electrode 70 is represented at block 458. The connector, in addition to providing a return to the high voltage output stage 450 as represented at line 460, is coupled with a patient circuit safety monitor (PCSM) which is represented at block 462. Monitor circuit 462 is coupled with each of the discrete electrodes 72 and 74 as represented at lines 464 and 466 and is controlled to provide fault data to the control and drive boards 416 as represented by arrow 468. As discussed in connection with return electrode 70 shown in FIG. 1, the present system operates in monopolar fashion and utilizes a dual component dispersive pad as a return electrode. The RE1 and RE2 leads represented at lines 464 and 466, in addition to providing a high voltage return, are utilized to output a high frequency current which is directed from one pad as at 72 to the other as at 74 to verify the tissue resistance between them. In this regard, the PCSM circuit 462 will apply about a 10 volt signal at 50 KHz to the two return electrode pads and verify proper resistance. Only upon such verification will the system permit the practitioner to continue the procedure by going into a ready mode. If the PCSM test is not met or passed, the system will not proceed and both visible and audible pulsed alarms are produced. PCSM circuit 462 also performs a self test at such time as the on/off switch represented at block 388 is actuated to an on state.

The front panel controls as described at console 64 in connection with FIG. 1 are represented at block 470. These controls, as represented at line 472 and block 474 are associated with a front panel circuit board which, in turn, as represented at line 476 is provided inputs and outputs from the control and drive boards represented at block 416. Both control and drive boards, additionally, receive inputs from footswitch 88 as represented at block 478 and switching line bus arrow 480. Inputs from switches 56–58 at reusable component 14 are represented at arrow 482, while outputs to the LED arrays as at 60 are represented at arrow 484. Finally, vacuum switch 51 is represented by a block with that same identifying numeration along with earlier described arrow 53 extending to block 416. Arrow 53 represents a two lead input.

Figure 16:
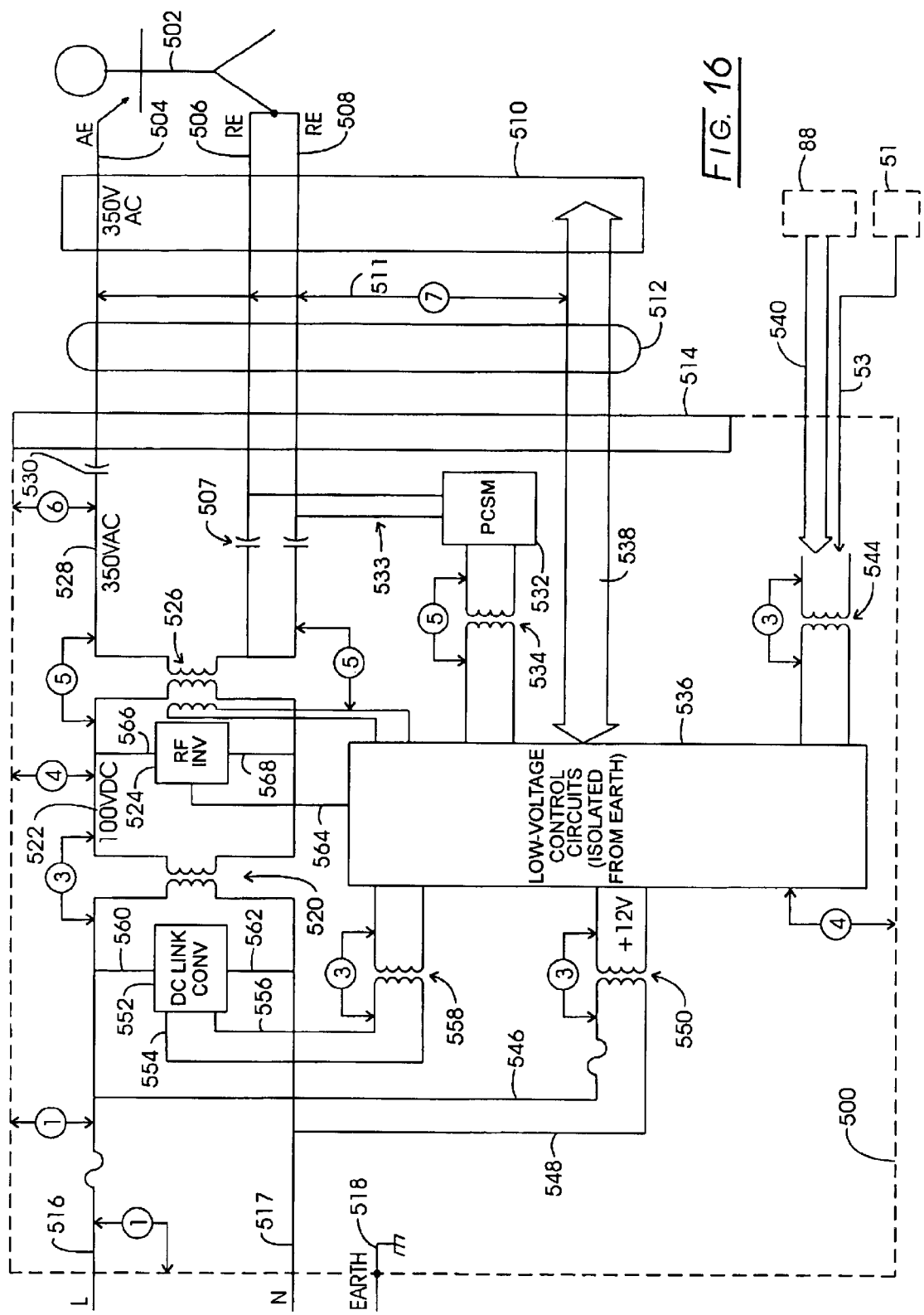
FIG. 16 is an insulation diagram for the electrosurgical generator shown in FIG. 15.

With the circuit arrangement thus described, a primary circuit is developed between the a.c. input at line 380 and the isolation transformer 426. From the output of isolation transformer 426, providing the noted d.c. link voltage, a secondary, lower voltage circuit is evolved. That secondary circuit extends to the high voltage transformer represented at block 446. From that circuit location, a high voltage circuit obtains with the system which develops the noted electrosurgical cutting signal. These three different regions are incorporated with different isolation barriers of the system. In this regard, some components fall within a safety extra low voltage circuit regime (SELV) while other circuits are completely isolated from potential contact. For medical devices which are going to be attached to a patient, concerns become more stringent for assuring that no current will flow from one device, for example, to another associated with the patient. Referring to FIG. 16, an isolation and insulation diagram is presented which may be associated with the system diagram in FIG. 15. In FIG. 16, encircled insulation codes 1 through 7 are located. These codes correspond respectively with the insulation types: BI, BOP, RI, RI, BI, RI, and OP. These insulation types are further identified as follows:

"OP"—Operational insulation;
"BOP"—Basic insulation between parts of opposite polarity;
"BI"—Basic insulation providing the first level of protection against electrical shock;
"RI"—Reinforced insulation.

Looking to FIG. 16, dashed boundary 500 represents the conductive enclosure of console 64. A patient is symbolically represented at 502 who will be contacted by the active electrode (AE) as represented at arrow 504 and return electrodes (RE) as represented at lines 506 and 508. The nonconductive housing of the instrument 12 is represented at block 510 and the cable assembly including cable 62 is represented at symbol 512. A nonconductive front panel of the console 64 is represented at block 514.

A.c. input to the control assembly and electrosurgical generator is represented by line, neutral and earth lines shown respectively at lines 516–518. This commences the earlier-noted primary circuitry. Note that insulation code 1 stands between line 516 and the chassis 500. Next, the primary circuit extends to a transformer function represented symbolically at 520 carrying a boundary code 3 which is a high voltage insulation boundary. Then a transition to about a 100 volt d.c. link voltage represented at line 522 occurs with an insulation boundary code 4. The system then extends through the RF inverter represented at block 524 and described earlier at 440 in FIG. 15 to a high voltage transforming function represented generally at 526 with an insulation barrier code 5. This transforming function has been described in connection with block 446 of FIG. 15. The transforming function as represented at 526 develops a high voltage output as represented at line 528 in conjunction with an insulation code 6. Next, the system extends through blocking capacitors represented at 530, front panel 514, cable assembly 512 to instrument 12 as represented at 510 and the active electrodes 504 which will make contact with the patient 502. The return electrodes as represented at lines 506 and 508 are seen extending through coupling capacitor pair 507 to the output of the transforming function 526, as well as being associated at line pair 533 with the PCSM circuit now shown at block 532 and earlier-described in connection with block 462 of FIG. 15. That circuit is further isolated at insulation barrier 5 and an isolating transforming function represented generally at 534 before having operational association with the low voltage control circuits represented at block 536. These low voltage control circuits as at 536 are shown insulated with respect to the chassis represented at dashed boundary 500 at code 4. Inputs to and outputs from this low voltage control are represented by bi-directional arrow 538 extending across front panel 514, cable assembly 512 and the instrument 12 as represented at 510. However, the footswitch function as described in connection with FIG. 1 at 88 and shown in dashed block form in conjunction with bus arrow 540 in the instant figure is depicted as being isolated from the low voltage control circuits 536 at transforming function 544 which is associated with code 3 insulation. Similarly, vacuum switch 51 is identified by a dashed block along with arrow 53 which extends to transforming function 592. Note that the +12 volt d.c. input to the low voltage control circuits 536 as represented at lines 546 and 548 is isolated as represented at transforming function 550 which is associated with code 3 insulation. The d.c. link converter function represented at block 552 at lines 554 and 556 is isolated from the low voltage control circuits at block 536 as represented by transforming function 558 and in conjunction with insulation code 3. Note that the link converter circuit 552 is coupled between line input at line 516 and neutral input at line 517 by respective lines 560 and 562. Control output to the RF inverter function at block 524 is shown at line 564 extending from the low voltage control circuits 536. It may be recalled that that function now shown at block 524 performs in conjunction with the lower level d.c. link voltages as represented at lines 566 and 568. Finally, note that a code 7 insulation as associated with arrows 511 is provided at the interface between the cable assembly represented at symbol 512 and the instrument 12 as represented at block 510.

Console 64 houses a sequence of circuit boards, certain of which have been identified in connection with FIG. 15 as control and drive boards and a front panel board. In general, these circuit boards are daughter boards to a principal or mother board identified as a main power circuit board.

Figure 17A:
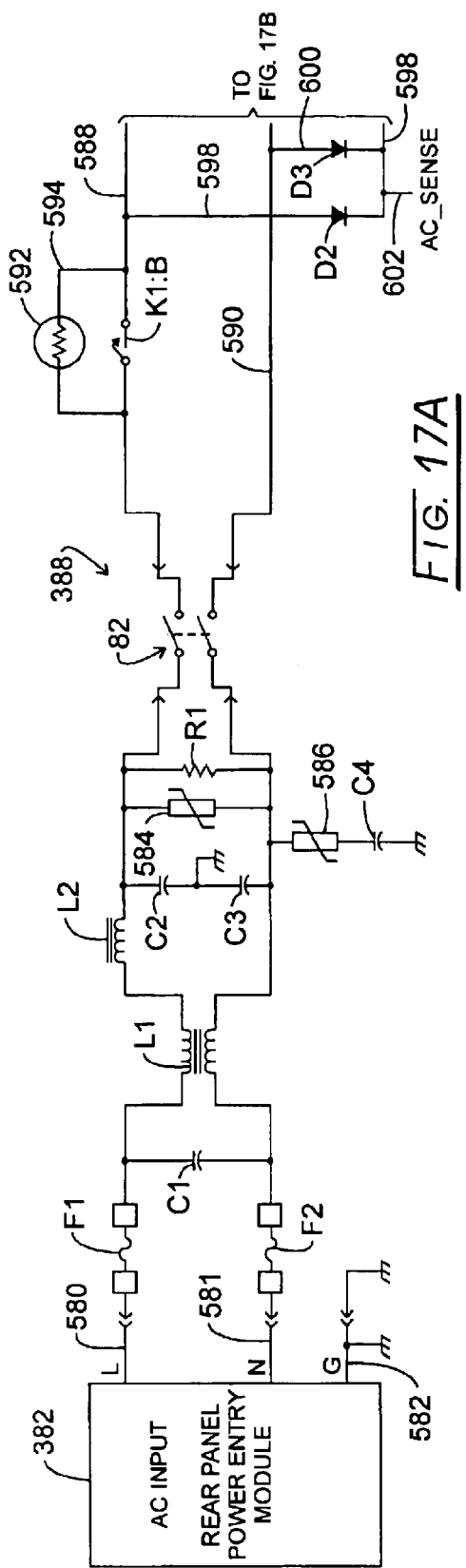
FIGS. 17A and 17B combine as labeled thereon to provide a schematic circuit diagram showing the EMI filter, front panel switch, and PFC boost converter components shown in block form in FIG. 15.
Figure 18:
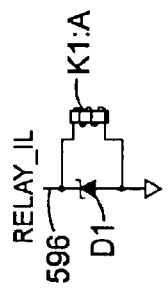
FIG. 18 is an electrical schematic diagram showing a relay solenoid component employed with contact shown in FIG. 17A.
Figure 17B:
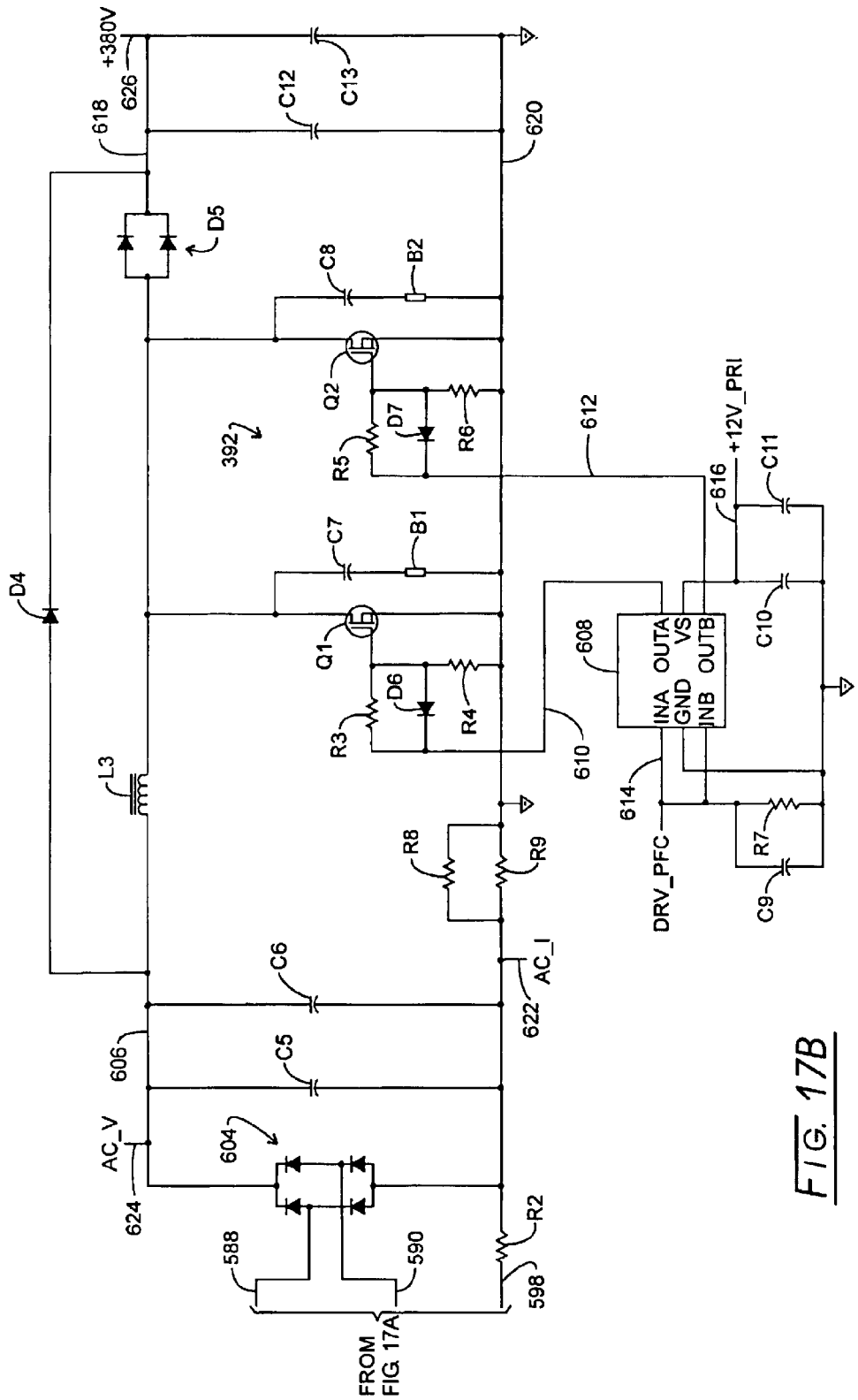

The discussion now turns to the functions and components associated with the power circuit board. These components are described in connection with FIGS. 17A, 17B–23A, 23B, and 23C. FIGS. 17A and 17B should be considered in the manner labeled thereon. Looking to FIG. 17A, line input is provided to the earlier-described EMI filter 382 which numeration is reproduced in the present figure. Referred to as a "rear panel power entry module", the device 382 may be provided as a line filter with a.c. Inlet type 5110.1033.3, marketed by Schurter, Inc., of 79343 Endigen, GE. The filtered output from device 382 is present at line, neutral and ground line shown respectively at lines 580–582. Lines 580 and 581 are directed to fuses F1 and F2, as well as to components providing additional EMI filtering. Those components include capacitors C1–C3, a dual inductor form of device L1, inductor L2 and a discharge resistor R1. Further protection is provided by varistors 584 and 586, the latter component being coupled through capacitor C4 to ground. The filtered input then extends across the front panel power switch represented at 82 in FIG. 1 and at block 388 in FIG. 15, those identifying numbers being reproduced in the instant figure. Closure of switch 82 provides line and neutral energization at respective lines 588 and 590. In-rush current occasioned by the presence of relatively large hold-up capacitors in the system is controlled by a negative temperature coefficient thermistor 592 coupled in line 594 so as to extend across the contact K1:B of a relay K1 within line 588. Looking momentarily to FIG. 18, the solenoid actuating components of that relay K1 are revealed at K1:A. This solenoid actuator performs in conjunction with a RELAY_IL control input at line 596. Inductive spikes occasioned by energization and de-energization of solenoid K1:A are controlled by a diode D1. Returning to FIG. 17A, diode D2 within line 598 extending from line 598 and diode D3 in line 600 extending from line 590 function to derive a rectified AC_SENSE signal at line 602 extending from line 598. This signal is derived in conjunction with a resistor R2 within line 598 as seen in FIG. 17B. The AC_SENSE signal at line 602 is utilized to derive an indication to the control assembly that the input is of high enough voltage amplitude to operate the system.

FIG. 17B shows that lines 588 and 590 extend to a rectifier network represented generally at 604 which derives a haversine waveform at lines 598 and 606. Small filter capacitors C5 and C6 extend between these lines. Rectifier 604 may be provided as a type D25XB60 marketed by Schindengen America, Inc. of Westlake Village, Calif. The full wave rectified a.c. voltage is applied across the latter capacitors to the input of the earlier-described power factor correction boost converter represented generally at 392 and comprised of transistors Q1 and Q2 which perform in conjunction with principal components including inductor L3, diode D4 and diode pair D5 under the switching control of a controller driven driver represented at block 608. In this regard, note that control line 610 extends from output A of the driver 608 to the gate of transistor Q1 to effect switching control thereof in conjunction with peripheral components including resistors R3 and R4, diode D6, capacitor C7 and bead B1. In similar fashion, output B of driver 608 carries out switching control at the gate of transistor Q2 via line 612 in conjunction with resistors R5 and R6, diode D7, capacitor C8 and bead B2. Device 608 is controlled by a DRV_PFC signal at input line 614, receives primary circuit low voltage input, +12V_PRI at line 616 and is configured in conjunction with capacitors C9–C11 and resistor R7. Device 608 may be provided, for example, as a BiCMOS/DMOS buffer/driver/MOSFET driver type MIC4424 marketed by Micrel, Inc. of San Jose, Calif. The earlier described 380 volt interim voltage is provided across lines 618 and 620 and, thus, across very large holdup capacitors C12 and C13 which function to protect the system against vagaries such as transient sags and surges induced at the line input. In effect, the capacitors provide energy storage to "ride through" such anomalies. The regulated 380V interim voltage is tapped at line 626.

FIG. 17B also reveals an A.C. current sense signal (AC_I) at line 622 extending from line 598 which is associated with parallel resistors R8 and R9. That signal is employed in connection with power factor control (FIG. 24B) in conjunction with a corresponding a.c. voltage sense signal (AC_V) at line 624 extending from line 606. The circuitry thus far described represents the earlier-discussed primary circuit which, with respect to FIG. 17B, performs with a primary power supply as presented at line 616 in conjunction with primary circuit which subsequently extends to a secondary circuit upon passing the primary or isolation transformer function described in connection with FIG. 15 at block 426.

Figure 19:
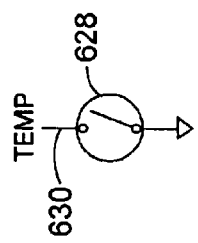
FIG. 19 is an electrical schematic diagram of a temperature responsive component employed with the console shown in FIG. 1.

Looking to FIG. 19, an over-temperature switch, which is mounted upon a heat sink within the console 64 is represented at 628. Where an over-temperature condition exists, then a low logic true signal, TEMP is generated at line 630.

Figure 20:
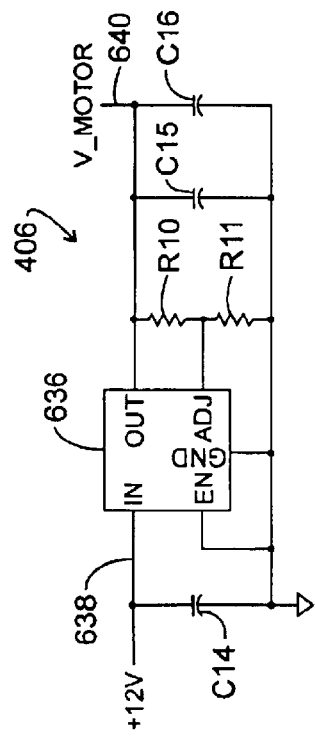
FIG. 20 is an electrical schematic diagram of a power supply dedicated to provide input power to a motor contained in the reusable housing of the instrument as shown in FIG. 2.

Looking to FIG. 20, the regulator for developing the important motor voltage input is shown at 636. Device 636 may be provided, for example, as a type LM2941 Low Dropout Adjustable Regulator marketed by National Semiconductor Corp., of Sunnyvale, Calif. The device functions in connection with +12V input at line 638 and is configured in conjunction with capacitors C14–C16 and resistors R10 and R11 to provide a motor voltage output, V_MOTOR at line 640.

Figure 21:
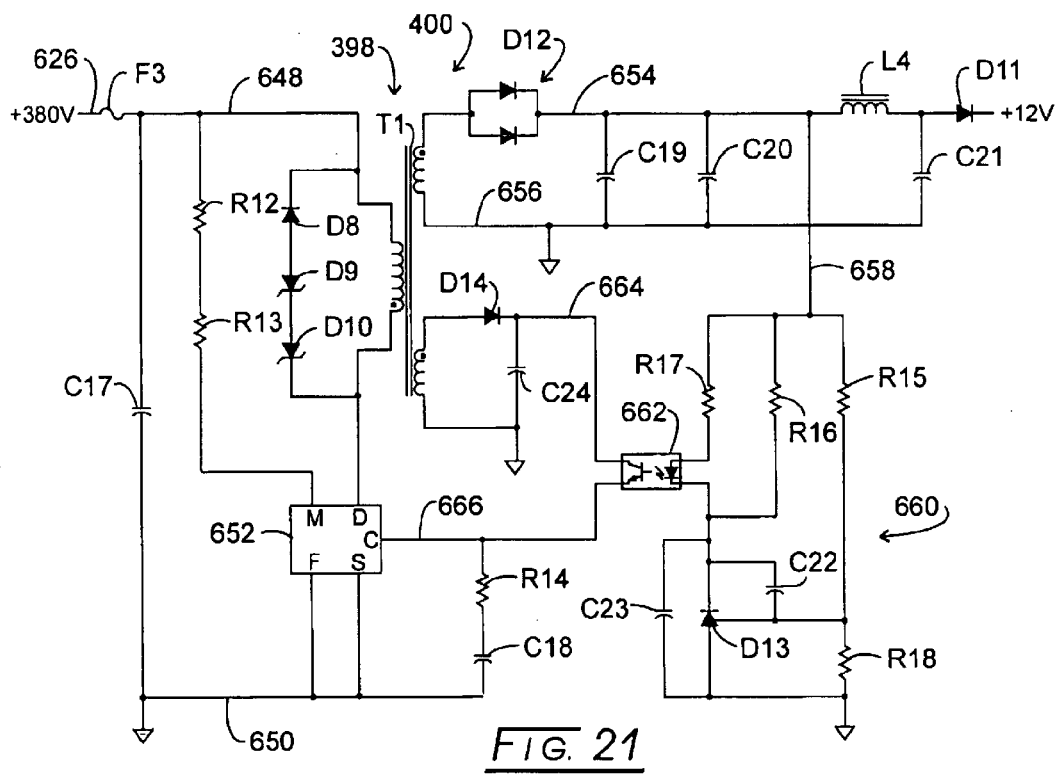
FIG. 21 is an electrical schematic diagram of one low voltage power supply shown in block diagrammatic form in FIG. 15.

As discussed in connection with FIG. 15, the present control system includes two low voltage power supplies as described in connection with blocks 398 and 400. These redundant power supplies provide outputs which are logically ORed. FIG. 21 reveals the topology of these identical circuits as identified by the above-dual numeration. The low voltage power supply circuit taps the +380V high voltage output at line 626 which incorporates a fuse F3 and is directed via line 648 to one end of the primary side of a step-down transformer T1. The opposite end of this primary side is coupled to primary circuit ground ultimately provided from line 650. Switched control input to the input side of transformer T1 is carried out by a control device 652 which is configured in conjunction with capacitors C17 and C18, resistors R12–R14 and diodes D8–D10. Switching control 652 is referred to as a "smart power switch" which incorporates regulating circuitries including a power transistor along with pulse width modulation (PWM) controls and the like. The device may be provided as a type TOP234Y Integrated Off Line Switcher marketed by Power Integrations, Inc., of Sunnyvale, Calif. Transformer T1 provides galvanic isolation and its secondary is tapped at lines 654 and 656 to present a +12V low power supply to ORing diode D11. That output is rectified by diode pair D12 and filtered by inductor L4 and capacitors C19–C21.

Feedback control to the switching controller 652 is derived at the secondary side of transformer T1 at line 658 which extends to a secondary side input network represented generally at 660 and comprised of resistors R15–R18, capacitors C22 and C23 and diode D13. Network 660 provides a voltage proportional signal to the input diode of an opto-isolator 662. The output of opto-isolator 662 returns a feedback signal representing the voltage level at line 658 to the primary circuit side of the power supply by modulating an input from the connection with a second portion of the secondary side of transformer T1 incorporating line 664, diode D14 and capacitor C24. This signal is modulated at the opto-isolator 662 and directed via line 666 to the control input of controller 652. Accordingly, an isolated feedback control arrangement is provided.

Figure 22:
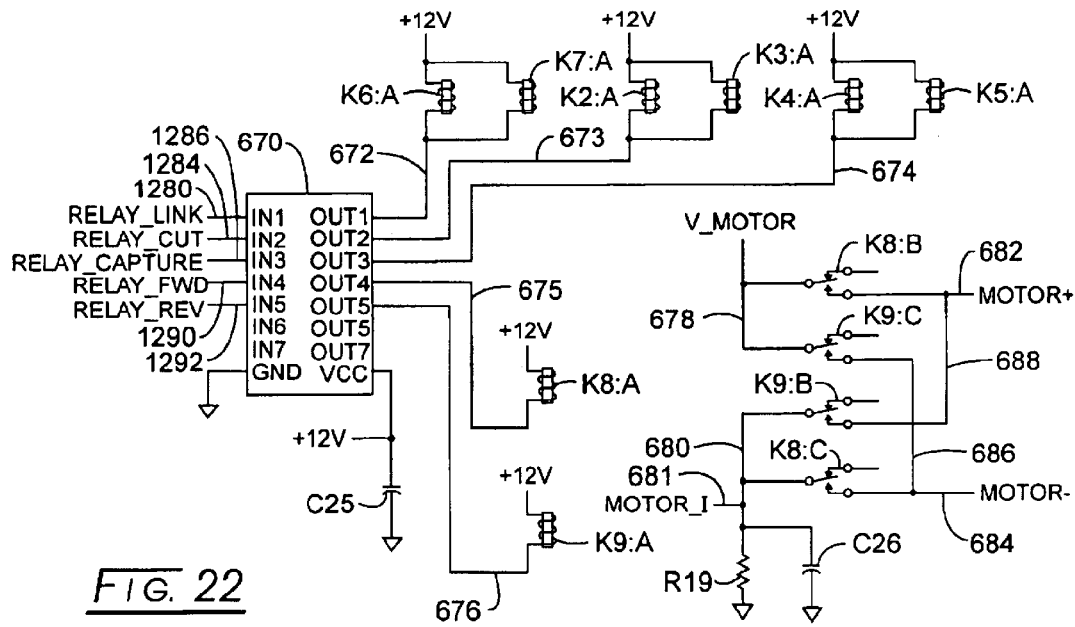
FIG. 22 is an electrical schematic diagram of a motor drive shown in block schematic form in FIG. 15 and further showing the solenoid components of relays employed with the invention.

A variety of relays are employed for the purpose of motor activation, safety and control over the dual electrosurgical cutting sequences and the like. Referring to FIG. 22, a relay controller 670 is illustrated in conjunction with a sequence of five relay input control signals at its IN1–IN5 input terminals. Those input signals are developed from a programmable logic device (PLD) described later herein. Controller 670 may be provided as a type ULN2004 High-Voltage, High Current Darlington Array, marketed by Micro Systems, Inc. of Worcester, Mass. Device 670 is configured with +12V input and capacitor C25 and functions to provide drive outputs to the solenoid components of a sequence of relays. In this regard, relay solenoid components K6:A and K7:A are connected with terminal OUT1 and line 672, thence to +12V. Solenoid components K2:A and K3:A are coupled between output terminal OUT2 by line 673 and thence to +12V. Relay solenoid components K4:A and K5:A are coupled with output terminal OUT3 by line 674 and thence to +12V. Relay solenoid K8:A is coupled to output terminal OUT4 via line 675 and thence to +12V, and relay solenoid K9:A is coupled with terminal OUT5 of device 670 via line 676 and thence to +12V. The latter two solenoid actuators function to selectively actuate or drive respective dual relay contacts K8:B, K8:C and K9:C, K9:B to provide directional control to motor 160a. The inputs to the contacts K8:B, K9:B and K9:C are coupled with the earlier-described V_MOTOR input at line 678 and the corresponding inputs of contacts K9:B and K8:C are coupled with line 680. Line 680 is seen to be coupled to secondary circuit ground in conjunction with resistor R19 and filter capacitor C26. When relay K8:A is energized, contact K8:B functions to apply the V_MOTOR signal to line 682, while contacts K8:C connect line 684 to secondary ground through line 680. Correspondingly, when relay K9:A is energized, the signal V_MOTOR is applied to line 684 through line 686 and line 682 is coupled to secondary ground through line 688, relay contacts K9:B and line 680. Accordingly, forward and reverse drive is made available for actuating motor 160a. Motor current is monitored at lines 680 and 681 to provide a signal, "MOTOR_I", used to evaluate instantaneous motor current draw or load characteristic.

Figure 23A:
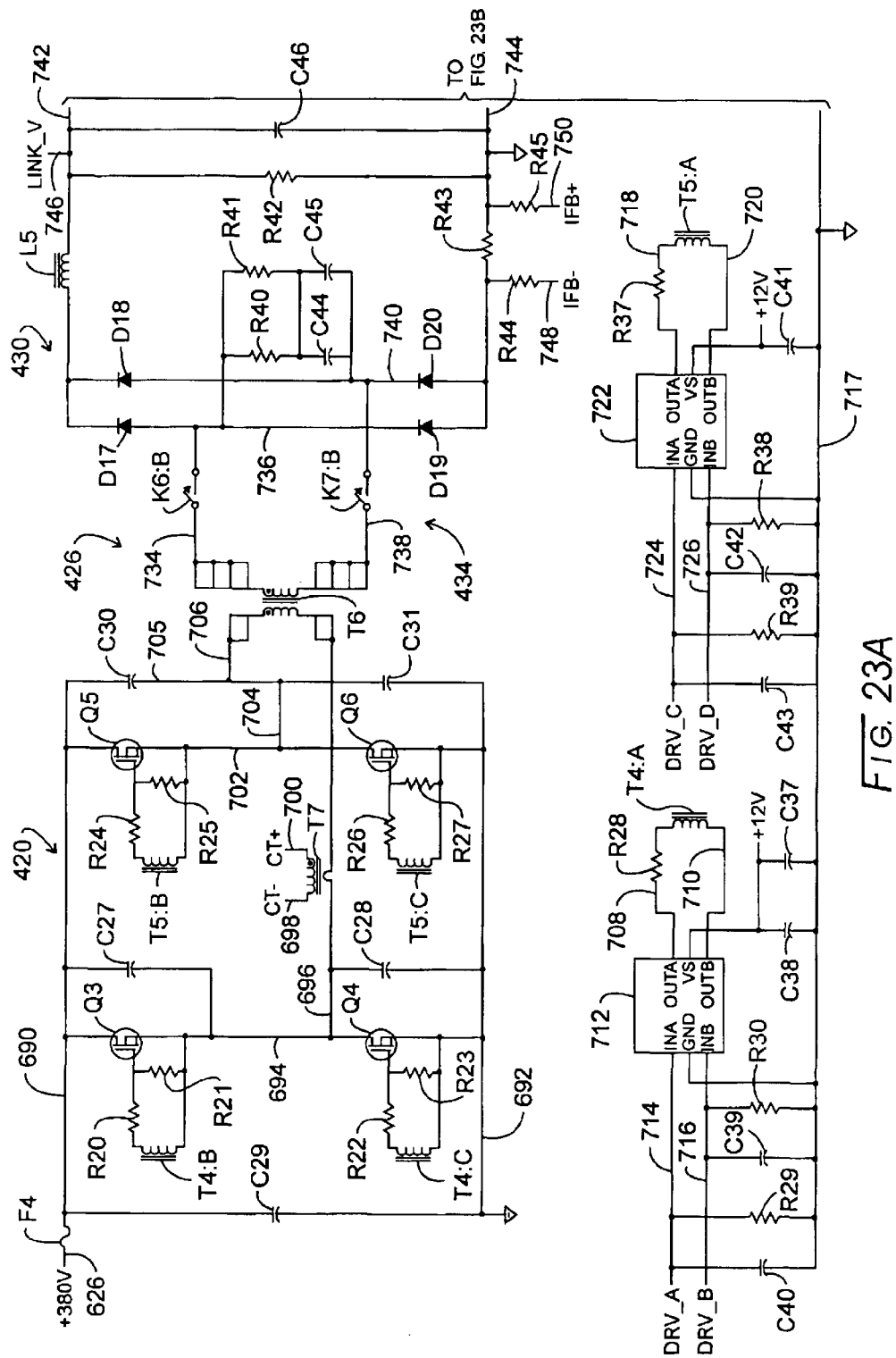

FIGS. 23A and 23B should be considered together in accordance with the labeling thereon. Referring to FIG. 23A, a more detailed illustration of the 100 KHz link inverter described at block 420 in connection with FIG. 15 is revealed. The inverter is represented in general with that same numeration. Inverter 420 is implemented in a unique manner for electrosurgical applications, inasmuch as it is a "resonant transition phase shift inverter" which evokes what may be termed "soft" switching, driving the primary side of main isolation transformer T6, earlier-described at block 426 in FIG. 15. The transformer additionally is identified in general with that earlier numeration. Inverter 420 is formed with MOSFET transistors Q3–Q6. Of these transistors, transistors Q3 and Q4 are switched in complimentary fashion as are transistors Q5 and Q6. Because the switching transistors perform in the primary circuit domain in conjunction with the pre-regulated 380V derived from earlier-described line 626 and now presented at line 690, it is necessary to provide for a primary to secondary circuit isolation between the control input to the inverter 420 and the switching components of it. In this regard, transistor pairs Q3, Q4 and Q5, Q6 are coupled between lines 690 containing fuse F4 and line 692 which is coupled to primary ground. Transistors Q3 and Q4 are seen to be coupled within line 694, transistor Q3 being configured in conjunction with resistors R20 and R21 and capacitor C27. Correspondingly, complimentary transistor Q4 is implemented with resistors R22 and R23 and capacitor C28. A capacitor C29 is coupled between lines 690 and 692. Coupled to the gate of transistor Q3 is the secondary side of a pulse transformer T4:B and similarly coupled to the gate of transistor Q4 is the secondary side, T4:C of the same pulse transformer. A node is established between transistors Q3 and Q4 at line 696 which extends, in turn, to one end of the primary side of isolation transformer T6. Transistors Q3–Q6 may be provided as type IRF460 Repetitive Avalanche and e/v/dt Rated HEXFET® transistors marketed by International Rectifier, Inc. of El Segundo, Calif. Transformer T6 was described at block 426 in connection with FIG. 15 and is represented in general by that same number in the instant figure. The pulsed output at line 696 is monitored for control purposes by a current transformer T7 to provide control output signals CT− at line 698 and CT+ at line 700. Those signals are employed in conjunction with the phase shift resonant controller which controls inverter 420 as described later herein in connection with FIG. 26.

Transistor Q5 is configured in conjunction with the resistors R24 and R25 and capacitor C30. Similarly, transistor Q6 is configured with resistors R26 and R27 and capacitor C31.

Transistors Q5 and Q6 are connected in series within line 702, and the node between them is tapped at lines 704–706 which are coupled to another end of the primary side of isolation transformer T6. Complimentary transistors Q5 and Q6 are switched by inputs into transformer secondary sides T5:B and T5:C respectively.

Now looking to the primary side controlling inputs to these three-winding transformers, the primary side, T4:A of the transformer T4 is shown coupled through line 708 incorporating resistor R28 and line 710 to the output terminals, OUTA and OUTB of a driver component 712. Device 712 may be provided, for example, as a type MIC4424. Performing in conjunction with a +12V input and configured with capacitors C37–C40 and resistors R29 and R30, the device responds to inputs, DRV_A and DRV_B derived from the drive circuit board and coupled to driver 712 via respective lines 714 and 716. Capacitors C37–C40 and resistors R29 and R30 are seen to be coupled to secondary ground line 717.

The corresponding switching to transistors Q5 and Q6 is derived from the primary side of three-winding transformer T5 at T5:A. That primary side is coupled via line 718, incorporating resistor R37, and line 720 to the output terminals, OUTA and OUTB of a driver component 722 which also may be provided as a type MIC4424. Device 722 performs in conjunction with +12V and is configured with capacitors C41–C43 and resistors R38 and R39 to respond to control inputs DRV_C and DRV_D provided at respective lines 724 and 726 to carry out complimentary switching of the transistors Q5 and Q6. Those inputs also are derived by the controller for inverter 420 as described in connection with FIG. 26.

Looking momentarily to FIG. 23C, a schematic representation of the squarewave generated, for example, at the switching node between transistors Q5 and Q6 is represented in general at 728. The corresponding squarewave generated at the switching node intermediate transistors Q3 and Q4 is represented schematically at 730. When these squarewaves are in phase, there is no voltage difference between them and thus no voltage is impressed across the isolation transformer T6. However, the voltage output of the isolation transformer T6 is controlled by modulating the phase between the squarewave arrays 728 and 730 to evolve a resultant squarewave, for example, as symbolically represented at the right of the resultant wave 732.

Returning to FIG. 23A, as this inverter switching is carried out, the secondary side output of transformer T6 is directed to each half of a full wave bridge rectifier described earlier at block 430 in connection with FIG. 15 comprised of diodes D17–D20. In what are referred to as "resonant transitions", the capacitors C30 and C31 as well as capacitors C27 and C28 combine with the leakage inductance of transformer T6 to create soft switching resonant transitions on the two switch nodes. Thus transistor pairs Q3 and Q4 and Q5 and Q6 switch in a very "soft" manner with low stress and with high efficiency.

The secondary side of isolation transformer T6 is seen to be coupled via line 734 incorporating relay contacts K6:B to line 736 carrying diodes D17 and D19. Correspondingly, the opposite end of the secondary side of transformer T6 is coupled via line 738 having relay contacts K7:B to line 740 which, in turn, incorporates bridge diodes D18 and D20. The relays correspond with block 434 described in connection with FIG. 15. In this regard, the system can be switched off and on at the stepped down link voltage levels. Relay contacts K6:B and K7:B are selectively actuated from the relay solenoids described respectively at K6:A and K7:A in FIG. 22. The full wave rectifier formed with diodes D17–D19 is implemented in combination with resistors R40 and R41 and capacitors C44 and C45 to derive the d.c. link voltage across lines 742 and 744. Filtering of the rectified d.c. link voltage further is provided by inductor L5 and capacitor C46. Capacitor C46 carries the d.c. link voltage which is monitored at line 746 as a "LINK_V" signal which is used for fast or high gain controller feedback and other purposes. Resistors R43 at line 744, R44 at line 748 and R45 at line 750 are employed to derive the current-proportional monitor signals, IFB− and IFB+ employed by the noted inverter 420 controller as described in connection with FIG. 26. The controller employs the signals at line 746, 748 and 750, inter alia, to control the link voltage level with respect to both the peak-to-peak normal cutting voltages as applied to the precursor electrode and the capture component cables and for the purpose of providing a boost level voltage at the commencement of any cutting activity. Such control advantageously is carried out with the phase shifting control feature of the network 420.

The voltage amplitude regulating link voltage across capacitor C46 is applied to the RF inverter as described earlier at block 440 in connection with FIG. 15 and represented by the same general numeration in FIG. 23B. RF inverter 440 is configured as a resonant tank circuit comprised of capacitors C47 and C48 along with an inductor L6. In this regard, note that capacitors C47 and C48 are positioned within lines 752 and 754 between lines 742 and 756. Similarly, inductor L6 is coupled by line 758 and 760 between lines 742 and 756. To excite or induce oscillation in the tank circuit, four MOSFET transistors Q7–Q10 are selectively gated to couple line 756 with d.c. link voltage line 742. The gate of transistor Q7 is configured with resistors R46 and R47 and line 762 which extends to one output OUTA of a driver or buffer 764. Driver 764 is configured with capacitors C49 and C50, resistor R48 and +12V and responds to a DRV_RF signal at its input line 766 to carry out gating. The device 764 may be provided as a type MIC4424. The second output, OUTB, of device 764 is coupled via line 768 with the gate of transistor Q8. That coupling is configured in conjunction with resistors R49 and R50.

In similar fashion, the gate of transistor Q9 is configured with line 770 and resistors R51 and R52. Line 770 extends to the OUTA output terminal of a driver or buffer 772. Driver 772 is configured with capacitors C51–C53 and +12V and receives a control input, DRV_RF at its input line 774. Device 772 also may be of the noted type MIC4424. The second output terminal, OUTB, of device 772 is coupled via line 776 with the gate of transistor Q10 which is configured in conjunction with resistors R54 and R55. A SYNC signal is generated from line 756 at line 778 which is configured in conjunction with resistors R56–R58 and capacitor C54.

The stable frequency sinewave generated by RF inverter 420 is applied to the primary side of the step-up transformer T3 described earlier in connection with block 426 in FIG. 15. The transformer is additionally identified with that same numeration in the instant figure. A stepped-up output from transformer T3 is provided at lines 780 and 782. An inductor L7 at active electrode line 780 provides a smoothing of the sinewave output. The output at line 780 is directed through relay contacts K2:B and K3:B and coupling capacitor C55 to derive the cutting output, HV_PRECURSOR which is directed to the precursor electrodes and corresponds with line 452 described in connection with FIG. 15. Correspondingly, active electrode line 784, extending from line 780, carries relay contacts K4:B and K5:B and extends in combination with coupling capacitor C56 to provide the electrosurgical cutting output, HV_CAPTURE which is supplied to the pursing cables 230–234. Line 784 corresponds with line 454 earlier described in connection with FIG. 15. Relay contacts K2:B–K5:B are controlled from the solenoid components described above in connection with FIG. 22 and function as components of output stage 450 as described in connection with FIG. 15. The latter identifying numeration reappears in the instant figure. Return line 782 is coupled with the corresponding two pads or surfaces 72 and 74 of the return electrode 70 (FIG. 1). In this regard, the line is coupled to one pad of the return electrode through coupling capacitor C57. The earlier-noted PCSM test described in conjunction with block 462 is carried out in conjunction with the signal RE2 at line 786. Line 786 corresponds with line 466 described in connection with FIG. 15. Line 782 is coupled with line 788 and coupling capacitor C58 to provide a second return for the opposite return electrode pad. Line 788 is coupled with line 790 which extends to PCSM circuit 528 as discussed in connection with FIG. 15. The noted signal identification, RE1 reappears in the latter figure in connection with line 464. A current monitoring transformer T9 is coupled with line 782 to develop the high voltage current monitoring signals, HV_I− and HV_I+ at respective lines 794 and 796. Similarly, a voltage monitoring transformer T10 is connected within line 798 between active electrode and return electrode line 780 and 782. The secondary side of transistor T10 is configured in conjunction with rectifier-defining diodes D23–D26, resistor R59 and capacitor C59 to provide a voltage monitoring signal, HV_V at line 800. A treated version of that signal provides an outer loop low gain program input to the control of link inverter 420.

Figure 24B:
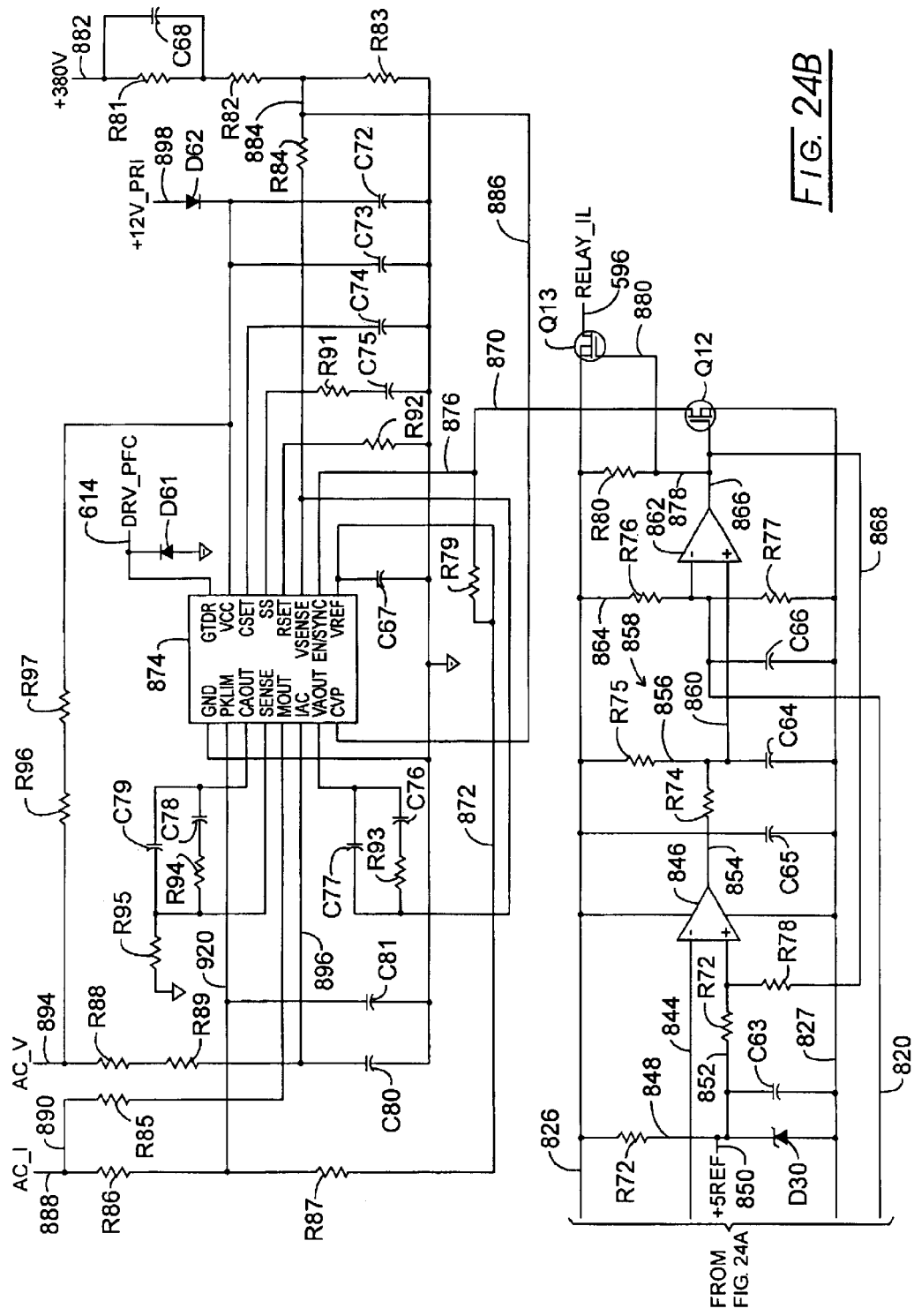

FIGS. 24A and 24B should be considered together in the manner labeled thereon. These figures are concerned with components mounted on the earlier-described drive board which carries, inter alia, monitoring and control functions for the PFC boost converter 392 which has been discussed in connection with FIGS. 15 and 17B.

Looking initially to FIG. 24A, the pre-regulated 380 volt interim voltage level present at capacitors C12 and C13 has been described in connection with a monitoring signal, +380V at a monitoring line 626. Line 626 reappears in the instant figure along with that voltage level which is divided by resistor grouping R60–R62, filtered at capacitor C60 and delivered via line 802 to one input of a comparator 804. The reference input to comparator 804 is delivered from +5REF at line 806 which incorporates level adjusting resistors R63 and R64 and is coupled to the opposite input of comparator 804 at line 808. When the 380V input at line 626 is of proper amplitude, comparator 804 provides an output at line 810 incorporating resistor R65 which is submitted to an R-C timing network represented generally at 812 and comprised of resistor R66 and capacitor C61 within line 814. The time constant selected for network 812 accommodates for any line vagaries or the like. Accordingly, the slightly delayed signal then is introduced via line 816 to one input of a buffer 818, the opposite input to which is provided from line 820. The output of buffer 818 at line 822 extends to line 824 which is coupled through resistor R67 to +12V primary power input at line 826. Line 824 is coupled via line 828 to the gate of transistor Q11. Transistor Q11 is connected within line 830 incorporating resistor R68 between line 826 carrying the noted +12V_PRI and primary ground at line 827. Transistor Q11 is turned off in response to a logic true low at line 828 to, in turn, energize the diode of an opto-isolator 834 via lines 836 and 838. The resultant output from the opto-isolator 834 couples the low logic true high voltage ok signal, HVOK, at line 840 to ground via line 842. This signal is utilized as an enabling input by controller circuitry in the lower voltage secondary side of the system as described, for example, in connection with FIG. 26.

The 380V d.c. output itself is not enabled until assurance is made that the a.c. input as described at line 380 in connection with FIG. 15 is at a proper level. A sensing of this value was provided from line 602 as described in connection with FIG. 17A. Line 602 reappears in the instant figure as providing the AC_SENSE signal in conjunction with resistors R69–R70 and capacitor C62, the line then being coupled with line 827 and tapped at line 844. A resistor R71 is incorporated between lines 844 and 827.

Looking to FIG. 24B, line 844 is seen to extend to one input of a comparator 846. The opposite input to comparator 846 is +5REF which is derived at line 848, intermediate resistor R72 and diode D30 at reference line 850. The reference (+5REF) at line 848 is tapped at line 852 incorporating resistor R73 and coupled through filtering capacitor C63 to line 827. Line 844, carrying the adjusted AC_SENSE signal, extends to the opposite input of comparator 846, and in the presence of an appropriate voltage level, an output is provided by comparator 846 at line 854. Line 854 incorporates resistor R74 and extends to line 856 wherein the output is subjected to the time constant established by resistor R75 and capacitor C64. The output from that R-C network represented generally at 858 then is directed via line 860 to one input of a comparator-buffer 862. The opposite input to buffer 862 is derived from line 820 extending to line 864, in turn, incorporating resistors R76 and R77. Filter capacitors are shown at C65 and C66 and the low logic true output of comparator 862 at line 866 is seen to be directed to the gate of transistor Q12. Transistor Q12 normally is held on from line 868 incorporating resistor R78. The source of transistor Q12 is connected with line 827 and its drain is coupled with line 870 incorporating resistor R79. Line 870 is coupled, in turn, to line 872 which is filtered by capacitor C67 and extends to the VREF terminal of the controller 874 for the PFC boost converter described in conjunction with block 392 in FIG. 15. Note that line 870 further is coupled via line 876 to the enabling input terminal, EN/SYNC of device 874. Thus, transistor Q12 turns off in the presence of an AC_SENSE signal of proper amplitude to enable controller 874 by application of a voltage from line 872, resistor R79 and line 876. The device 874 may be provided as a type LT1248 power factor controller marketed by Linear Technology Corp., of Milpitas, Calif.

Line 866 additionally is seen to be coupled via line 878 and resistor R80 to line 826 which extends, in turn, to the source of transistor Q13. The gate of transistor Q13 is coupled to line 878 by line 880. Accordingly, the low true signal at line 866 functions additionally to turn on transistor Q13 providing a solenoid energizing signal at line. 596. In this regard, the signal at line 596 provides a RELAY_IL signal which, in turn, functions to energize the relay solenoid K1:A described in conjunction with FIG. 18. That relay closes the contacts K:B to shunt varistor 592 (FIG. 17A) which had been active to avoid in-rush currents.

Controller 874 functions to derive the control input, DRV_PFC applied to line 614 of driver device 608 described in connection with FIG. 17B. Line 614 is protected by diode D61. Device 874 performs in conjunction with a sensing of the 380V level output provided from line 626 described in connection with FIG. 24B; the sensing of a.c. current, AC_I as described in connection with line 622 in FIG. 17B; and a.c. voltage, AC_V, as described in connection with line 624 in FIG. 17B. 380V monitoring is represented at line 882 in the instant figure which incorporates resistors R81–R83 and capacitors C68. As thus adjusted, the voltage signal level then is introduced via line 884 incorporating resistor R84 to the voltage sense terminal (VSENSE) of controller 874. This signal level at line 884 also is extended via line 886 to the CVP terminal of device 874. The a.c. current level signal AC_I, is provided from line 888 and is derived from line 622 as described in conjunction with FIG. 17B. This signal at line 888 is seen to extend via line 890 and resistor R85 to the MOUT terminal of controller 874. Line 888 also incorporates a resistor R86 and extends to line 892 which, in turn, extends to the PKLIM terminal of controller 874. Line 872 is seen to extend with resistor R87 to line 892. The a.c. voltage signal, AC_V, is provided from line 894 and was derived at line 624 as described in connection with FIG. 17B. Line 894 is seen to incorporate resistors R88 and R89 and extends to line 896 which, in turn, is coupled with the IAC terminal of controller 874. Controller 874 performs in conjunction with the primary circuit power supply, +12V_PRI as shown introduced from line 898 incorporating diode D62. The device further is configured in conjunction with capacitor C72–C81 and resistors R91–R97.

As noted earlier herein the power factor connection developed in association with controller 874 not only permits the electrosurgical generator to be used universally with diverse worldwide utility line inputs, but also derives a pre-regulated interim voltage output which permits an optimization of the link inverter stage carrying out the constant power-based control permitting generation of a sustained cutting arc in the presence of an active electrode exhibiting a dynamic surface area or geometry and in conjunction with substantially expansive range of tissue load resistances.

Looking to FIG. 25, the low voltage primary circuit power floating bias supply is depicted. The 380V d.c. level as described in connection with line 626 in FIG. 17B is tapped as represented at line 900 incorporating fuse F5 and filtered by capacitor C85. Line 900 extends to line 902 incorporating diodes D63 and D64 and extending to the (Drain) terminal of a regulator 904 which may be provided as a type TOP221P Three-terminal Off-line PWM Switch marketed by Power Integrations, Inc., of Sunnyvale, Calif. Component 904 is referred to as a "smart power device", combining a power transistor and a pulse width modulation (PWM) control circuit. Its source terminals are seen coupled to ground in conjunction with line 906. Line 902 is connected across the primary side of a step-down transformer T12 and asserts a chopped input thereto under the control of device 904. The secondary side of transformer T12 is connected at line 908 and diode D65 to line 910 incorporating rectifying diodes D66 and D67 and coupled via resistor R98 to the C (Control) input of device 904. This serves as a feedback to device 904. The primary circuit power supply, +12V_PRI is then presented through resistor R99. Filtering capacitors are provided as represented at C86–C88.

Figure 26:
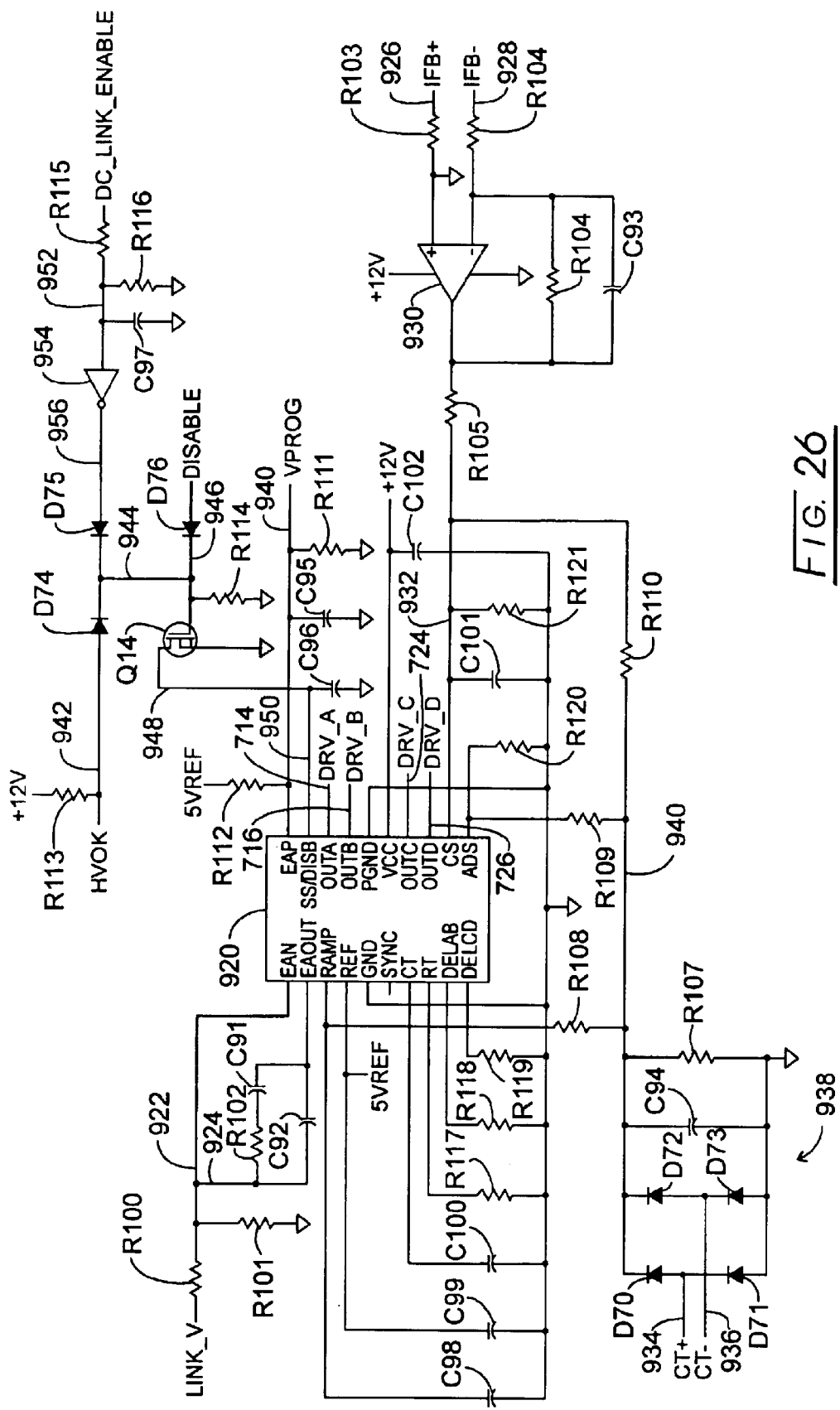
FIG. 26 is an electrical schematic diagram of a control circuit for providing phase shift resonant transition control.

Also located upon the above-noted drive board is the resonant transition control integrated circuit which develops the DRV_A through DRV_D control signals which are submitted to the inverter 420 as described in conjunction with FIG. 23A. Referring to FIG. 26, this controller is shown at 920, extending from which the noted drive signals are identified in conjunction with lines 714, 716, 724, and 726 as are repeated from FIG. 23A. Controller 920 may be provided as a type UCC3895 BiCMOS Advanced Phase Shift PWM Controller marketed by Unitrobe Corp., of Merrimack, N.H. The value of link voltage, LINK_V is submitted to the EAN and EAOUT terminals of device 920 from respective lines 922 and 924 which are configured in combination with resistors R100–R102 and capacitors C91 and C92. Line 922 corresponds with line 746 earlier-described in connection with FIG. 23A. This link voltage input at resistor R100 represents an inner, relatively fast or high gain control feedback loop to the link voltage controller 920, which performs, inter alia, in conjunction with an outer feedback loop program control which is comparatively retarded or slow or of a low-gain, low bandwidth nature. Link voltage current related signals IFB– and IFB+ are applied respectively from lines 926 and 928 incorporating resistors R103 and R104 to the inputs of a type LP1215 amplifier 930 which is configured in conjunction with resistors R105 and R106 and capacitor C93. The signals at lines 926 and 928 correspond with respective lines 750 and 748 described in conjunction with FIG. 23A. The output of amplifier 930 is provided at line 932 to the CS terminal of device 920.

Inverter 420 current signals, CT+ and CT–, are submitted via respective lines 934 and 946 to rectifying diode pairs D70, D71 and D72, D73 configured within a network represented generally at 938 including capacitors C94 and resistor R107. Lines 934 and 936 correspond with respective lines 700 and 698 described in connection with FIG. 23A. From network 938, corresponding signals are submitted via line 940 and resistor R108 to the RAMP terminal of device 920. Similarly, the signal is submitted via resistor R109 to the ADS terminal and through resistor R110 to line 932 and the CS terminal of device 920. The system elected link voltage as well as its resultant control in deriving a constant system output power is determined by a signal identified as "VPROG" (FIG. 27A) which is submitted via line 940 to the EAP terminal of device 920. Line 940 is configured in conjunction with resistor R111 and capacitor C95 and is coupled through pull-up resistor R112 to 5VREF, the latter reference voltage having been described in conjunction with FIG. 24B. As noted above, an outer feedback control loop, ultimately responsive to the level of system output voltage is combined with a high gain inner loop. This arrangement permits a constant power-based control accommodating the otherwise unstable oscillative tendencies posed by negative dynamic impedance of the required cutting arc as well as the impedance variation exhibited by the cables when operating in a capture mode. Accordingly, the outer feedback loop signal, VPROG applied at line 940 is programmed to device 920 in a very slow manner by selecting a relatively high capacitance value for capacitor C95, for example, 4.7 microfarads, evolving a time constant of about 35 milliseconds. This low gain, low bandwidth, slow or retarded response achieves a stable, constant power control over the RF inverter 440 output.

Device 920 also is selectively enabled or disabled in response to three signal inputs. One of those signal inputs is the earlier-described active low or logic low true HVOK signal generated from interim voltage responsive optoisolator 834 described in conjunction with FIG. 24A. This signal, HVOK, is seen introduced via line 942 which is coupled to +12V through pull-up resistor R113. Line 942 corresponds with line 840 of FIG. 24A and extends through steering diode D74 and lines 944 and 946 to the gate of MOSFET transistor Q14. Line 946 is coupled through resistor R114 to ground and the source and drain terminals of transistor Q14 are seen coupled between ground and lines 948 and 950. Line 950 extends to the soft start/disable terminal of device 920. Line 948 extends to ground through capacitor C96. Accordingly, when the signal at line 942 is a logic high value, representing an inadequate interim voltage level, then transistor Q14 is turned-on to bring line 950 to a logic low condition. This disables device 920 until such time as a logic true low condition occurs at line 942, whereupon transistor Q14 turns off to remove the low signal at line 950 and permit the internal circuitry of device 920 to effect its enablement.

As the practitioner actuates the energize position switch 57 on instrument 12, or footswitch 88b, a high voltage output is called for to energize the precursor electrodes. Before that condition occurs, the d.c. link voltage must be created. The PLD-based control system thus provides a logic high true DC_LINK_ENABLE input as shown at line 952 and incorporating resistor R115 and configured in conjunction with filter resistor R116 and filter capacitor C97. Line 952 extends to an inverter buffer 954 having an output at line 956 extending through steering diode D75 to line 944. Thus lines 956, 944 and 946 are maintained at a logic high level to turn on transistor Q14 and effect disablement of device 920 until line 952 assumes a high logic level upon enabling command, DC_LINK_ENABLE from the PLD-based control. Accordingly, in the absence of an appropriate link enable signal or an HVOK signal, device 920 will not provide a link control. Device 954 may be provided as a type CD40106B CMOS Schmitt trigger marketed by Texas Instruments, Inc., of Dallas, Tex. Use of such a component takes advantage of its filtering hysteresis characteristic.

A detected d.c. link overvoltage fault condition will derive a logic or active high true "DISABLE" signal (see FIG. 39) which is presented at line 946 through steering diode D76. Accordingly, if such a fault arises requiring that the system be shut down in the absence of a BOOST-MASK signal (FIG. 27A), it is at this location through diode D76 that such shut down activity takes place by turning on transistor Q14. Device 920 is seen to be further configured in conjunction with capacitors C98–C102 and resistors R117–R121 and may be provided as a type UCC3895 BiCMOS Advanced Phase Shift PWM Controller marketed by Unitrode Corp. of Merrimack, N.H.

Figures 27A, 27B:
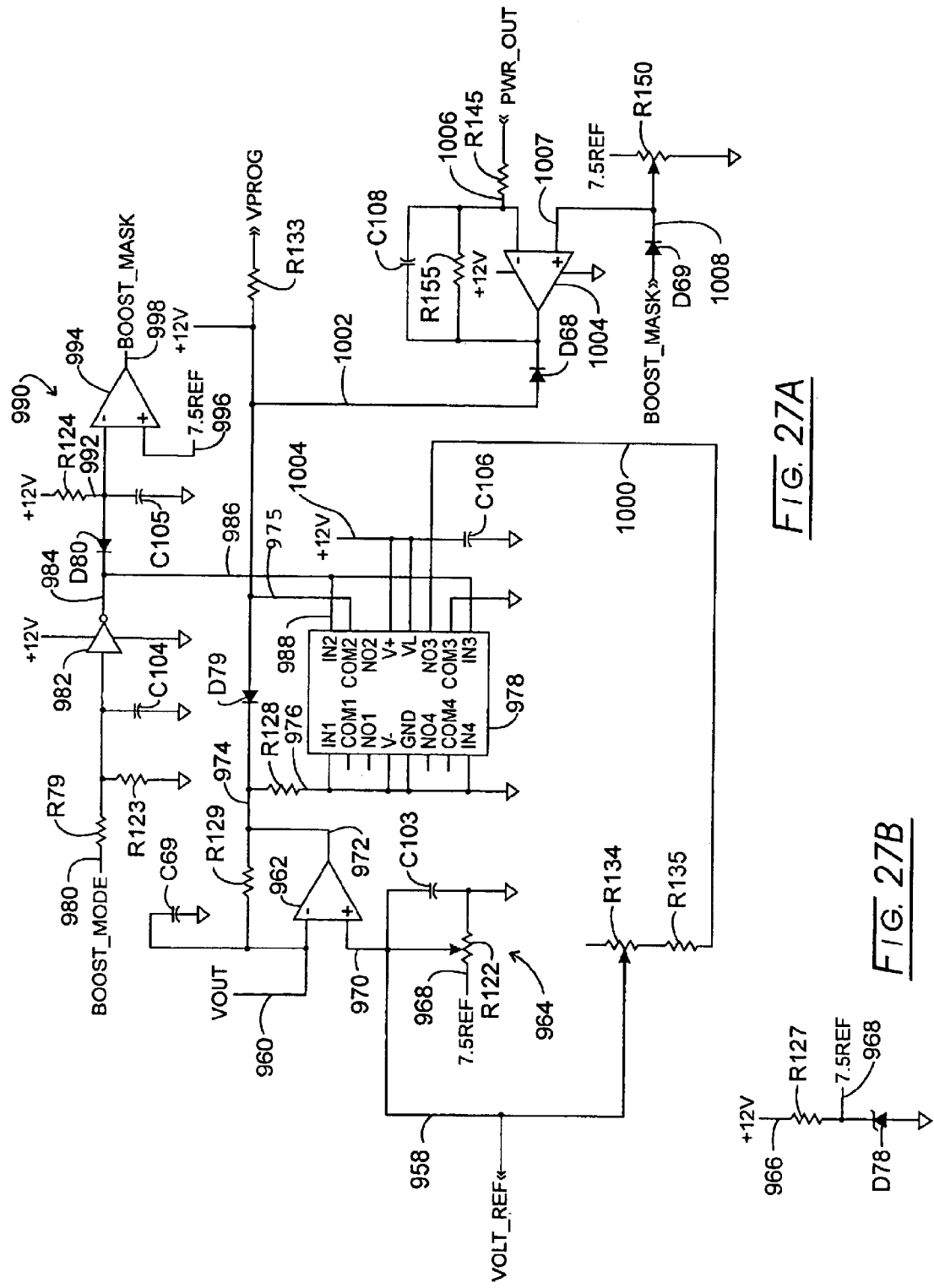
FIG. 27A is an electrical schematic diagram of a control circuit for adjusting d.c. link voltage.
FIG. 27B is an electrical schematic diagram of a reference voltage deriving circuit.

Referring to FIG. 27A, the control system output voltage outer loop monitoring circuit feature carried at a drive circuit board is illustrated. The high voltage output monitoring signal described in FIG. 23B as HV_V at line 800 is filtered as described in conjunction with FIG. 36 to provide the signal, VOUT which is introduced to line 960. Line 960 extends to one input of a voltage mode error amplifier 962. The reference input to device 962 is derived from a potentiometer represented generally at 964 incorporating resistor component R122 and a capacitor C103. Resistor component R122 is connected with a 7.5V reference input.

Looking momentarily to FIG. 27B, the derivation of that reference is illustrated. In the figure, line 966 incorporating resistor R127 and diode D78 is tapped to provide the 7.5REF signal at line 968 which reappears in FIG. 27A. Returning to FIG. 27A, a wiper arm extended input to device 962 is represented at line 970. Line 970 is coupled to line 958 to provide the signal, VOLT_REF. The output of amplifier 962 at line 972 represents an output voltage mode control signal which is directed to line 974 and thence through line 976 and resistor R128 to the IN1, V–, GND, and IN4 terminals of an analog switch device 978. Switch 978 may be provided as a type MAX4665 analog switch, marketed by Maxim Integrated Products, of Sunnyvale, Calif. Line 974 extends from input line 960 and is tapped at line 975 leading to the COM2 terminal of switch 978. The line incorporates resistor R129 along with steering diode D79, is filtered at capacitor C69 and extends to resistor R133 to provide the program output, VPROG when performing in a voltage mode. During that mode, diode D79 is forward biased. The voltage mode dominates at high load resistances above about 1200–1500 ohms. Note that voltage reference line 958 further is coupled to the wiper arm of a potentiometer incorporating resistor component R134 and resistor R135. A line 1000 couples resistor R135 to the NO3 terminal of switching device 978. Normally, that terminal is shorted to ground permitting adjustment of the normal voltage control mode.

Switch 978 responds to a logic high true or active "BOOST_MODE" signal generated from the control board PLD which is shown presented at line 980. It may be recalled that the boost mode provides for increasing the output voltage and, correspondingly, the power output of the precursor electrode and the pursing cables for about three eighth second or less at any start-up or restart. Line 980 is configured in conjunction with resistors R122 and R123 and capacitor C104 and extends to the input of a buffer-inverter 982. Device 982 may be provided as a type CD40106B Schmitt trigger (supra). Accordingly, the logic high true signal at line 980 is inverted to a logic low at line 984 and is directed via lines 986 and 988 to the IN2 and IN3 terminals of analog switch 978 to create a boost mode of performance.

The boost mode signal at lines 986 and 988 causes terminal NO3 of device 978 to open to add voltage to line 970 extending to amplifier 962. Steering diode D79 remains forward biased and the boost voltage signal of line 974 becomes VPROG.

Because the control assembly, inter alia, includes a d.c. link over-voltage fault condition, it is necessary to simultaneously develop a "BOOST_MASK" signal to overcome a false fault condition during a boost voltage mode. Accordingly, line 984 is seen to incorporate a steering diode D80 which is positioned forwardly of an RC network shown generally at 990 and comprised of resistor R124 and capacitor C105 extending within line 992 between +12V and secondary ground. Network 990 provides an input to the negative terminal of a comparator 994 to establish a normally logic low at its output line 998. The opposite input to device 994 at line 996 carries the 7.5REF signal described in conjunction with FIG. 27B. Boost mask comparator 994 provides a logic high true BOOST_MASK output at line 998 upon the occurrence of a boost mode establishing logic low condition at line 984. The BOOST_MASK active high output at line 998 is present during the occurrence of the BOOST_MODE command. As a safety feature, however, following the termination of the BOOST_MODE command signal, the logic high BOOST_MASK condition at line 998 will persist for about the time constant of RC network 990. In this regard, upon the assumption of an active low condition at line 984, capacitor C105 immediately discharges. At the termination of the boost mode, diode D80 is back-biased and capacitor C105 is gradually charged through resistor R123 to ultimately establish a voltage level causing boost mask comparator 994 to revert its output to a logic low level removing the BOOST_MASK signal.

In the boost mode, power is increased by a factor of two. Accordingly, the link voltage may be increased in consequence of VPROG by the square root of two, power being proportional to the square of voltage. In general, the boost voltage level will be greater than the normal cutting voltage level by a factor within a range from about 1.2 to about 1.5. Device 978 further is configured with +12V source and a capacitor C110 at line 1004 and may be provided as a type MAX 4465, 5 ohm, SPST, CMOS Analog Switch marketed by Maxim Integrated Products of Sunnyvale, Calif.

Figure 27C:
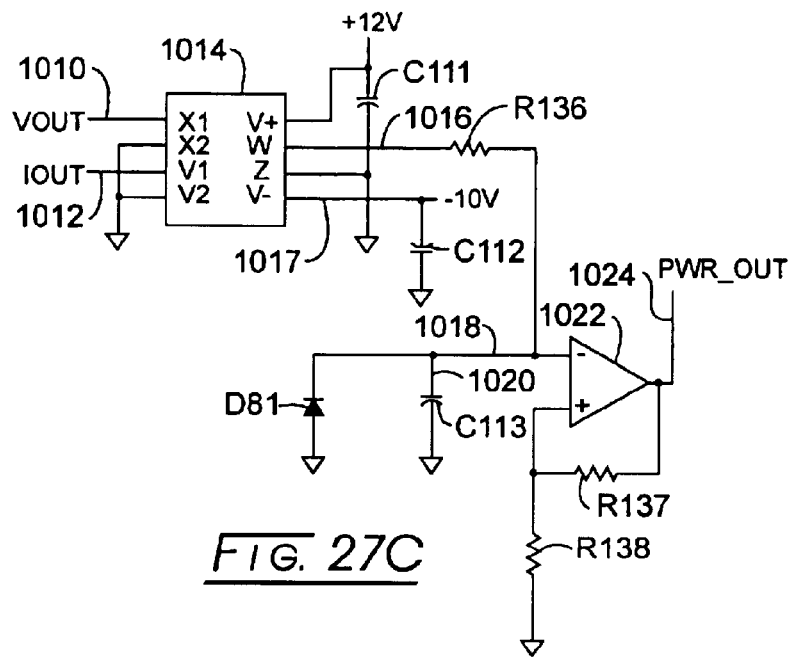
FIG. 27C is an electrical schematic diagram of a multiplier circuit for deriving an output power monitor signal.

Referring to FIG. 27C, a control system power derivation circuit feature carried by the drive board is illustrated. The circuit is multipurpose, being employed as a monitor to determine the presence of any excessive power, and also is employed as a power monitoring circuit for establishing the level of link voltage control signal, VPROG for low load resistances such that the system maintains a substantially constant power characteristic over an lower level impedance range, i.e., it operates in a power mode.

Overall power is determined by a monitoring of the output voltage and output current to derive signals VOUT and IOUT for presentation at respective lines 1010 and 1012 extending to a solid state multiplier 1014. Device 1014 may be provided, for example, as a type AB633JN Analog Multiplier marketed by Analog Devices, Inc., of Norwood, Mass. Multiplier 1014 is configured in conjunction with +12V and −10V power supply inputs as well as capacitors C11 and C112. Forming a component of the power derivation network, the product output of multiplier 1014 at line 1016 is applied to an integrating resistor R136. Line 1016 further extends to lines 1018 and 1020, the latter line incorporating an integrating capacitor C113. Line 1018 extends to a diode D81 and to the input of an amplifier 1022. With the arrangement shown, power is, in effect, computed in accordance with conventional expression:

$$P = \frac{1}{T} \int vi \, dt$$

Thus, capacitor C113 carries a monitored power signal proportional to output power. That signal is fed to amplifier stage 1022 which is configured with resistor R137 and R138 to double the amplitude of the signal. This provides a power value signal utilized by the system at line 1024 identified as "PWR_OUT" to monitor output power conditions (see FIG. 37) and to participate in the formation of VPROG for power mode performance.

Now looking to the monitored output power-based control participation in developing d.c. link voltage control, VPROG, it may be observed that line 974 also receives an input from line 1002. Line 1002 extends through a steering diode D68 which compliments or is ORed with diode D79 and is at the output of an error amplifier 1004. Amplifier 1004 is implemented with resistor R155 and capacitor C108 and the negative input thereto receives the earlier-described PWR_OUT monitor output through input resistor R145 at line 1006. It may be recalled that the latter signal was developed at line 1024 as described in conjunction with FIG. 27C. The opposite or reference input to error amplifier 1004 is presented at line 1007 from potentiometer R150 coupled between earlier described 7.5 REF and ground. With the arrangement, as lower tissue resistances are encountered with resultant higher currents and lower voltages, control over the development of VPROG will be from amplifier 1004 and a forward biased diode D68. At the higher voltages and lower current extant in the voltage mode, diode D68 will be reverse biased. However, in the presence of the BOOST_MASK signals generated at line 998, then as represented at line 1008 and diode D69, amplifier 1004 will be overridden to a high output voltage, reverse biasing diode D68 and the signal VPROG will be dominated by the BOOST_MODE signal.

Figure 27D:
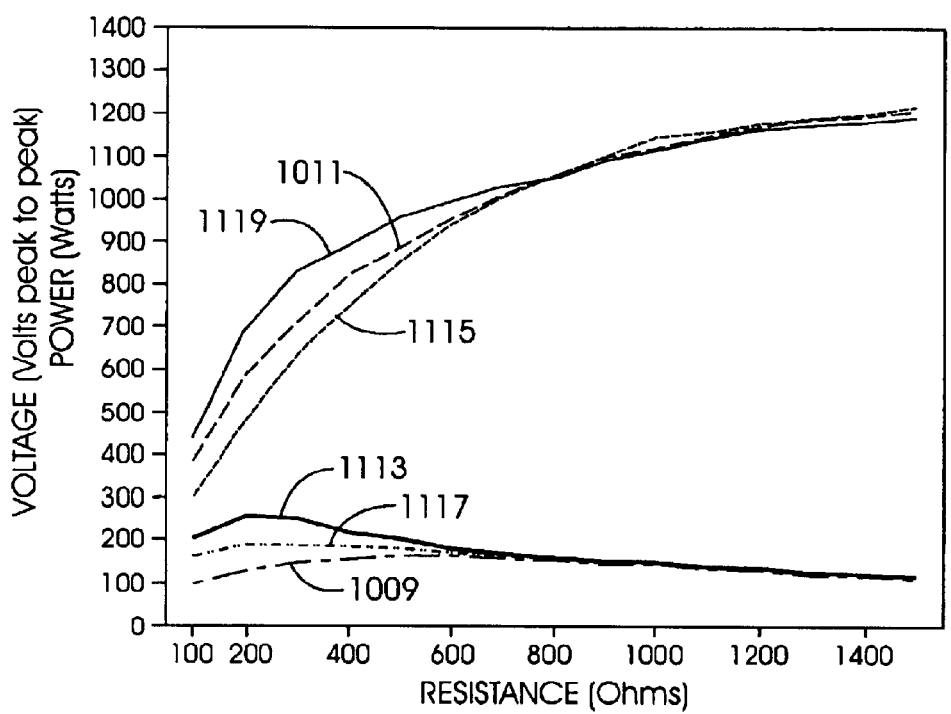
FIG. 27D is a three curve plot illustrating RF output power and voltage profiles.

Referring to FIG. 27D, the performance of the instant system is plotted as an output power and voltage profile with respect to encountered tissue resistance. One early power curve is shown at 1009 while the corresponding voltage characteristic for that control approach is shown at curve 1011. Curve 1009 represented a performance which was unsatisfactory, for example, at tissue resistances below about 500 ohms. Another approach is represented at power curve 1113 and corresponding voltage curve 1115. Curve 1113 was considered unsatisfactory as having too high a power value at resistances below about 500 ohms.

Curves 1117 and 1119 represent the instant system which performs with a substantially flat power profile over a substantially large tissue resistance range. While the curves herein are shown terminating at 1500 ohms, generally flat power performance is provided through about 2000 ohms of tissue resistance.

Figure 27E:
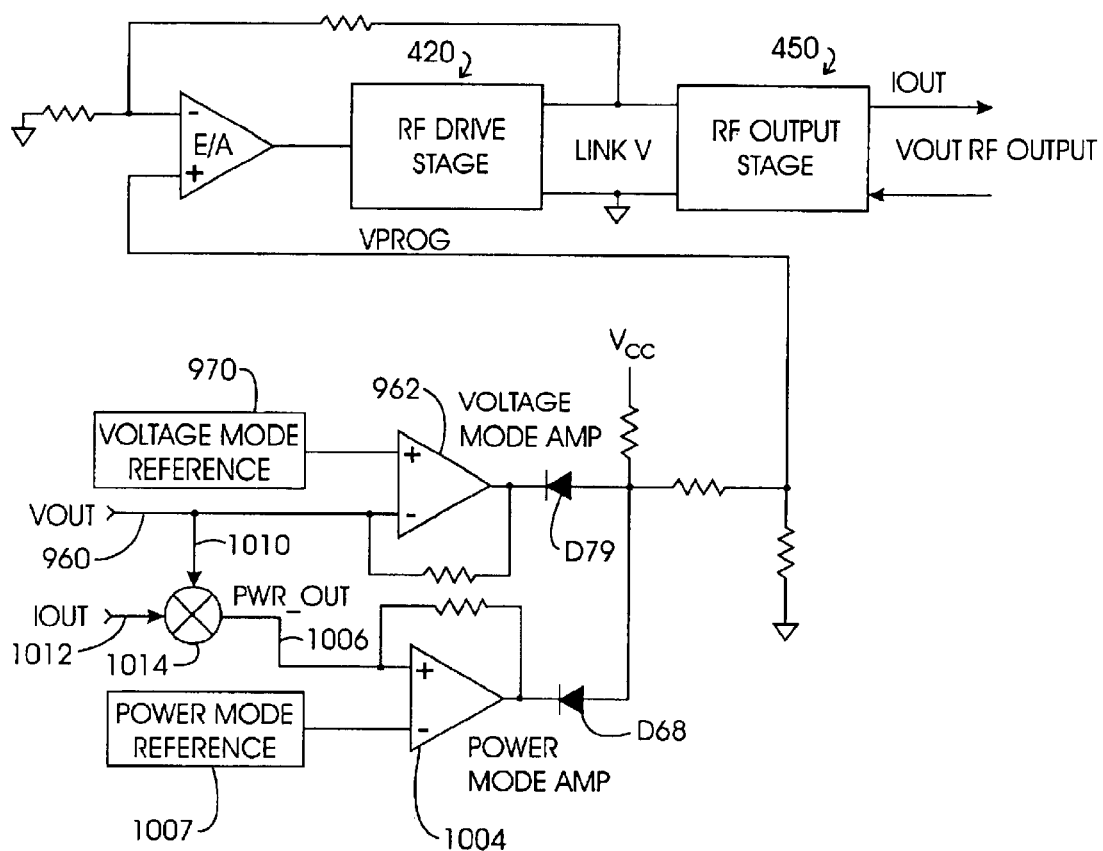
FIG. 27E is a representative circuit symbolically depicting the derivation of a flat power characteristic.

Referring to FIG. 27E, a schematic representation of the triple mode control scheme is presented. For convenience, the identifying numeration described in connection with FIGS. 27B and 27C as well as FIG. 15 are re-presented. Voltage mode amplifier 972 is represented in conjunction with its associated output diode D79. Correspondingly, power mode amplifier 1004 is represented schematically in conjunction with its associated diode D68. The voltage mode reference as described at 970 is introduced to one side of amplifier 962, while the monitored signal VOUT as applied via line 960. Monitored power is developed by multiplier circuit 1014 in response to the IOUT monitored input at line 1012 and the voltage output VOUT is derived from lines 969 and 1010. The resultant PWR_OUT signal is asserted at one side of amplifier 1004, while a power mode reference is asserted to the opposite side as represented at block 1007.

As a consequence of the arrangement with ORed diodes D79 and D68, the control signal VPROG will be evolved under the control of either the voltage mode amplifier or the power mode amplifier. In general, the crossover impedance for these two modes is in the range of 1200–1500 ohms. If the output voltage is above a certain level, the voltage mode ensues and diode D79 is forward biased. The higher output of amplifier 1004 will reverse bias diode D68. The opposite condition obtains during power-mode performance. Both diodes are reverse biased during a boost mode. These outputs are scaled as represented by the three-resistor array. A resultant control signal VPROG is asserted as a control to a control function herein represented as an error amplification feature. The opposite input to the error amplification feature is derived as a monitor of the d.c. link voltage as represented by the feedback loop. A resultant control output is asserted to the RF Drive Stage, a stage which has been described as being asserted to inverter 420 (FIG. 15) to ultimately evolve in d.c. link voltage which, in turn, controls inverter 440 and ultimately provides drive to high voltage output stage 450.

Figure 28:
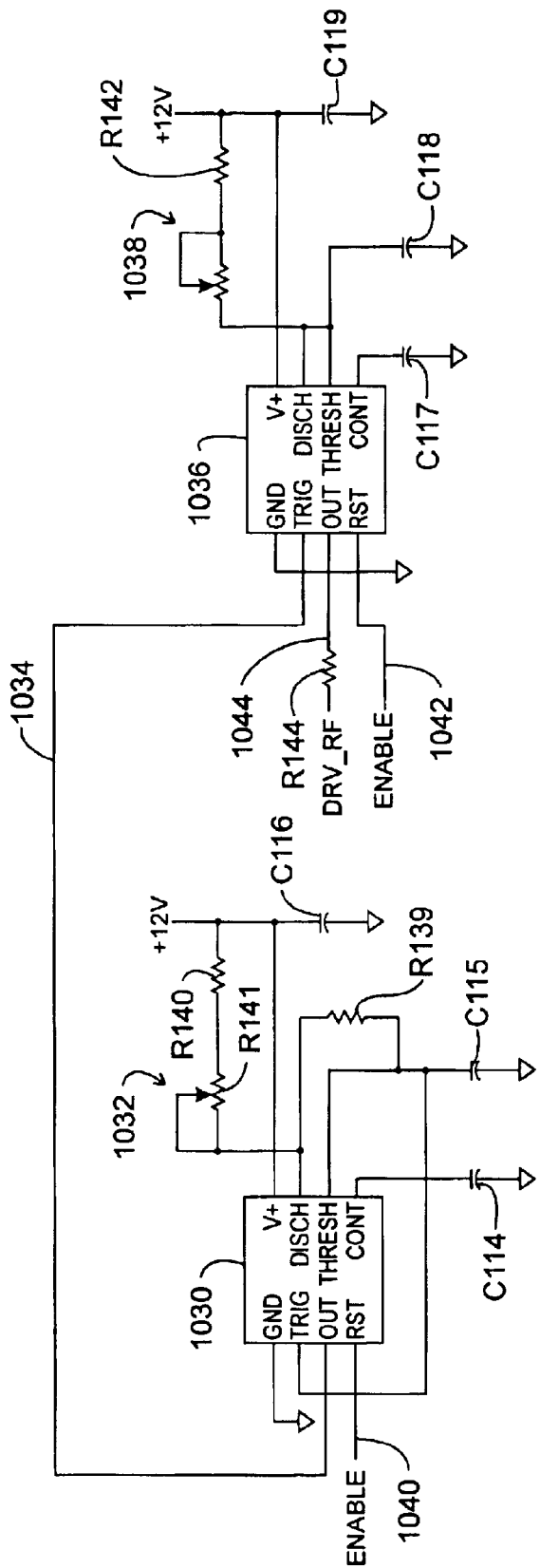
FIG. 28 is an electrical schematic diagram of a control circuit utilized with an RF inverter.

Referring to FIG. 28, the circuitry providing the control input, DRV RF applied to devices 764 and 772 in FIG. 23B for the RF resonant inverter 440 is illustrated. In the figure, the basic frequency is derived with an oscillator integrated circuit 1030 which may be provided as a type LMC555 CMOS Timer marketed by National Semiconductor Corp., of Santa Clara, Calif. which is configured in conjunction with capacitors C114–C116 and resistors R139 and R140. Frequency adjustment may be provided by the manufacturer in connection with a potentiometer represented at 1032 the resistance component of which is provided at resistor R141. The frequency output of device 1030 is presented along line 1034 to the trigger input of another type LNC555 device 1036 which establishes pulse width. Device 1036 is configured in conjunction with capacitors C117–C119 and resistor R142. Pulse width is adjusted by the manufacturer at a potentiometer represented at 1038 incorporating a resistor component R143. Devices 1030 and 1036 are simultaneously enabled by an ENABLE input respectively provided at lines 1040 and 1042 derived both from PLD signal, and a start-up reset. In this regard, while enablement is provided on the occasion of a sequenced signal ultimately provided from the PLD, the RF inverter is not permitted to be enabled during initial system start-up. Accordingly, as a safety feature, the logic or active high ENABLE signal is not provided until after the interval of Power-On Reset (PWR_ON_RST, FIG. 34). The final control signal, DRV_RF is provided from device 1036 at line 1044 which incorporates resistor R144. Note the simplicity of this control input to the RF resonant inverter, a result evolved by utilization of the d.c. link voltage as a peak-to-peak voltage controlling input to the basic inverter excitation circuit.

Figure 29:
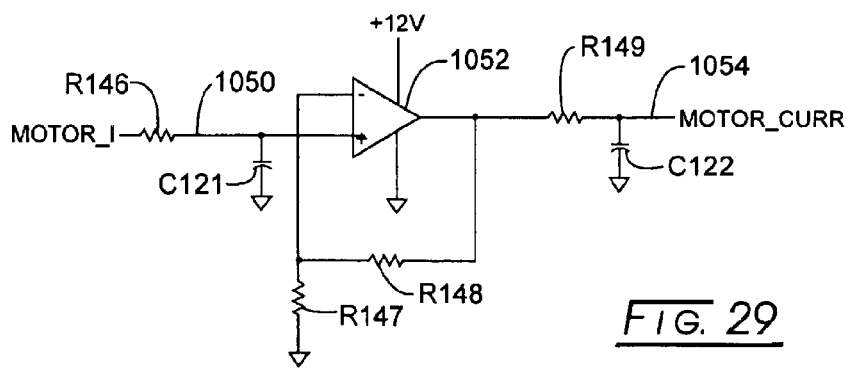
FIG. 29 is an electrical schematic diagram of a circuit for amplifying motor current.

FIGS. 29 through 33 illustrate circuitry associated with the logic used in conjunction with the energization of motor 160a of motor assembly 160. In this regard, motor current, identified as "MOTOR_I" is monitored to carry out this logic. That monitor current is generally too low to be useful and its derivation is described in connection with FIG. 22. Thus, it is amplified initially to develop an enhanced signal identified as "MOTOR_CURR". FIG. 29 shows the amplification of these current signals. In this regard, the initial current signal is introduced through resistor R146 and line 1050 to an amplifier 1052. Amplifier 1052 is configured in conjunction with resistors R147–R149 and capacitors C121 and C122 and provides an enhanced MOTOR_CURR signal at output line 1054.

Figure 30:
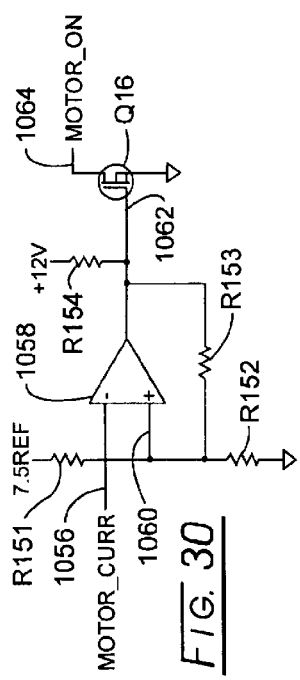
FIG. 30 is an electrical circuit schematic diagram of a motor current monitoring circuit.

FIGS. 29 through 33 provide varying threshold analyses of the motor current for use by the PLD logic device of the system. FIG. 30 shows the initial threshold test which is to determine, at the outset of motor energization, whether the motor is indeed working. For this purpose, a small amount of free movement of the yoke 180 is permitted prior to contact being made with the ears or tabs as at 138 and 140 (FIG. 2) of the drive member 276. In general, that spacing is adequate to permit free travel before contact amounting to about one half second. During this very short test interval, the motor current is very low but discernable, for example, exhibiting at least about a ten milliamp threshold value. If the motor 160a is not on at a time when it should be on, then a system fault will be at hand with appropriate shutdown and visual cueing. FIG. 30 shows that the MOTOR_CURR signal is introduced at line 1056 to one input of a comparator 1058. The reference input to comparator 1058 is the earlier-described 7.5REF disclosed in connection with FIG. 27B. That reference voltage is adjusted by resistors R151–R153 and introduced via line 1060 to device 1058. The output of device 1058 is provided at line 1062 which is coupled to +12V source through a pull-up resistor R154. Where the properly performing motor current level is present, a "MOTOR_ON" signal is generated at line 1064 by turning off transistor Q16.

Figure 31:
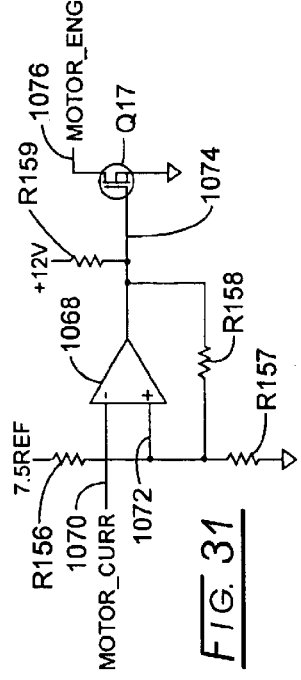
FIG. 31 is an electrical schematic diagram of a motor monitoring electrical circuit.

Looking to FIG. 31, the MOTOR_CURR signal is introduced to comparator 1068 from along line 1070. Comparator 1068 is configured with the 7.5REF reference signal and resistors R156–R158 to react to a threshold provided at line 1072 representing, for instance, about 23 milliamps of motor current draw. As the yoke 180 engages the ears 138 and 140 (FIG. 3) the motor 160a will commence doing more involved work and typically will exhibit a current draw of about 45 milliamps. This condition then is witnessed at comparator 1068 and where the above-established threshold for this motor condition is exceeded, then comparator 1068 reacts at its output line 1074 to turn off transistor Q17. Thus, a "MOTOR_ENGAGED" signal is generated at line 1076 for the logic of the control system. As before, line 1074 is coupled with +12V through pull-up resistor R159.

The networks of FIGS. 30 and 31 perform in concert. A determination by the network in FIG. 30 during the initial one half second test interval that motor current is above a low threshold, for example, of about 5 milliamps, results in the MOTOR_ON signal being generated. However, during this same test interval, should the motor current exceed the threshold of the network of FIG. 31 to result in a MOTOR_ENGAGED signal, then this initial test fails, resulting in a fault condition.

Following passage of the initial one half second test, the network of FIG. 31 will detect whether or not its threshold, for instance, of 23 milliamps, has been met. That indicates appropriate engagement of the yoke 180 with tabs or ears 138 and 140 (FIGS. 2 and 3) if, during forward movement of drive member 276, the threshold of the network of FIG. 31 is not sustained, a fault condition results with system halt and visual cueing.

Figure 32:
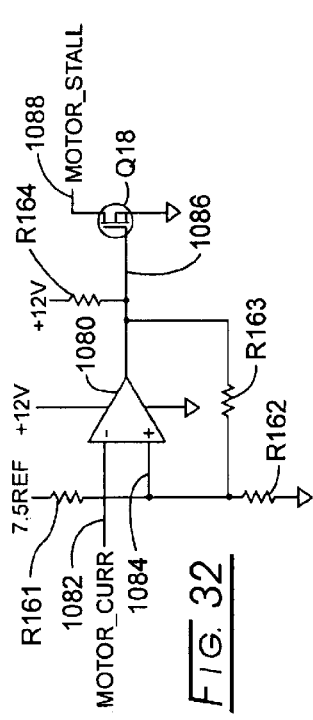
FIG. 32 is an electrical schematic diagram of a motor monitoring electrical circuit.

Referring to FIG. 32, as tissue capture is completed, for example, as illustrated in connection with FIG. 10, the motor 160a will enter a forward stall condition and current will rapidly spike to about 130 milliamps. In FIG. 32, the MOTOR_CURR signal again is introduced to a comparator 1080 via line 1082. Comparator 1080 is configured with 7.5REF and resistors R161–R163 to provide a forward stall threshold input at line 1084. The comparator 1080 provides a logic low true output at line 1086 when a forward stall condition is detected. As before, line 1086 is coupled through pull-up resistor R164 to +12V and is connected to the gate of transistor Q18. Accordingly, a "MOTOR_STALL" signal or condition is derived at line 1088 by the turning off of transistor Q18.

Upon detecting the forward motor stall, the control assembly reverses the drive polarity to the motor 168 as discussed in connection with FIG. 22 and the transfer assembly 176 releases from its abutting engagement with drive member 276, tabs 138 and 140, whereupon it is driven back to its "home" position illustrated in general in FIG. 3. The resultant reverse stall current is of lower amplitude than the forward stall current and is detected.

Figure 33:
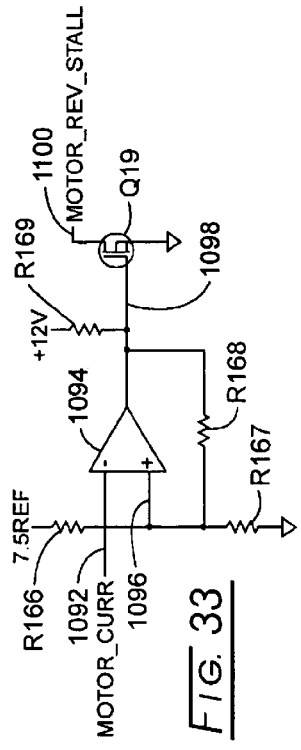
FIG. 33 is an electrical schematic diagram of a motor monitoring electrical circuit.

Looking to FIG. 33, the MOTOR_CURR signal is introduced at line 1092 to a comparator 1094. The reference or threshold level for comparator 1094 is set for the detection of a reverse stall current level of the motor 160a and is provided from 7.5REF in conjunction with resistors R166–R168 at line 1096 to the reference input of comparator 1094. The output of comparator 1094 at line 1098 is coupled to the gate of transistor Q19 as well as pull-up resistor R169 to +12V. Accordingly, when the reverse stall condition is detected, a low true condition occurs at line 1098 to turn off transistor Q19 and provide the "MOTOR_REV_STALL" condition or signal at line 1100. Comparators 1058, 1068, 1080 and 1094 may be provided, for example, as type LM339 Lower Power, Low Offset Voltage Comparators marketed by National Semiconductor Corp. (supra)

Figure 34:
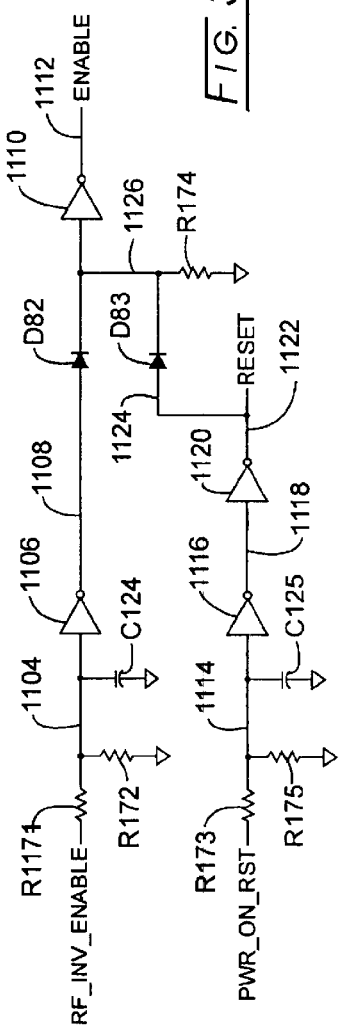
FIG. 34 is an electrical schematic diagram showing a derivation of reset and enable signals.

Looking to FIG. 34, circuitry is represented which provides "ENABLE" and "RESET" signals upon the occurrence of respective RF_INV_ENABLE and PWR_ON_RST signals. The latter reset signal is developed from the control assembly PLD. In the figure, the former logic high true input signal is introduced through resistor R171 at line 1104 to the input of a Schmitt trigger implemented inverter buffer 1106, the logic low output of which at line 1108 extends through ORing diode D82 to the input of a second buffer inverter 1110 to provide a logic high "ENABLE"

signal at output line 1112. Filtering resistor R172 and filtering capacitor C124 are coupled with line 1108. The power-on reset (PWR_ON_RST) signal is introduced through resistor R173 and line 1114 to the input of a Schmitt trigger implemented inverter buffer 1116, the logic low output of which is provided at line 1118 which is directed to the input of a second inverter buffer 1120. The logic high output of inverter buffer 1120 at line 1122 carries a "RESET" signal and also negates the earlier-described ENABLE signal by a wired ORing arrangement including line 1124, diode D83, line 1126 and resistor R174. In this regard, line 1126 introduces the signal to the input of inverter buffer 1110. Filtering resistor R175 and filtering capacitor C125 are coupled between line 1114 and ground. As noted earlier, as a safety feature, the RF inverter operation is blocked during system start-up occurring during the power on reset interval. This is accomplished, inter alia, by the above-noted ORing arrangement derived with diodes D82 and D83 which function to remove the ENABLE signal deriving this initial interval.

Figure 35:
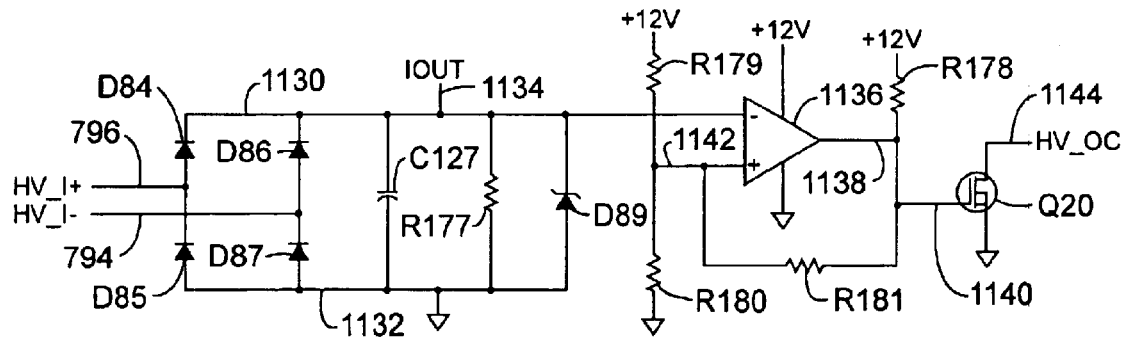
FIG. 35 is an electrical schematic diagram of a circuit monitoring an output over-current condition.

Referring to FIG. 35, comparator circuitry monitoring for a high voltage over-current condition is revealed. In the figure, the current signals HV_I+ and HV_I− as were developed at the high voltage output stage 450 as described in connection with FIG. 23B are rectified. In this regard positive current is introduced intermediate diode pair D84 and D85 from line 796 and negative current signals are introduced to diode pair D86 and D87 from line 820. These rectifying diode pairs are located between lines 1130 and 1132, the latter being coupled with secondary ground and the former providing the earlier-described output current signal, IOUT as represented at line 1134 (see FIGS. 27C, 27D). Capacitor C127 and resistor R162 provide a filtering function, while diode D89 functions as a clamp. Line 1130 extends to one input of a comparator 1136 having output at line 1138 extending through pull-up resistor R178 to +12V and coupled to the gate of transistor Q20 from line 1140. Comparator 1136 is configured for establishing a high voltage over-current threshold reference input at line 1142 in conjunction with +12V source and resistors R179–R181. With the arrangement shown, a low true output at the comparator 1136 generates a corresponding over-current signal, "HV_OC" at line 1144 by turning off transistor Q20. This line reappears in FIG. 41A.

Figure 36:
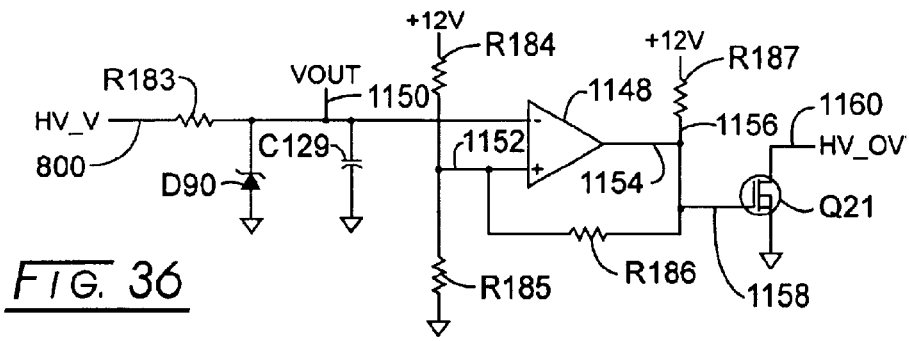
FIG. 36 is an electrical schematic diagram of a circuit for monitoring an over-voltage condition.

Looking to FIG. 36, comparator circuitry is illustrated which determines the presence of an over-voltage condition at the generator output. The HV_V signal is derived as has been described in connection with FIG. 23B at line 800. Line 800 reappears in the instant figure providing for the application of the high voltage signal through input resistor R183 to one input of a comparator 1148. Line 800 is seen coupled with a filter capacitor C129 and clamping diode D90. This filtering arrangement provides for the signal, VOUT shown at line 1150 which is described in connection with FIGS. 27A, 27C and 27D. The over-voltage reference input to comparator 1148 is provided at line 1152 and is derived from +12V source in connection with resistors R184–R186. The output of comparator 1148 at lines 1154 and 1156 is coupled through pull-up resistor R187 to +12V and is then connected via line 1158 to the gate of transistor Q21. Accordingly, a low true output at comparator 1148 turns off transmitter Q21 to create an over-voltage signal, "HV_OV" at line 1160 which reappears in FIG. 41A.

Figure 37:
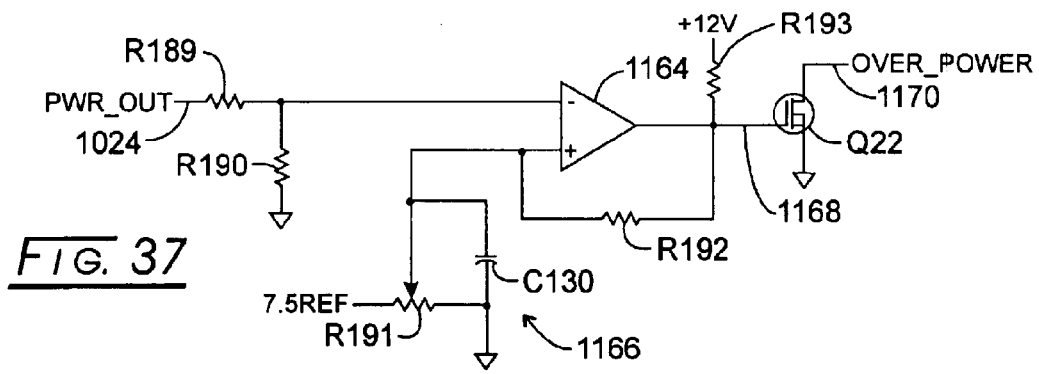
FIG. 37 is an electrical schematic diagram of a circuit for monitoring power level.

Referring to FIG. 37, a comparator circuit is illustrated which determines the presence of an over-power condition at the generator output for the embodiment of the invention associated with an active electrode of varying surface area or geometry. Accordingly, this monitoring is carried out in conjunction with the PWR_OUT signal, the derivation of which was described in connection with FIG. 27C at line 1024. That line reappears in the instant figure incorporating an input resistor R189 and extending to one input of a comparator 1164. A reference input to comparator 1164 is derived from a potentiometer network incorporating a reference, 7.5REF, directed to potentiometer resistor component R191 and capacitor C130 in conjunction with resistor R192. The output of comparator 1164 at line 1168 is coupled with the gate of transistor Q22 as well as through pull-up resistor R193 to +12V. Accordingly, a low true output of comparator 1164 turns off transistor Q22 to derive an "OVER_POWER" condition at line 1170 which reappears in FIG. 41A. A filter resistor R190 is connected between line 1024 and ground. The reference input to comparator 1164 for the instant embodiment is established to accommodate for the excursions or variations of power involved with active electrodes of varying surface area or geometry.

Figure 38:
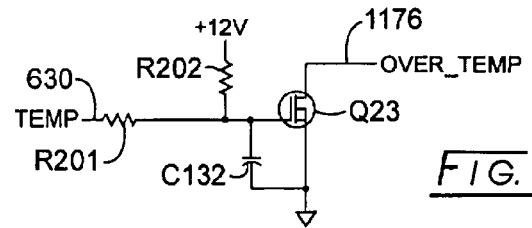
FIG. 38 is an electrical schematic diagram of a circuit monitoring for over-temperature conditions.

Referring to FIG. 38, an over-temperature circuit is portrayed. The temperature signal, TEMP having a low true condition when monitored temperature is excessive, has been described in connection with FIG. 19. Line 630 extending from the temperature responsive device described in that figure reappears in the instant figure in conjunction with resistor R201 as extending to the gate of transistor Q23. Additionally, line 630 is coupled through pull-up resistor R202 to +12V and through filtering capacitor C132 to secondary ground. With the arrangement shown, a low true "OVER_TEMP" signal is derived at line 1176 in the presence of an excessive hardware temperature. Line 1176 reappears in FIG. 41A.

The d.c. link voltage has been described in connection with FIG. 23A as being monitored at line 746. That monitoring signal has been identified as "LINK_V". The control assembly determines whether this voltage is either above or below a window of acceptable operation. The term "window" as used herein is meant to include a point value.

Figure 39:
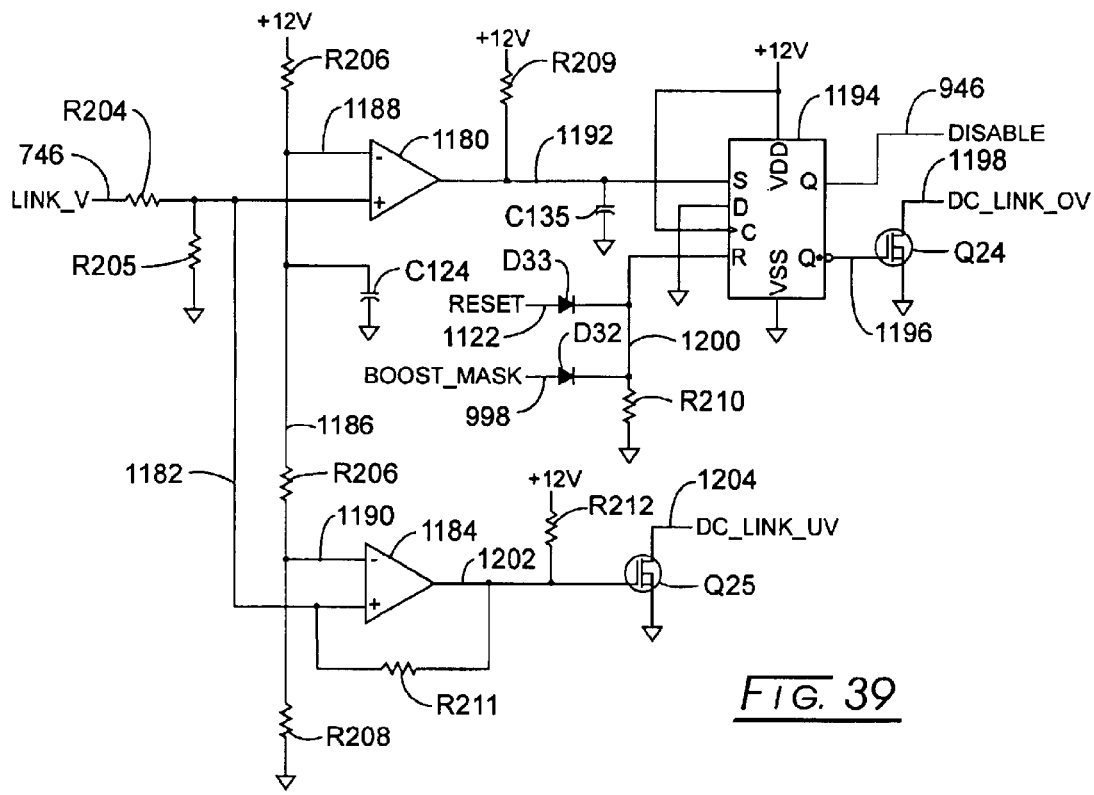
FIG. 39 is an electrical schematic diagram of a circuit for monitoring the level of d.c. link voltage.

Referring to FIG. 39, line 746 reappears introducing the LINK_V signal to the positive input terminal of a link over-voltage comparator 1180. Line 746 is configured with resistors R204 and R205. Additionally connected to line 746 is line 1182 which extends to the positive terminal input of a link under-voltage comparator 1184. The reference or threshold inputs for both comparators 1180 and 1184 are derived from +12V source at line 1186. In this regard, +12V source is introduced to line 1186 through resistor R206 and that reference value then is directed to comparator 1180 through line 1188. Line 1186 additionally incorporates resistors R207 and R208 to establish a d.c. link under-voltage threshold reference input to the negative terminal of comparator 1184 and line 1190. Line 1186 is filtered by capacitor C134.

The output of comparator 1180 at line 1192 is coupled through pull-up resistor R209; is coupled with filter capacitor C135; and extends to the set, S, terminal of an RS flip-flop 1194 configured as a latch. Device 1194 may be provided as a type 4013B CMOS dual "D" type flip-flop marketed by Texas Instruments, Inc., of Dallas Tex. If the level of monitored link voltage at line 746 exceeds the threshold established at line 1188, output line 1192 assumes a logic high condition to cause latch 1194 to assume a set state. As a consequence, its Q output at line 946 changes to a logic high level to create the "DISABLE" signal described in conjunction with FIG. 26, turning on MOSFET transistor Q14 to disable the link voltage controller 920. A complimentary low true output occurs at the Q• terminal at line

1196. Line 1196 is coupled to the gate of MOSFET transistor Q24, the drain and source terminals which are coupled respectively with line 1198 and ground. This turns off transistor Q24 to derive the link over-voltage signal, "DC_LINK_OV", which is transmitted to the control PLD.

As discussed in connection with FIG. 27A, during an enhanced link voltage-based boost mode, a logic high true BOOST_MASK signal is developed at line 998. Line 998 reappears in the instant figure extending through ORing diode D32 to line 1200 incorporating resistor R210 and extending to the reset, R, terminal of latch 1194. Accordingly, during the boost mode, latch 1194 is held in a reset state wherein its Q terminal at line 946 is held at a logic low to block any DISABLE signal and its Q•terminal at line 1196 is held at a logic high level turning on transistor Q24. Thus the DC_LINK_OV signal is blocked for the duration of the boost mode.

As another feature, during the interval of power-up reset, the system holds latch 1194 in a reset state to assure that the over-voltage-based signals as above discussed will not appear at lines 946 and 1196. Accordingly, the active high level RESET signal developed as described in connection with FIG. 34 at line 1122 is transmitted through the ORing diode D93 to line 1200 and the reset terminal R of latch 1194. It may be recalled from FIG. 34 that the presence of a RESET signal negates the ENABLE signal to disable the RF inverter 420 function.

Looking to d.c. link under-voltage comparator 1184, the output of this device is provided at line 1202. Line 1202 is coupled with pull-up resistor R212 to +12V source and through resistor R211 to input line 1182. Output line 1202 extends to the gate of MOSFET transistor Q25. The drain of transistor Q25 is coupled with line 1204 carrying the DC_LINK_UV signal and its source is coupled to ground. Accordingly, in the presence of an under-voltage at the d.c. link, then the output of comparator 1184 and line 1202 assumes a low logic true condition to turn off transistor Q25 and develop the noted d.c. link under-voltage signal for conveyance to the PLD at a control board. Thus, the link voltage level is monitored with respect to over-voltage and under voltage conditions.

Figure 40:
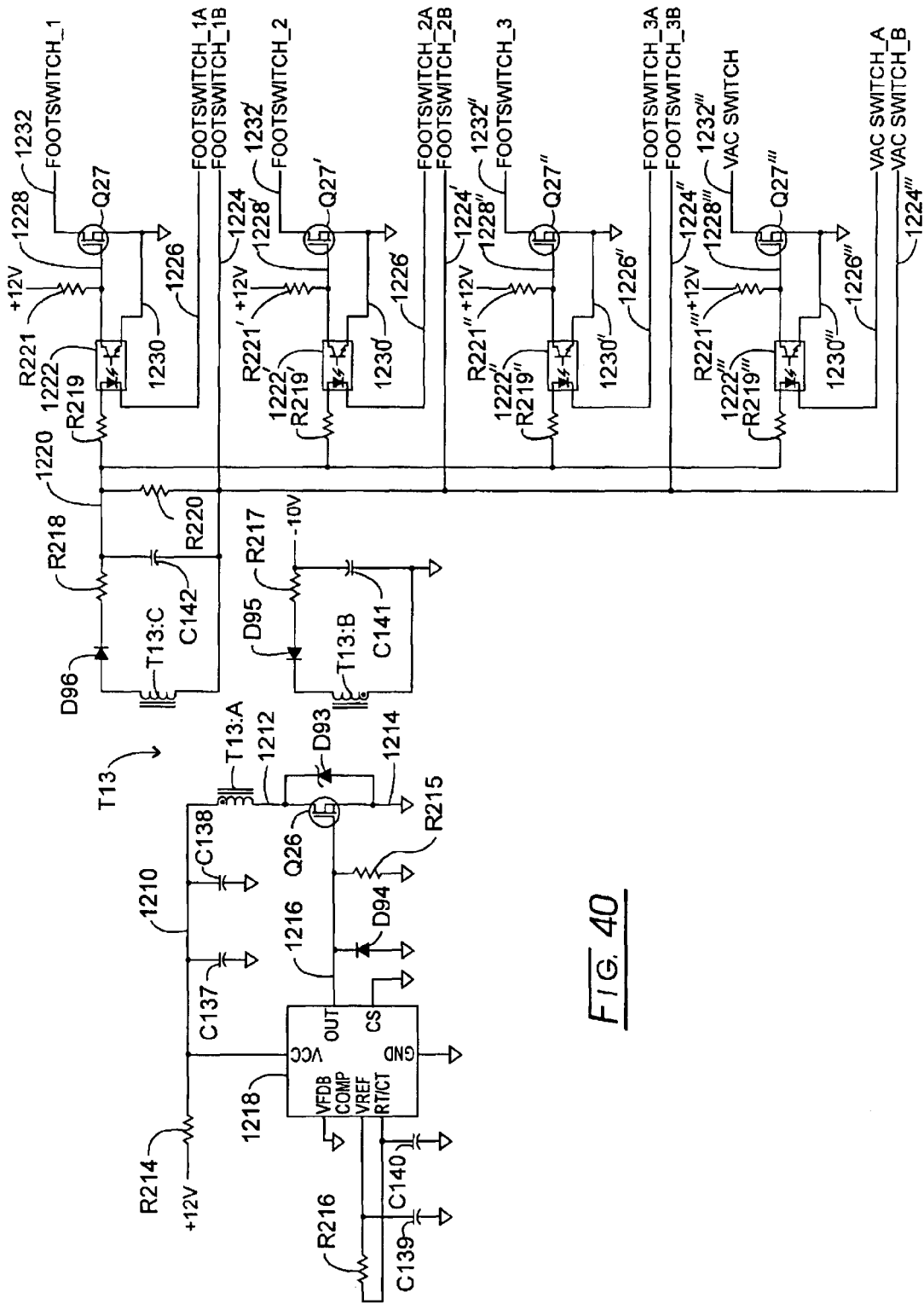
FIG. 40 is an electrical schematic diagram showing a circuit deriving a footswitch actuation input.

Referring to FIG. 40, a power converter and isolation circuit employing a network for response to actuation of the footswitches 88 and vacuum switch 51 (FIG. 1) is portrayed. This circuit is designed to accommodate footswitch and vacuum switch devices which do not have built-in electrical isolation characteristics. Thus, an opto-isolator feature is provided. In the figure, +12V source is applied through resistor R214 and line 1210 to the primary side, T13:A of an isolation transformer T13. Line 1210 is filtered with capacitors C137 and C138. The opposite side of the transformer primary at line 1212 is coupled with the drain terminal of MOSFET transistor Q26. A blocking diode D93 extends across the drain and source terminal at the transistor. The source of transistor Q26 is coupled to ground via line 1214 and its gate is coupled via line 1216 to the OUT terminal of power converter 1218. Line 1216 is coupled with filter resistor R215 as well as clamping diode D94. Provided, for example, as a type UC3845 device marketed by Unitrobe Corp. of Merrimack, N.H., converter 1218 is configured with resistor R216 and capacitors C139 and C140 and functions to chop the input to primary transformer side T13:A by selectively turning transistor Q26 on and off. One secondary of transformer T13, shown at T13:B, derives a −10V output and is shown performing in conjunction with rectifying diode D95, resistor R217 and filter capacitor C121. The −10V source is employed as an input to multiplier 1014 at line 1017 as described in conjunction with FIG. 27C. A next secondary side of transformer T13 is shown at T13:C. This secondary functions to provide electrical isolation for footswitches 88 and vacuum switch 51. The input lead pairs from each of the footswitches 88a–88c as well as the vacuum switch 51 are opto-isolated and connected with secondary side T13:C. One side of secondary T13:C is coupled at line 1220 incorporating rectifying diode D96 and resistor R218. The opposite side of secondary T13:C is coupled to line 1224. Capacitor C142 and resistor R220 extend between lines 1220 and 1224 and, in effect, a node utilized by four identical isolation networks is developed across resistor R220. The first of these networks, for example, associated with footswitch 88a incorporates line 1220 and resistor R219 which extends to the anode input of an opto-isolator 1222. The cathode input of opto-isolator 1222 is coupled with line 1226 which extends to one side of footswitch 88a and is labeled "FOOTSWITCH_1A". Line 1224 extends to the opposite side of switch 88a and is labeled "FOOTSWITCH_1B". The low voltage output side of opto-isolator 1222 is connected at line 1228 through the gate of transistor Q27 and the opposite output thereof is coupled via line 1230 to its source terminal and to secondary circuit ground. Line 1228 is coupled through pull-up resistor R222 to +12V source and, accordingly, with the actuation of footswitch 88a, the signal "FOOTSWITCH_1" is produced in low logic true fashion at line 1232. This network, incorporating resistors R219 and R221, opto-isolator 1222, and transistor Q27 is repeated and connected across resistor R220 for the remaining footswitches 88b and 88c as well as for vacuum switch 51. Accordingly, the same network identifying numeration is used to describe these networks, but in primed fashion. In this regard, the footswitch 88b network is identified in single primed fashion in combination with the switch labels "FOOTSWITCH_2A" and "FOOTSWITCH_2B", providing the low logic true output signal "FOOTSWITCH_2". Footswitch 88c is identified in double primed fashion in combination with the switch labels "FOOTSWITCH_3A" and "FOOTSWITCH_3B", providing the low logic true output signal, "FOOTSWITCH_3". Similarly, the vacuum switch 51 network is identified in triple primed fashion in combination with the switch labels "VACSWITCH_A" and "VACSWITCH_B", providing the low logic true output signal, "VACSWITCH".

Figure 41A:
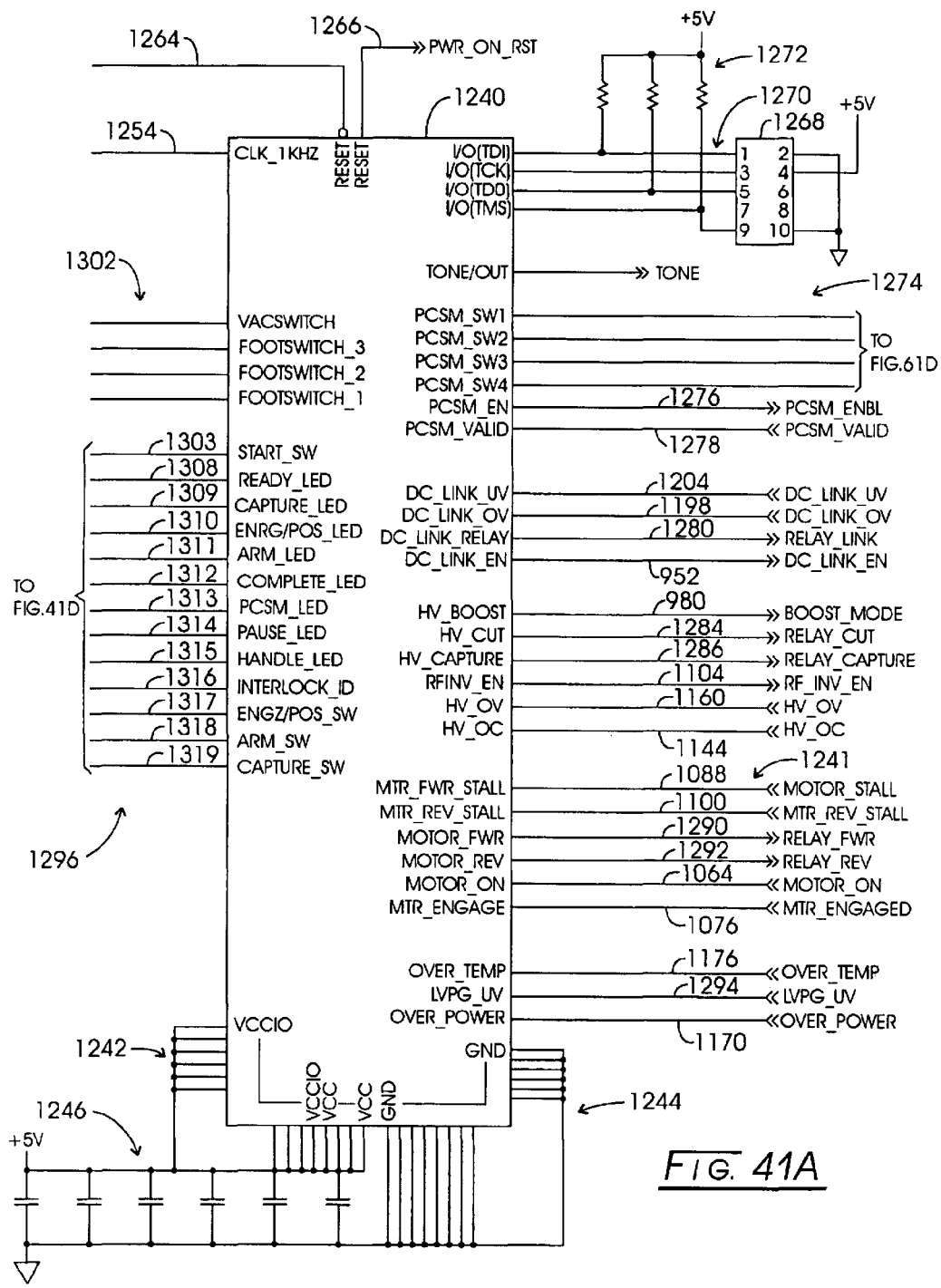

As noted earlier herein, the control daughter board of the circuit assembly incorporates the above-referenced PLD along with associated filtering and pull-up functions. In general, where transistors have been described as being turned off, the relevant lines typically are pulled to a logic high at the control board. Additionally, this board incorporates an audio drive to provide the aural cueing of the system and a reset network supporting the PLD. The PLD may be characterized as a hardware programmable compilation of logic gates. This gate compilation responds in a sequential logic to develop a series of states effecting a control for the system at hand. This device may be a type EPM7192SQC160-15 programmable logic device PLD marketed by Altera, Inc. of San Jose, Calif. The device is represented at 1240 in FIG. 41A. FIG. 41A should be considered in conjunction with FIGS. 41B–41E in the manner labeled thereon. In FIG. 41A, a regulated +5V and associated ground are shown introduced to device 1240 from respective line arrays 1242 and 1244 to VCC and GND designated terminals. The +5V are shown filtered by a six capacitor array 1246.

Looking additionally to FIG. 41B, a clock network is represented in general at 1248. Network 1248 includes a crystal oscillator device 1250 which may be provided, for example, as a type 74302 marketed by M-Tron Industries, Inc. of Yankton, S. Dak. which responds to a __RESET input applied at line 1252. Configured in conjunction with inductor L10 and capacitors C144–C146, the network 1248 provides a 1 KHz input at line 1254 to PLD 1240.

Looking to FIG. 41C, a reset network is shown generally at 1258 which functions to hold the system low for a specified amount of time to assure a power supply stabilization. It may be recalled that, during this reset interval, as a safety feature, the RF inverter 420 function is not enabled (FIG. 34). Network 1258 performs at the time of a system power on or such time as the regulated 5V power supply for the instant circuit diminishes to a certain extent. The network is centered about a reset device 1260 which may be a type DS1233DZ-5 marketed by Dallas Semiconductor, Inc. of Dallas, Tex. and which is configured in conjunction with capacitors C153 and C154 as well as resistor R223. A RESET output is provided at line 1262 which is shown in FIG. 41B as being introduced to the oscillatory device 1250 through resistor R213 and line 1252. The same signal is directed via line 1264 to the RESET terminal of PLD 1240. PLD 1240 also provides the logic high true PWR__ON__ RST signal at line 1266 as described in conjunction with line 1114 at FIG. 34.

Returning to FIG. 41A, an externally accessible jumper or connector is shown at 1268 which provides a four line array to I/O ports of PLD 1240 as shown in general at 1270. Three of those four lines of the array 1270 are pulled up to ±5V through a pull-up resistor array shown generally at 1272.

Extending from PLD 1240 is a four line array shown generally at 1274 which provides an output for controlling relays of the PCSM circuit 462 (FIG. 15). These lines correspond with line 468 of that figure. Below array 1274 is a line 1276 providing a PCSM circuit enablement signal, PCSM__ENBL. Below line 1276 is an input line 1278 carrying a PCSM circuit valid input signal, PCSM__VALID, indicating to the PLD an appropriate passage of the earlier described PCSM test.

The d.c. link monitoring feature as described in conjunction with FIG. 39 as being inputted to PLD 1240 are shown as earlier-described at input lines 1204 and 1198. Link relay 434 control, RELAY__LINK is provided at line 1280 and the DC__LINK__EN d.c. link enable signal earlier-described at line 952 reappears in the instant figure. Below that grouping is an array 1282 of input and output lines to PLD 1240 concerned with the high voltage function including the boost mode signal, BOOST__MODE earlier-described at line 980 in conjunction with FIG. 27A which reappears in the instant figure. The high voltage precursor electrode cut signal, RELAY__CUT as earlier described in conjunction with FIG. 22 is shown at line 1284 and the corresponding subsequently activated RELAY__CAPTURE signal as described in conjunction with FIG. 22 is shown transmitted at line 1286. The RF inverter enablement signal RF__IND__EN earlier described in connection with FIG. 34 at line 1104 reappears with the same line numeration. The high voltage overvoltage signal, HV__OV input earlier-described at line 1160 in connection with FIG. 36 reappears in connection with line 1160 and the corresponding high voltage over-current signal HV__OC earlier-described at line 1144 in conjunction with FIG. 35 reappears with the same line numeration.

Below line array 1282 is another array 1288 of inputs to and outputs from PLD 1240. Within this array 1288, the motor 160a forward stall signal (MOTOR__STALL) signal and the motor reverse stall signal (MTR__REV__STALL) signal described in conjunction with FIGS. 32 and 33 in conjunction with respective lines 1088 and 1100 reappear with the same line numeration. The signal providing for forward motor drive, RELAY__FWD described in connection with FIG. 22 is represented at line 1290, while the reverse drive command to the motor, RELAY__REV as described in the latter figure is represented at line 1292. Input lines 1064 and 1076 respectively carry the signals, MOTOR__ON, monitoring initial motor energization, and a monitoring condition signal, MTR__ENGAGED which is active when the yoke 180 has engaged drive member 276. These motor functions as identified in conjunction with lines 1088, 1100 and 1064, 1076 have been discussed in connection with FIGS. 30–33, while lines 1290 and 1292 reappear in FIG. 22.

Figure 43:
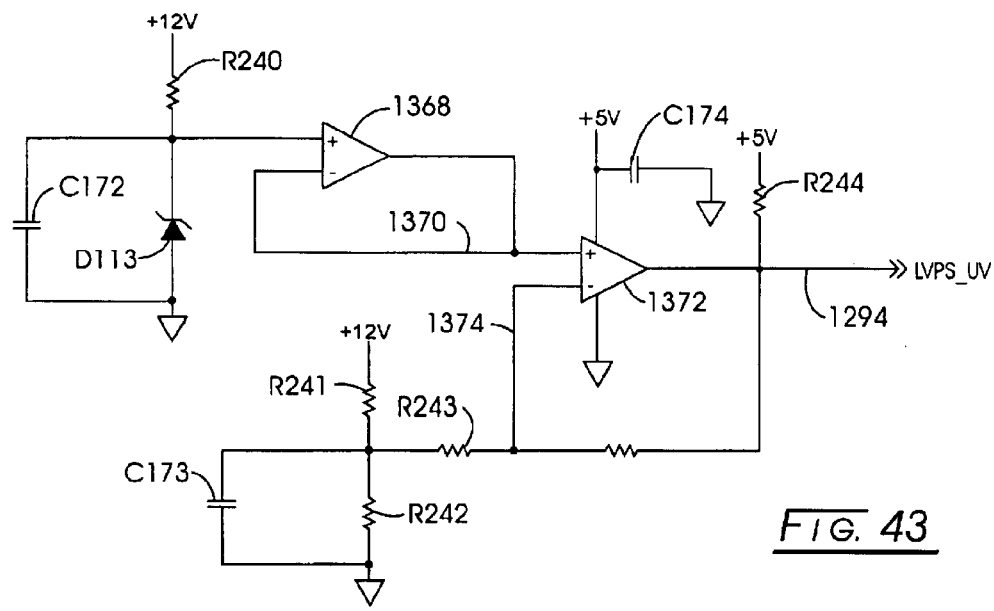
FIG. 43 is an electrical schematic diagram of a circuit for monitoring a low voltage power supply.

The over-temperature signal, OVER__TEMP input to PLD 1240 as described in connection with FIG. 38 is shown at earlier-identified line 1176 and a low voltage power supply under-voltage condition signal, LVPS__UV as described in conjunction with FIG. 43 is inputted at line 1294. The over-power condition signal, OVER__POWER or OVER__POWER' as described in connection with FIG. 37A or 37B is inputted to PLD 1240 as reappearing line 1170, or 1170'.

Looking to the opposite side of PLD 1240, a thirteen line array is represented generally at 1296. Of the lines within array 1296, certain of them carry signals responding to external switching and an interlock test, as well as providing outputs for selectively illuminating light emitting diodes (LEDs) both at the front panel of console 64 and at the instrument 12. Above the line array 1296 a line array 1302 is shown with labeling corresponding with the opto-isolated input signals from footswitches 88 and vacuum switch 51. These input signals were discussed above in connection with FIG. 40.

Figure 41D:
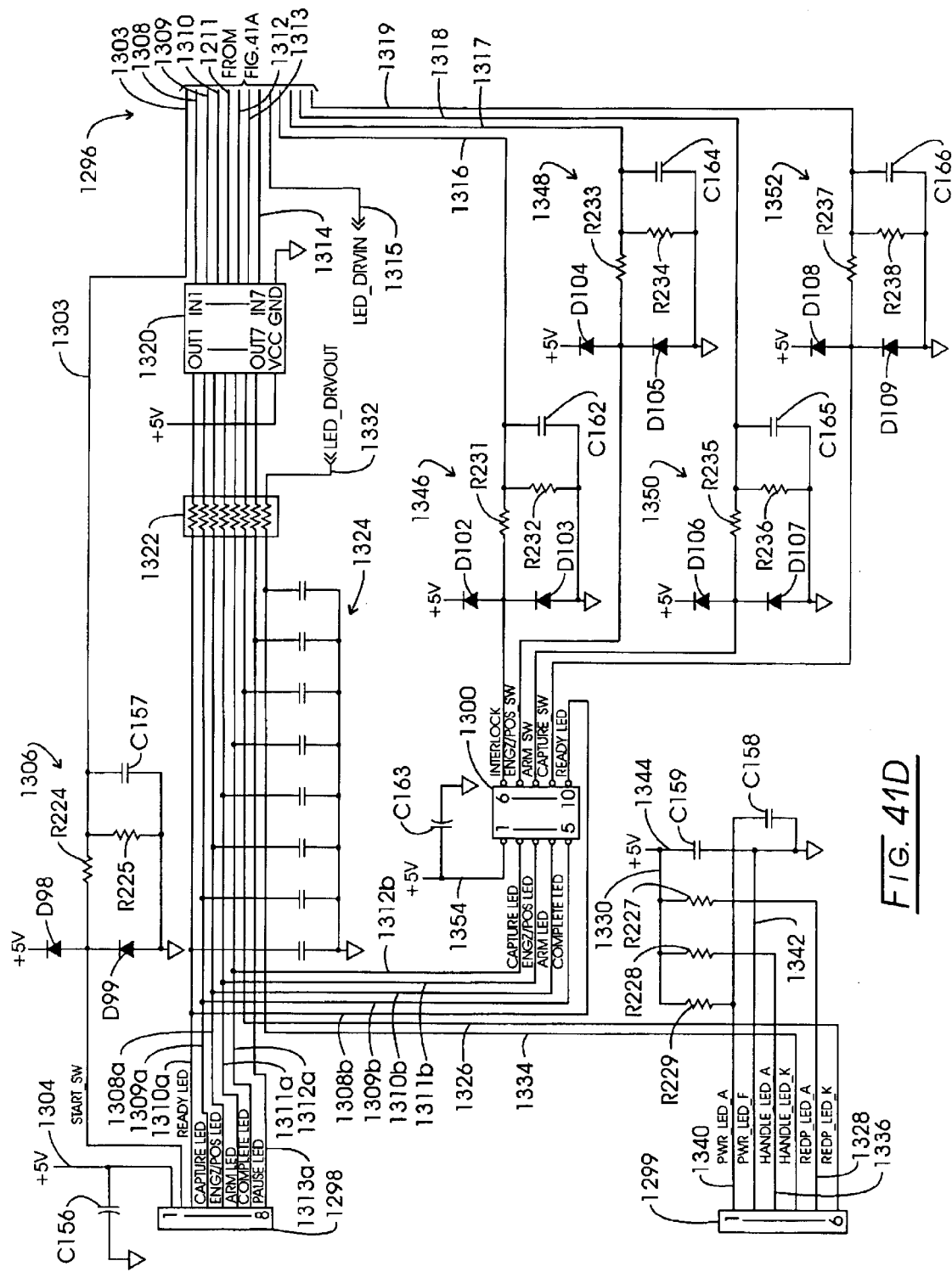

Referring additionally to FIG. 41D, line array 1296 reappears and the inputs and outputs represented thereby may be seen to extend to three connectors 1298–1300. Connector 1298 is coupled with a printed circuit board located at the upper portion of the front panel of console 64; connector 1299 is coupled with a lower panel assembly serving the lower portion of the front panel of console 64; and connector 1300 is operationally associated with a connector operating in conjunction with instrument 12.

Line 1303 which carries a start switch signal identified as "START__SW" as initially derived by the actuation of switch 92 on consoled 64 (FIG. 1) is uppermost in array 1296. This is the only console-mounted switch having an input to PLD 1240. The switch must be actuated in order for any procedure to commence, the switch signal being utilized for an initial setup of the motor driven components of the device and to commence the PCSM return electrode test. The start/reset signal provided by this switch is derived in conjunction with the regulated +5V voltage associated with PLD 1240 as represented at line 1304 which is coupled with filter capacitor C156. Line 1302 also is implemented with a protective network represented generally at 1306 comprised of clamping diodes D98 and D99, resistors R224 and R225 and capacitor C157. Thus configured, the diodes of network 1306 provide clamps limiting the signal at line 1302 to values between +5V and ground and an R-C filter is incorporated. This protective arrangement assures the appropriate signal without interference.

Output lines 1308–1312 provide outputs effecting the energization of the four LED illuminators at the top portion of the front panel of console 64. Looking additionally to FIG. 1, the READY__LED signal at line 1303 effects the illumination of the LED illuminator 94; the CAPTURE__

LED signal at line 1309 effects the illumination of illuminator LED 100; the ENGZ/POS_LED signal at line 1310 effects the illumination of illuminator LED 96; the ARM_LED signal at line 1310 effects the illumination of illuminator LED 98; line 1311, carrying a COMPLETE_LED signal effects the illumination of illuminator LED 102; and a PAUSE_LED signal at line 1314 effects the illumination of illuminator LED 104. These signals are buffered at buffer 1320 and filtered by connection with six resistors within a resistor array 1322 performing in connection with a filter-associated six capacitors of capacitor array 1324.

Pause LED 104 is illuminated under the control of PLD 1240 at such time as the practitioner releases footswitch 88 during a capture mode of operation wherein the pursing cables are electrosurgically excited. Such excitation of the pursing cables is terminated as well as energization of motor assembly 160 during a pause interval and the re-energization can occur only following actuation of the arm/disarm switch 54 on instrument 12, re-engagement of footswitch 88, and actuation of capture switch 56. For any such restart operation, the control assembly again creates a boost voltage mode of operation to assure creation of a cutting arc at the pursing cable implemented active capture electrodes.

Upon the occasion of a failure of the PCSM test carried out by the PCSM circuit 462, PLD 1240 creates a PCSM_LED pulsating signal at output line 1313 which is buffered at device 1320 and filtered by a resistor within device 1322 in operative association with a capacitor of array 1324. The result is a buffered pulse, pulsating low true signal at line 1326 which is directed to the front panel LED 92 and the return from which is provided at line 1328 and resistor R227 coupled via line 1330 to +5V.

The handle interlock check LED 86 on console 64 is illuminated in response to the presence of the signal, HANDLE_LED at that terminal of PLD 1240 coupled with line 1315. Line 1315 is buffered as described in connection with FIG. 41E and returns as the signal, _LED_DRVOUT presented for filtering by a resistor within device 1322 in operative association with a capacitor of array 1324 to provide a filtered and buffered illuminating input at line 1334 which extends to console 64 front panel connector 1299. The return from that LED 80 extends via line 1336 and resistor R228 at line 1330 and +5V.

Power LED 84 is illuminated upon actuation switch 82, in turn, creating the +5V value at line 1330. This provides an input to line 1340 which is filtered at capacitor C158. The corresponding return at line 1342 is coupled to line 1344 and ground and is filtered at capacitor C159.

Upon being buffered and filtered, lines 1308–1313 are seen to be represented respectively at lines 1308a–1313a being directed to connector 1298 for application to the upper front panel of console 64. Lines 1308a–1312a additionally are tapped as represented respectively at lines 1308b–1312b for connection with connector 1300 which is directed to connector 67 and ultimately to the instrument 12 housing 14.

Lines 1316–1319 of the array 1296 extending from PLD 1240 carrying interlock data and switching signals from the instrument 12. In this regard, the above-noted interlock signal, INTERLOCK_ID, is one providing for the passage of current though a coding resistor mounted within the housing 14 to assure proper interconnection with connector 68 (FIG. 1). A protective network represented generally at 1346 is provided in conjunction with line 1316 as it extends to the connector 1300 operationally associated with connector 68. In this regard, the network 1346 incorporates diodes D102 and D103, resistors R231 and R232 and capacitor C162. A filter capacitor C163 is shown coupled with the connector 1300.

Line 1317 carries the signal representing an actuation of the energized/position switch 57 found upon instrument 12. That signal, identified as "ENGZ/POS_SW", is submitted from connector 1300 through a protective network represented in general at 1348 to PLD 1240. Network 1348 is identical to network 1346 and comprises clamping diodes D104 and D105, resistors R233 and R234 and capacitor C164. Next below line 1317 is line 1318 carrying the output signal, "ARM_SW" of the arm switch 56 mounted upon instrument 12. This signal is sent through a protective network identified generally at 1350 which is identical to network 1346 and comprises clamping diodes D106 and D107, resistors R235 and R236 and capacitors C165. Line 1319 carries the output of the capture switch 58 at instrument 12, which is identified as "CAPTURE_SW" and extends through protective network 1352 which is structured identically as network 1346. In this regard, network 1352 is comprised of clamping diodes D108 and D109, resistors R237 and R238 and capacitor C166.

Additionally submitted to housing assembly 14 via connector 1300 is +5V regulated power supply at line 1354 which is filtered by capacitor C163.

Looking to FIG. 41E, the four line array 1274 from PLD 1240 reappears extending to input terminals of a buffer circuit 1356 additionally extending to the input of device 1356 is earlier-described line 1315 which provides the signal, "_LED_DRVOUT" as discussed in connection with FIG. 41D at line 1332. The remaining four outputs of device 1356, representing buffered signals from array 1274 are shown as line array 1358 which is directed to relays of the PCSM circuit.

Figure 42:
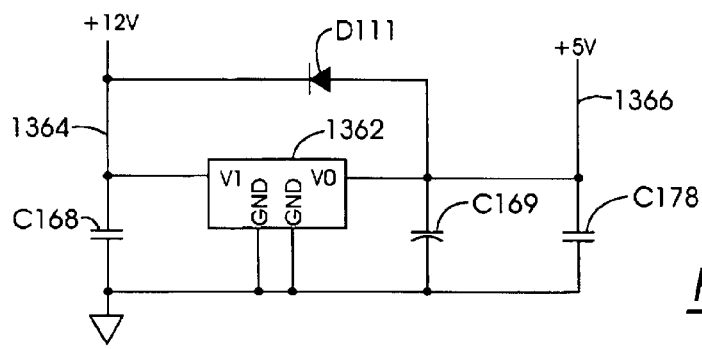
FIG. 42 is an electrical schematic diagram of a power supply.

The +5V regulated power supply discussed in connection with FIGS. 41A–41E is derived by the circuit illustrated in FIG. 42. Looking to that figure, a type LM2940CT-5.0 regulator marketed by National Semiconductor, Inc. of Sunnyvale, Calif. is shown at 1362 coupled to +12V input at line 1364 and configured with capacitors C168–C170 and diode D111 to provide the noted regulated +5V supply at line 1366. The +12V input is derived as discussed in connection with FIG. 47.

Referring to FIG. 43, a network for determining the presence of a low voltage power supply under-voltage condition as presented to PLD 1240 at line 1294 is represented. Looking to the figure, the above-noted +12V power supply is treated and reduced by a network including resistor R240, capacitor C172, diode D113 and passive operational amplifier 1368 having a feedback configured output at line 1370 directed to one input of a comparator 1372. Comparator 1372 may be a type LM358D marketed by National Semiconductor, Inc. (supra). The reference input to comparator 1372 is derived at a divider network coupled to the +12V supply and configured with resistors R241–R243 and capacitor C173 to provide a reference input at line 1374. Device 1372 is configured with +5V input and capacitor C174 to provide a low logic true output at line 1294 in the event of an under-voltage condition. Note in this regard that line 1294 is coupled through pull-up resistor R224 to +5V supply.

Figure 44:
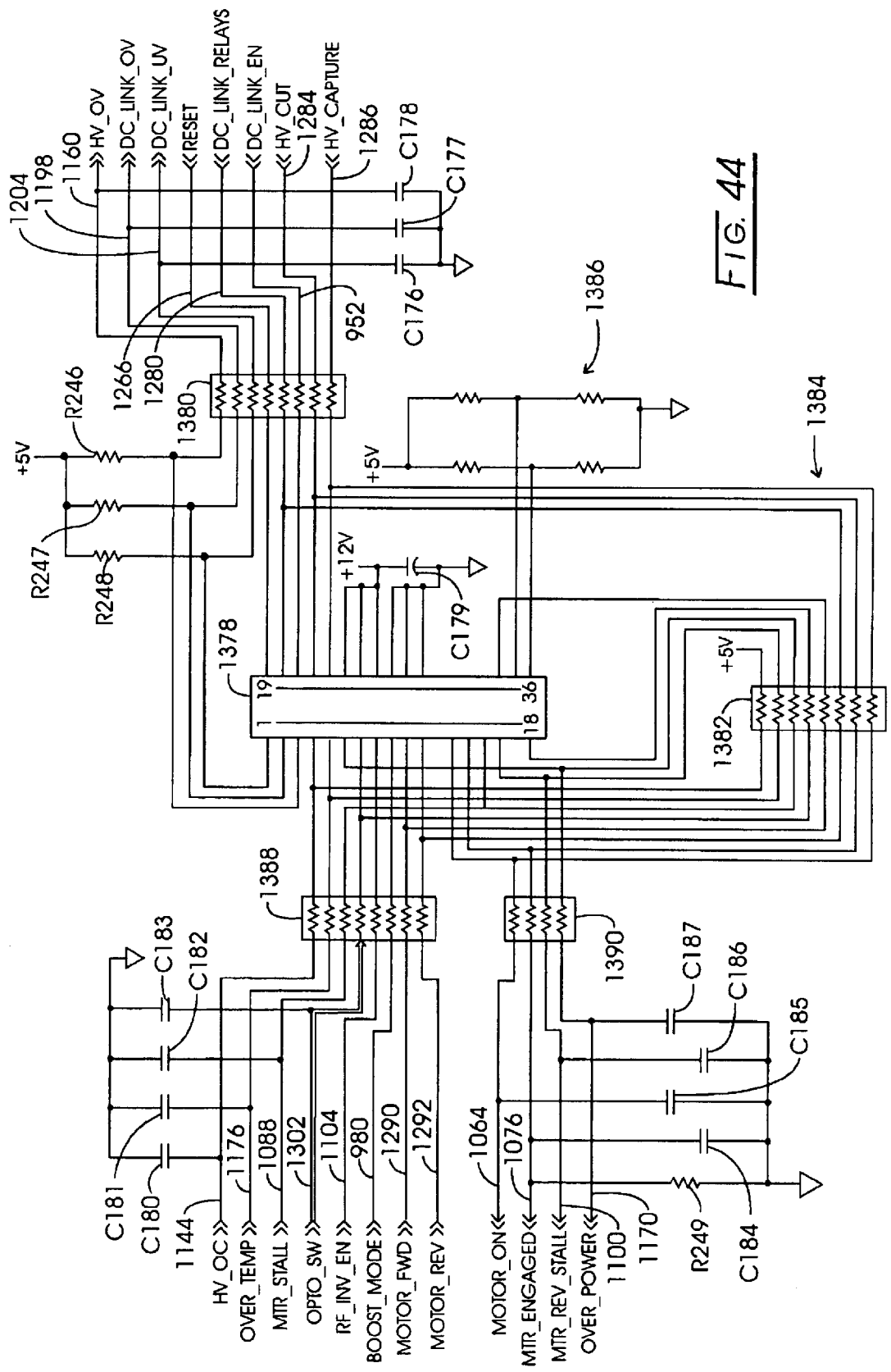
FIG. 44 is an electrical circuit diagram illustrating the treatment of PLD signal inputs and outputs.

Referring to FIG. 44, a filtering network is revealed which provides an RC filtering of the inputs and outputs associated with PLD 1240 and submits those filter signals along with power supply inputs to a connector 1378 distributing the signal to the earlier discussed mother board or power board. In the figure, the high voltage over-voltage signal, the d.c. link voltage over-voltage signal and the d.c. link voltage under-voltage signal at respective lines 1160, 1198 and 1204 are received from connector 1378 and coupled via respective pull-up resistors R246–R248 to +5V source. Additionally, the signals so received are filtered by the discrete resistors of a multi-resistor component 1380 and respective filter capacitors C176–C178.

Line 1266, carrying the reset output; line 1280 carrying the high voltage precursor electrode energization command signal; and line 952 carrying the high voltage capture command signal are each treated by discrete resistors within multi-resistor component 1380. Lines 952, 1284 and 1286 additionally are coupled to +5V source through a pull-up resistor within multi-resistor component 1382 as provided by three line array 1384. Divided voltages are provided from resistor array 1386 to the connector 1378 and +12V source and ground inputs are submitted to the connector from opposite sides of capacitor C179.

The high voltage over-current signal at line 1144; the over-temperature signal at line 1176; the motor forward stall signal at line 1088; and the footswitch and vacuum switch actuation signals represented in general at arrow 1302 labeled "OPTO_SW" are filtered by discrete resistors within multi-resistor component 1388 and respective capacitors C180–C183. Of this line grouping, lines 1144, 1176 and the footswitch and vacuum switch lines represented in general at 1302 are coupled through discrete pull-up, resistors within component 1382 to +5v source.

The RF inverter enable command; boost mode command; motor forward command; and motor reverse command are treated by discrete resistors within multi-resistor component 1388. Of this grouping, lines 1290 and 1292 are coupled to +5V source through pull-up resistors within multi-resistor component 1382.

The motor on input; motor engaged input; motor reverse stall; and the over power input are treated by discrete resistors within a multi-resistor component 1390. Of these lines, lines 1064 and 1076 additionally are coupled to +5V source through discrete pull-up resistors within multi-resistor component 1382. Line 1076 is coupled through filter resistor R249 and filter capacitor C184 to ground. Lines 1064, 1100 and 1170 are coupled through respective filter capacitors C185–C187 to ground.

Figure 45:
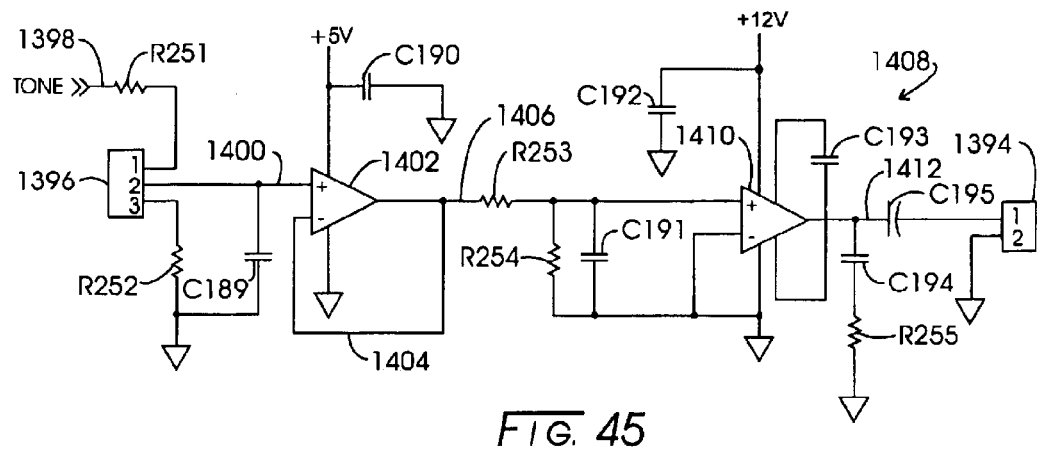
FIG. 45 is an electrical circuit diagram of an audio control.

Referring to FIG. 45, the circuit driving a speaker within console 64 and adjusting its volume with a potentiometer is revealed. The line pair from this speaker (not shown) is coupled with a connector shown at 1394. Correspondingly, a potentiometer (not shown) derived volume control is applied to an opposite connector 1396.

The PLD derived tone signal line 1398 (FIG. 41A) reappears in the instant figure and is asserted via resistor R251 to the noted potentiometer in conjunction with line 1344 and resistor R252 via connector 1396. A volume input, filtered at capacitor C158, is then provided at line 1400. Line 1400 is directed to an amplification stage including operational amplifier 1402 configured with +5V regulated power supply, capacitor C190 and feedback line 1404. An output is provided at line 1406 incorporating resistor R253 and extending to an oscillator network represented generally at 1408 including a type LM386N-1 amplifier component 1410 configured with resistors R254 and R255, capacitors C191–C195 and +12V power supply to provide a tone output at line 1412. That tone output is provided whenever an electrosurgical cutting is taking place either by the precursor electrodes or the pursing cables. Additionally, the tone is pulsed in the event of a failure occurring within the PCSM testing of dispersive return electrode 70. Amplifiers as at 1410 are marketed by Analog Devices, Inc. of Norwood, Mass.

Figure 46A:
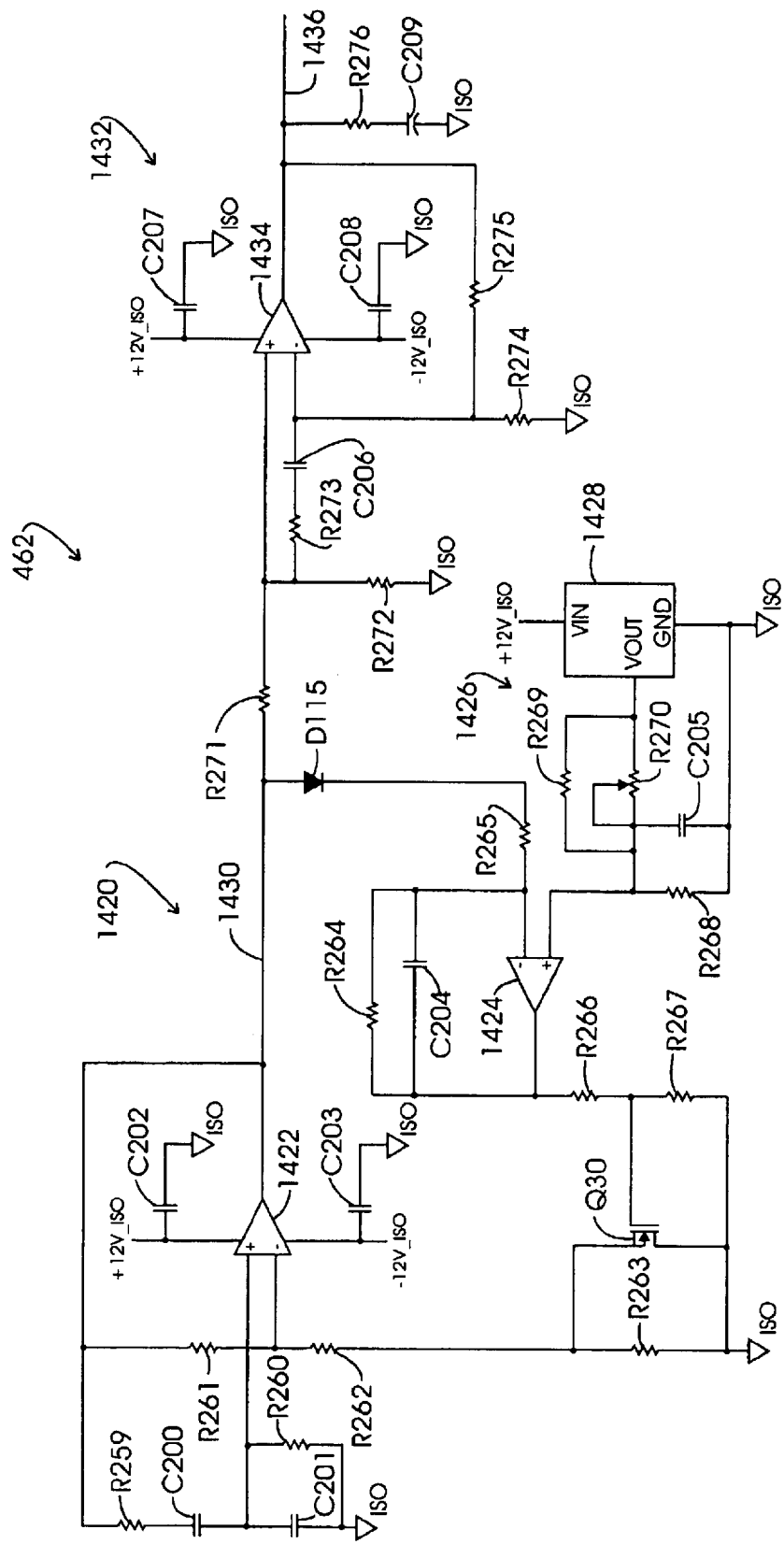
FIGS. 46A–46C combine as labeled thereon to describe frequency generation and test switching components of a PCSM circuit.
Figure 46B:
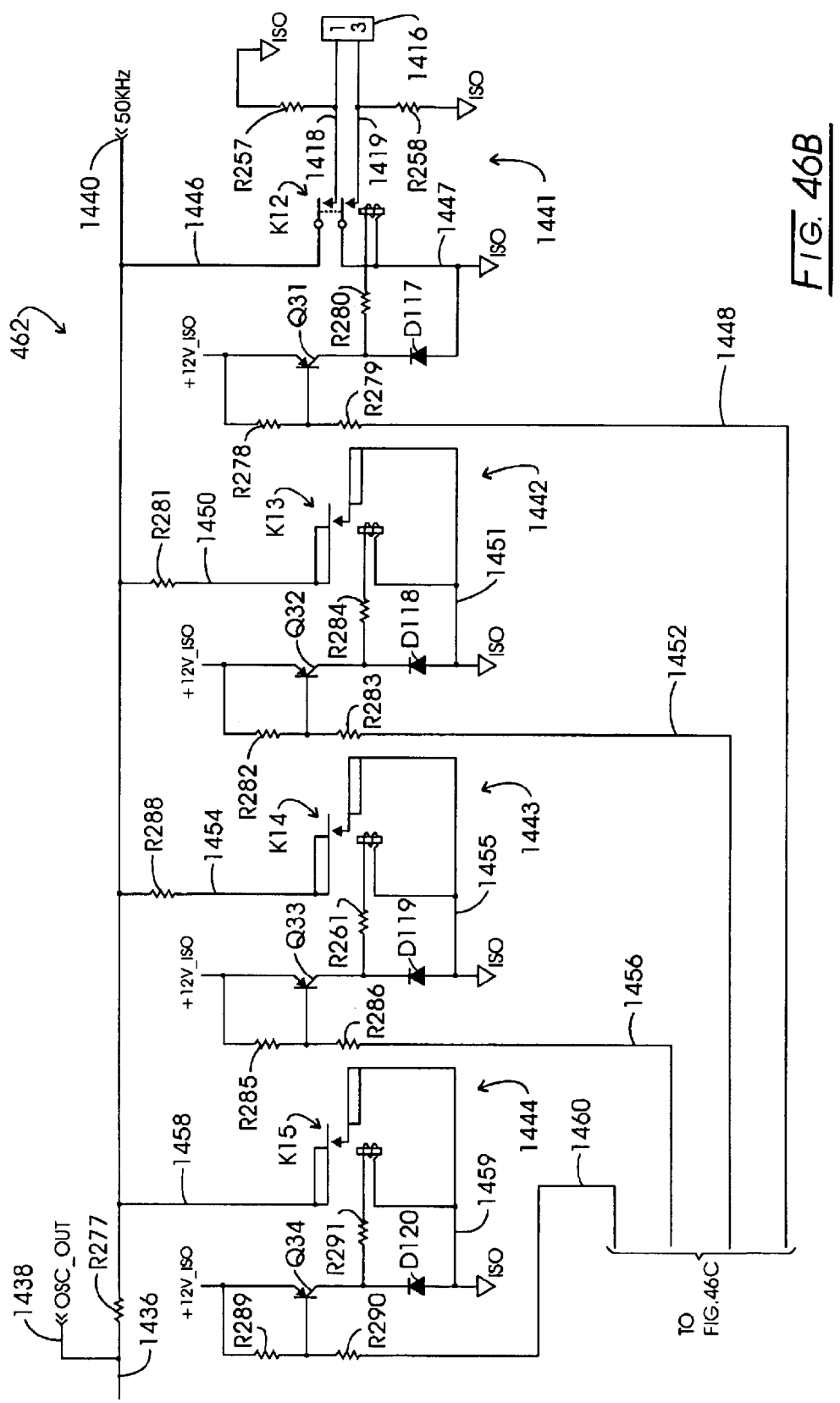
Figure 46C:
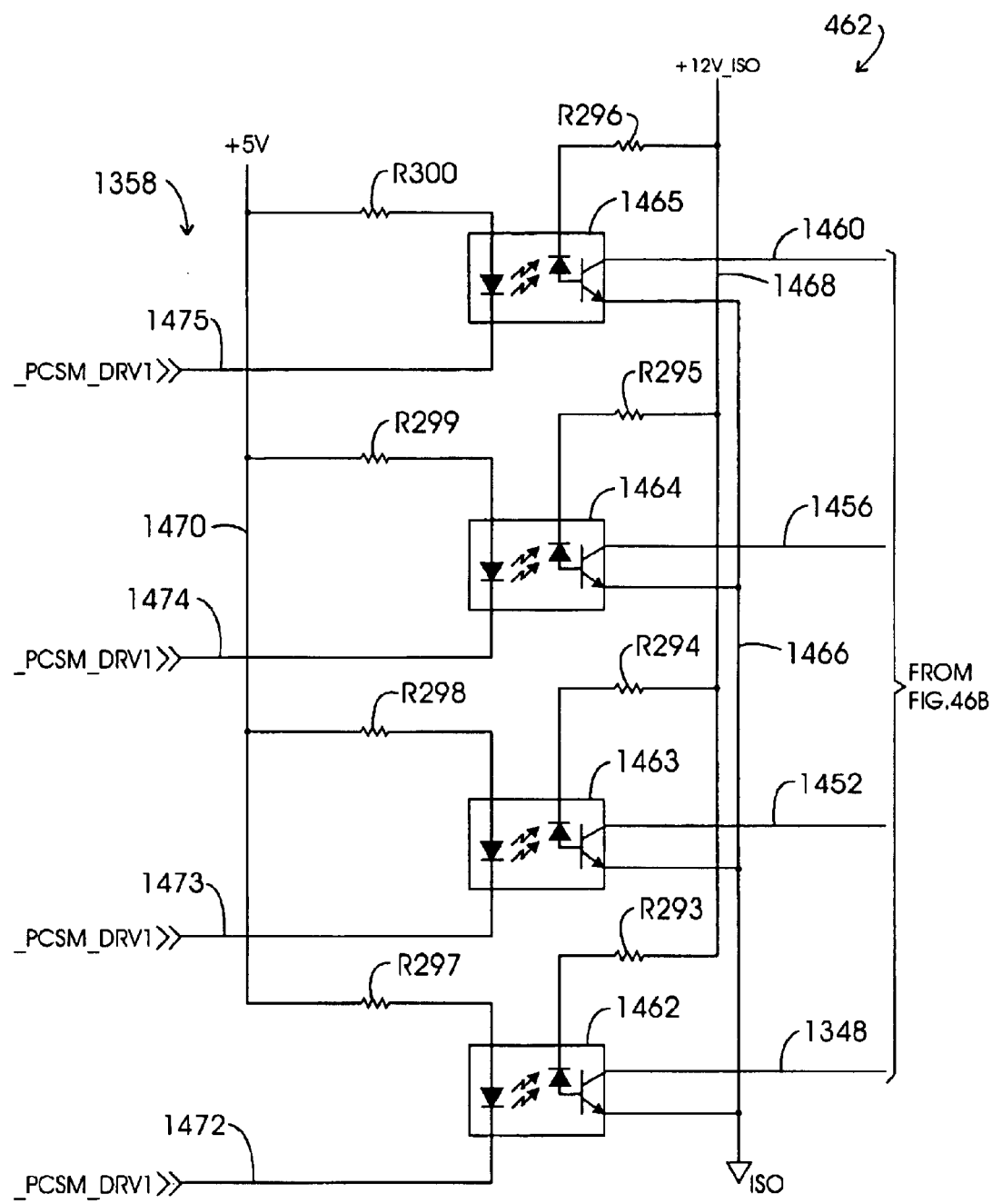

FIGS. 46A–46C should be considered together in the manner labeled thereon. These figures illustrate the test signal generation and switching involved in self testing and fault testing with respect to the dispersive return electrode 70. The circuit shown is a component of the PCSM circuit described in conjunction with block 462 in FIG. 15. This PCSM test is carried out at the very commencement of the procedure and failure of the test will prohibit the procedure from being carried out along with the development of pulsed warning signals of both aural and visible variety, the latter cue being a flashing of the red LED 92 (FIG. 1). In general, the instant circuit carries out a self test upon initial powering up with the actuation of switch 82. Later, upon actuation of switch 92, the testing of the dispersive electrode 70 is carried out.

Looking to FIG. 46B, a connector 1416 is provided which functions to connect with lines 464 and 466 as described in connection with FIG. 15. Connection RE1 is represented in FIG. 46B at line 1418 which is coupled through resistor R257 to ground. Connection RE2 is represented at line 1419 which is connected through resistor R258 to ground. The circuits represented by RE1 and RE2, in general, extend from the electrode pads 72 and 74 (FIG. 1) to return to the high voltage output stage 450 but are tapped for the instant testing purposes. PCSM circuit 462 functions to impress about a 50 KHz low voltage signal across pads 72 and 74 to verify that dispersive return electrode 68 is properly connected to the patient. In general, the testing evaluates with respect to a resistance tolerance, for example, between about 20 and 80 ohms. A resistance representation less than the former indicates a shorting condition and a resistance above the latter represents a non-connection. Those resistance values may be varied in accordance with the desires of the designer.

Looking to FIG. 46A, the oscillator network deriving the above-noted 50 KHz frequency is represented in general at 1420. Network 1420 is comprised of operational amplifier 1422 configured in conjunction with resistors R259–R263; capacitors C200–C203; complimentary amplifier 1424 configured with resistors R264–R267; capacitor C204 and the potentiometer frequency adjusting network 1426; a power supply input 1428; transistor Q30 and diode D115. Potentiometer 1426 is configured in conjunction with capacitor C205 and resistor components R258–R270. Input device 1428 may be provided as a type REF-02C/AD marketed by Analog Devices, Inc. of Norwood, Mass. The 50 KHz output developed by network 1420 is provided at line 1430 and is directed through input resistor R271 to an amplification stage represented generally at 1432 functioning to adjust the 50 KHz signal to about 7V, RMS or 12V peak-to-peak. Stage 1432 is implemented with an operational amplifier 1434 configured with resistors R272–R275 and capacitors C206–C208. The treated 50 KHz output is provided at line 1436 which is filtered at resistor R276 and capacitor C209. Looking again to FIG. 46B, line 1436 is seen to be tapped at line 1438 to provide an "OSC_OUT" signal. Following the tap at line 1438, line 1436 incorporates a resistor R277 having a value of about 50 ohms and extends to an oppositely disposed tap identified at 1440, labeled "50 KHz". Extending between taps 1438 and 1440 is a sequence of four relay implemented networks represented in general at 1441–1444.

Looking to network 1441, relay K12 is seen to be connected between lines 1446 and 1447. It is actuated by PLD 1240 by a signal ultimately developed at line 1448 incorporating resistors R278 and R279 and extending to the gate of pnp transistor Q31. Transistor Q31 is configured with diode D117 and resistor R280 to energize the solenoid component of relay K12 in response to a signal impressed from line 1448. This functions to couple the 50 KHz signal at line 1436 and ground to respective lines 1418 and 1419 to carry out the PCSM test. As noted above, this test occurs upon practitioner actuation of start/reset switch 92 (FIG. 1).

Looking to relay network 1442, relay K13 is connected between lines 1450 and 1451, the latter extending to ground and the former incorporating a 200 ohm resistor R281. Relay K13 is closed in response to an actuation signal imposed ultimately from PLD 1240 at line 1452. Line 1452 incorporates resistors R282 and R283 and is connected to the gate of pnp transistor Q32. Transistor Q32 is configured with diode D118 and resistor R284 to effect the energization of the solenoid component of relay K13, closing it and connecting a 50 KHz signal at line 1436 through resistor R281 to ground to provide a high resistance self test. Looking to relay network 1443, relay K14 is seen to be connected with the 50 KHz signal at line 1436 by line 1454 and with ground via line 1455. Line 1454 incorporates a 49.9 ohm resistor R288. A solenoid component of relay K14 is energized to close the relay in response to a signal from PLD 1240 ultimately presented at line 1456. Line 1456 incorporates resistors R285 and R286 and extends to the gate of pnp transistor Q33. Transistor Q33 is configured in conjunction with diode D119 and resistor R287 to energize the solenoid component of relay K14 when turned on in response to the signal at line 1456. This diverts the 50 KHz signal across the 49.9 ohm resistance at resistor R288 from line 1436 to ground.

Looking to relay network 1444, relay K15 is seen to be coupled between line 1458 connected to line 1436 and line 1459 coupled to ground. The solenoid component of relay K15 is energized upon the occurrence of a signal ultimately derived from PLD 1240 and asserted at line 1460. Line 1460 incorporates resistors R289 and R290 and is coupled to the gate of pnp transistor Q34. Transistor Q34 is configured with diode D120 and resistor R291 to energize the solenoid component of relay K15 upon being turned on from line 1460. This couples line 1436 to ground through lines 1458 and 1459, providing a self test representing a short circuit.

Referring to FIG. 46C, actuation lines 1448, 1452, 1456, and 1460 are seen to be coupled to the collector output stages of respective opto-couplers 1462–1465. The emitter components of the outputs of couplers 1462–1465 are coupled to ground via line 1466 and each coupler is coupled with +12V source through respective resistors R293–R296 and line 1468. The anode inputs to opto-couplers 1462–1465 are coupled through respective resistors R297–R300 to +5V source at line 1470, while the cathode side inputs thereof are coupled with respective input lines 1472–1475. These input lines 1472–1475 are components of the line array 1358 discussed in connection with FIG. 41E which provides a buffering of outputs of line array 1274 extending from PLD 1240. Thus, the return electrode 70 test as well as the PCSM self test are carried out under the command of PLD 1240. It may be noted that relay K15 of network 1444 is energized to short the signal at line 1436 during those intervals where the test asserted from networks 1441–1444 are not being carried out, even though relay K12 will be open.

Figures 47, 48B:
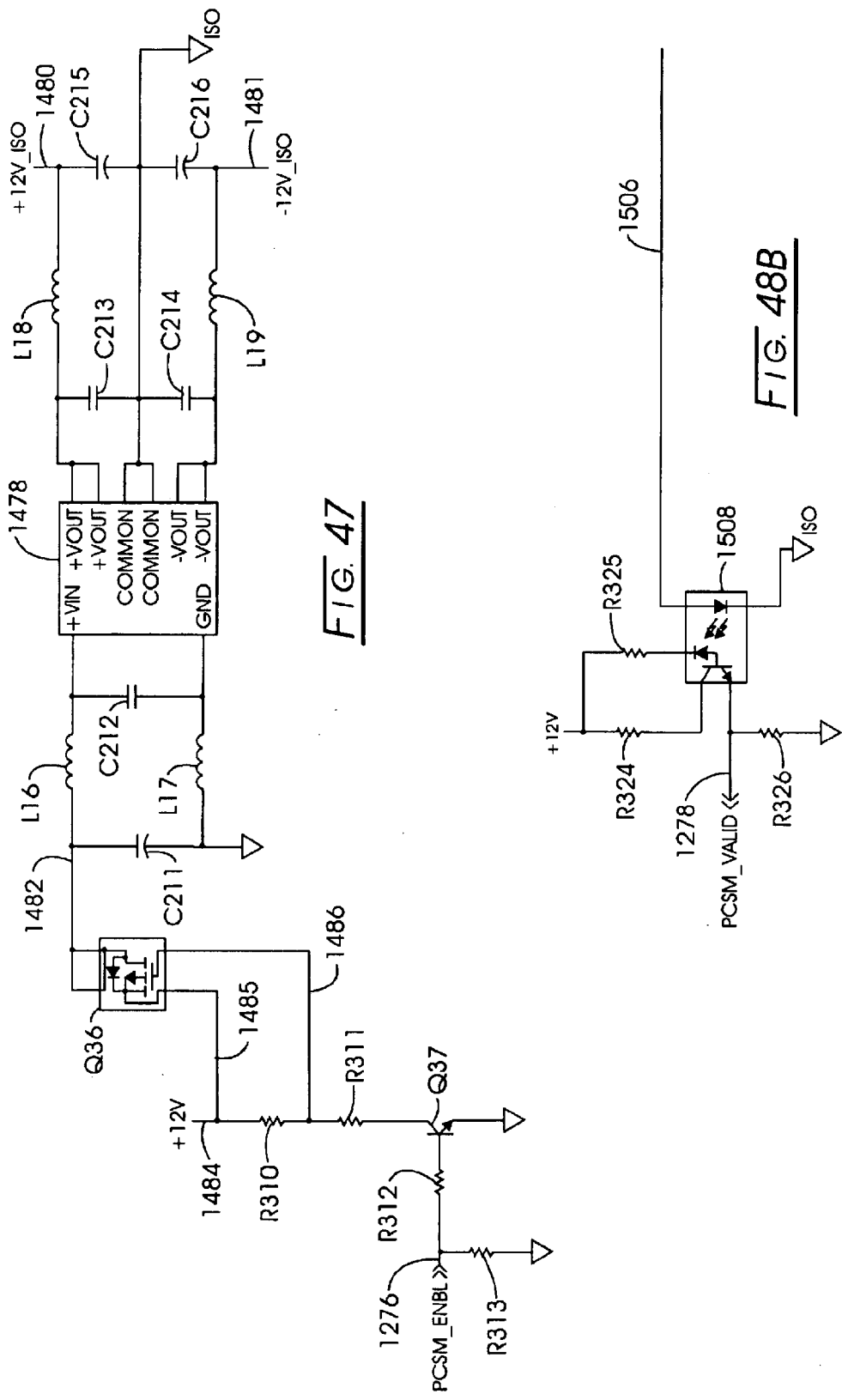
FIG. 47 is an electrical schematic diagram of a power supply.
FIGS. 48A and 48B combine as labeled thereon to illustrate a circuit for carrying out a window-based analysis of a return electrode test.

Referring to FIG. 47, an isolated power supply utilized to generate the noted +12V is illustrated. This power supply is configured about a supply component 1478 which may be provided as a type NMS1212 device marketed by Newport Components of Milton Keynes, GB. In effect, device 1478 converts +12V to +12V and −12V. It is configured with inductors L16–L19 and capacitors C211–C216 to provide an isolated +12V at output 1480 and an isolated −12V at output 1481. Device 1478 is provided +12V input at line 1482 from power transistor Q36, the source of which is coupled to +12V from lines 1484 and 1485 and the gate terminal of which is coupled with line 1486 to line 1484. Line 1484 incorporates resistors R310 and R311 and is coupled with the collector of npn transistor Q37, the emitter of which is connected to ground. Transistor Q37 is gated on to enable the power supply 1478 by a PCSM_ENBL signal asserted from PLD 1240 at line 1276 through base resistor R312. Line 1276 is coupled through resistor R313 to ground and is seen extending from PLD 1240 in FIG. 41A.

Figure 48A:
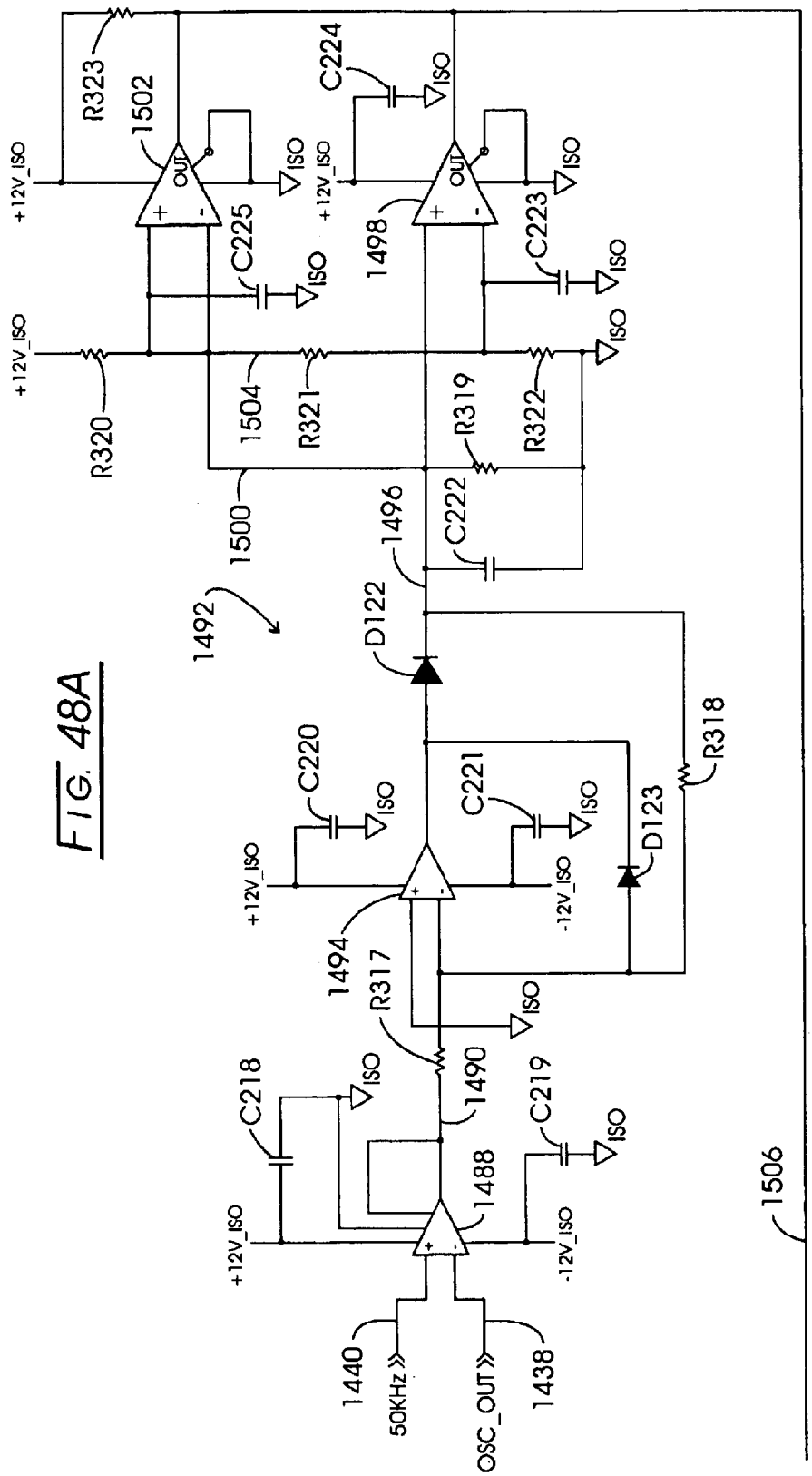

Referring to FIGS. 48A and 48B which should be considered in the orientation as labeled thereon, a window defining detection or comparison circuit is illustrated which evaluates the actual PCSM test from network 1441 (FIG. 46B) as well as the self test of networks 1442–1444. In general, the ohmic window representing a valid dispersive electrode 70 connection will reside between about 20 and 80 ohms. Referring to FIG. 48A, the taps 1338 and 1440 as described in connection with FIG. 46B are shown to extend to the inputs of a differential amplifier 1488. Amplifier 1488 may be a type AMP02FS device marketed by Analog Devices, Inc. of Norwood, Mass. and is implemented with +12V and −12V and capacitors C218 and C219. Thus configured, device 1488 responds to the floating signal at resistor R277 (FIG. 46B) and provides a single ended signal to ground at output line 1490. This a.c. signal at line 1490 then is submitted through input resistor R317 to a precision rectifier represented in general at 1492. Rectifier 1492 provides rectification without diode drop phenomena and is seen to comprise operational amplifier 1494 configured with resistor R318, diodes D122 and D123 and capacitors C220 and C221. The d.c. signal at output line 1496 then is proportional to the current in the return electrode or to the test evaluations from networks 1442–1444 and is impressed across capacitor C222. A resistor R319 extends between line 1476 and ground and functions for the selective discharge of capacitor C222.

The d.c. signal at line 1496 is directed to the positive input of a comparator 1498 and via line 1500 to the negative input of a corresponding comparator. Reference inputs to these comparators 1498 and 1502 are provided from line 1504 and +12V which incorporates reference level defining resistors R320–R322. The reference inputs are seen to be connected additionally with filtering capacitors C223 and C225, while the +12V input to comparator 1498 is filtered at capacitor C224. Comparators 1498 and 1502 may be provided as type LM319N devices as marketed by National Semiconductor, Inc. of Sunnyvale, Calif.

When the current represented at line 1496 corresponds with the resistance falling within a window defined between a lower threshold of, for example, 20 ohms and an upper limit of, for example, 80 ohms, then a positive voltage signal will be impressed from resistor R313 at line 1506. Looking to FIG. 48B, line 1506 is seen to extend to the anode of the input side of an opto-coupler 1508. The collector component of the output of opto-coupler 1508 is coupled with +12V through resistors R324 and R325, while the emitter output thereof is provided at line 1278 which is coupled through resistor R326 to ground. Line 1278 serves to apply the signal thereat representing a valid test, "PCSM_VALID" to PLD 1240 as shown in FIG. 41A.

Since certain changes may be made in the above apparatus and method without departing from the scope of the invention herein involved, it is intended that all matter contained in the above description or shown in the accompanying drawings shall be interpreted as illustrative and not in a limiting sense.

What is claimed is:

1. An electrosurgical generator connectable with a power input, comprising:
   an input treatment network responsive to said power input to provide a first output;
   a frequency generator responsive to said first output and to a frequency control input to derive an output having a predetermined waveform;
   an output power control circuit responsive to a voltage level control input and a power level control input to derive an electrosurgical energy output at an electrosurgical voltage level and power level at an electrosurgical frequency;
   an output stage responsive to said output power control circuit electrosurgical energy output and connectable in electrical communication with an electrosurgical instrument; and
   a control assembly responsive to a cut command to derive said voltage level control input to provide a boost electrosurgical voltage level for a boost interval and thereafter responsive to derive said power level control input in a tissue load resistance defined output voltage monitoring mode or an output power mode to effect a normal cut electrosurgical voltage level which is less than said boost electrosurgical voltage level.

2. The electrosurgical generator of claim 1 in which said boost electrosurgical voltage level is greater than said normal cut electrosurgical voltage level by about a 1.2 to about a 1.5 factor.

3. The electrosurgical generator of claim 1 in which said boost interval is about 100 to about 1000 milliseconds.

4. The electrosurgical generator of claim 1 in which said boost interval is about 250 to about 500 milliseconds.

5. The electrosurgical generator of claim 1 in which said control assembly derives said voltage level control input to provide a said boost electrosurgical voltage level of about 1000 volts, peak-to-peak, to about 2000 volts, peak-to-peak.

6. The electrosurgical generator of claim 1 in which said control-assembly derives said voltage level control input to provide a said boost electrosurgical voltage level of about 1200 volts, peak-to-peak, to about 1500 volts, peak-to-peak.

7. The electrosurgical generator of claim 5 in which said control assembly derives said voltage level control input to provide a said normal cut electrosurgical voltage level of about 700 volts, peak-to-peak, to about 1200 volts, peak-to-peak.

8. The electrosurgical generator of claim 6 in which said control assembly derives said voltage level control input to provide a said normal cut electrosurgical voltage level of about 800 volts, peak-to-peak, to about 1000 volts, peak-to-peak.

9. The electrosurgical generator of claim 1 in which said input treatment network comprises:
   a boost converter network responsive to a converter control input to derive said first output at an interim voltage level of first value; and
   a converter control network responsive to said power input and to said interim voltage level to derive a said converter control input effective to provide power factor correction.

10. The electrosurgical generator of claim 1 in which:
    said output voltage control circuit includes a relay switch responsive to a relay control input to terminate said electrosurgical energy output; and
    said control assembly is responsive to a fault condition to derive said relay control input.

11. The electrosurgical generator of claim 10 comprising:
    a high voltage monitor responsive to said electrosurgical energy output to derive a high voltage monitor signal; and
    said control assembly is responsive to derive said relay control input when said high voltage monitor signal exceeds a high voltage threshold level.

12. The electrosurgical generator of claim 11 in which said control assembly is responsive in the presence of a said voltage level control input providing a boost electrosurgical voltage level to disable said relay control input.

13. The method for generating an electrosurgical cutting arc at an electrode confronting animal tissue comprising the steps of:
    providing an input treatment network responsive to an applied source of electrical power to derive a first output;
    providing a link inverter containing network responsive to said first output to derive a link voltage of controllable amplitude;
    providing an R.F. inverter network responsive to said link voltage to generate an R.F. output of predetermined electrosurgical cutting frequency and exhibiting an inverter voltage level corresponding with said link voltage controllable amplitude;
    stepping up said inverter voltage level to derive an electrosurgical cutting output at an electrosurgical cutting power level;
    commencing the application of said electrosurgical output to said electrode and continuing said application thereafter;
    monitoring the voltage level of said electrosurgical output to provide an output voltage monitor signal;
    monitoring the power level of said electrosurgical output to provide an output power monitor signal;
    comparing said output voltage monitor signal with a reference representing a target value of said voltage level to derive a voltage mode program control signal;
    comparing said output power monitor signal with a reference representing a target value of output power level to derive a power mode program control signal; and
    controlling said link inverter containing network by applying a program control signal thereto, said program control signal comprising either said voltage mode program control signal or said power mode program control signal.

14. The method of claim 13 in which:
    said step of monitoring said voltage level of said electrosurgical output monitors said electrosurgical cutting voltage level to provide said output voltage monitor signal as a high voltage monitor signal;
    said step of comparing said output voltage monitor signal with a reference carries out said comparison employing a predetermined electrosurgical cutting voltage level as said target value; and
    said step of controlling said link inverter containing network is carried out by applying said program control signal thereto at a slow rate effective to avoid oscillation of said electrosurgical cutting output.

15. The method of claim 14 in which said step for controlling said link inverter applies said program control signal under low bandwidth conditions.

16. The method of claim 14 including the steps of:
    monitoring said link voltage controllable amplitude to provide a link voltage controlling feedback signal; and further controlling said link inverter containing network by applying said feedback signal to said link inverter containing network at a rate faster than said slow rate.

17. The method of claim 16 in which said step for further controlling said link inverter containing network applies said feedback signal at a high gain.

18. The method of claim 13 in which said step of controlling said link inverter containing network applies said program control signal when commencing said application of said electrosurgical output in a manner effecting derivation of said link voltage at a boost level for a boost interval effective to cause generation of a said electrosurgical cutting arc when said electrode is in contact with said tissue.

19. The method of claim 18 in which said step of controlling said link inverter containing network provides said boost level for a fixed said boost interval.

20. The method of claim 19 in which said fixed boost interval is about 0.5 second.

21. The method of claim 19 in which said fixed boost interval is about three eighths second.

22. The method of claim 18 in which said step of controlling said link inverter containing network applies said program control signal to derive said link voltage at a said boost level for said boost interval and thereafter applies said program control signal to derive said link voltage at a cut level less than said boost level and effective to sustain the formation of an arc at said electrode.

23. The method of claim 22 in which said cut level corresponds with a power value of said application of said electrosurgical output which is about one-half the power value of said electrosurgical output when at said boost level.

24. The method of claim 13 including the steps of
monitoring select electrical parameter monitors, said electrosurgical cutting voltage level and the electrosurgical current corresponding therewith to provide said output power monitor signal;
said step of comparing said output power monitor signal with a reference carries out said comparison employing a predetermined value of power as said target value; and
said step of controlling said link inverter containing network is carried out by applying said program control signal thereto.

25. The method of claim 24 in which said step of controlling said link inverter containing network applies said program control signal when commencing said application of said electrosurgical output in a manner effecting derivation of said link voltage at a boost level for a boost interval effective to cause generation of a said electrosurgical cutting arc when said electrode is in contact with said tissue.

26. The method of claim 25 in which said step of controlling said link inverter containing network provides said boost level for a fixed said boost interval.

27. The method of claim 26 in which said fixed boost interval is about 0.5 second.

28. The method of claim 26 in which said fixed boost interval is about three eighths second.

29. The method of claim 25 in which said step of controlling said link inverter containing network applies said program control signal to derive said link voltage at a said boost level for said boost interval and thereafter applies said program control signal to derive said link voltage at a cut level less than said boost level and effective to sustain the formation of an arc at said electrode.

30. The method of claim 29 in which said cut level corresponds with a power value of said application of said electrosurgical output which is about one-half the power value of said electrosurgical output when at said boost level.

31. The method of claim 13 in which said step of providing an input treatment network provides a power factor correction with respect to said applied source of electrical power and derives said first output as a regulated d.c. voltage.

32. The method of claim 13 in which said step of providing a link inverter containing network provides said link inverter containing network as including an inverter control network effecting a resonant transition phase shift control of said link inverter and further including a rectifier for providing said link voltage as a d.c. link voltage.

33. The method for generating an electrosurgical cutting arc at an electrode configured for cutting tissue, exhibiting a range from human tissue resistances comprising the steps of:
providing an input treatment network responsive to an applied source of electrical power to derive a first output;
providing a frequency generator containing network responsive to said first output and to a control input to derive a second output having a tissue cutting waveform;
providing an output stage responsive to said second output and connectable in electrical communication with said electrode for applying electrosurgical energy thereto at a first level of voltage effective to create said arc and subsequently at a second level of voltage less than said first level of voltage effective to sustain said created arc; and
controlling said frequency generator containing network to derive said first level of voltage at the commencement of said application of said electrosurgical energy to said electrode for a boost interval effective to create said cutting arc, and thereafter to derive said second level of voltage effective to generate said electrosurgical cutting arc at a substantially constant power across said range of human tissue resistances.

34. The method of claim 33 in which said step of controlling said frequency generator containing network provides said first voltage level as being greater than said second voltage level by about a 1.2 to about 1.5 factor.

35. The method of claim 33 in which said step of controlling said frequency generator containing network provides a fixed said boost interval of about 0.5 seconds.

36. The method of claim 33 in which said step of controlling said frequency generator containing network provides a fixed said boost interval of about three eighths second.

37. The method of claim 33 in which said step of controlling said frequency generator containing network provides said first level as voltage between about 1000 volts, peak-to-peak, and about 2000 volts, peak-to-peak.

38. The method of claim 33 in which said step of controlling said frequency generator containing network provides said first level as voltage between about 1200 volts, peak-to-peak and about 1500 volts peak-to-peak.

39. The method of claim 37 in which said step of controlling said frequency generator containing network provides said second level of voltage between about 700 volts, peak-to-peak and about 1200 volts, peak-to-peak.

40. The method of claim 37 in which said step of controlling said frequency generator containing network provides said second level of voltage between about 800 volts, peak-to-peak and about 1000 volts, peak-to-peak.

41. An electrosurgical generator, connectible with a power input, comprising:
an input treatment network responsive to said power input to derive an interim voltage output of first value;

a first inverter network responsive to said interim voltage and to a first inverter control input to derive a first alternating voltage output of second value less than said first value at a first inverter output;

a first inverter control network coupled with said first inverter network and deriving said first inverter control input;

a rectifier network responsive to said first alternating voltage output to derive a link output at a d.c. voltage level corresponding with said first alternating voltage output second value;

a second inverter network having an input, and responsive to said link output to derive a second alternating voltage output at an electrosurgical frequency value and with voltage amplitudes established by said link output d.c. voltage level;

a second inverter control network coupled with said second inverter network to effect derivation of said second alternating voltage output electrosurgical frequency;

a high voltage transformer having a primary side responsive to said second alternating voltage output and a secondary side deriving an electrical cutting energy input at an electrosurgical voltage level and at said electrosurgical frequency;

an output stage coupled with said high voltage transformer secondary side and connectable in electrical communication with an electrosurgical instrument;

a high voltage monitor responsive to said electrical cutting energy input to derive a high voltage monitor signal;

a high voltage current monitor responsive to said electrical cutting energy input to derive a high voltage current monitor signal;

said first inverter control network includes:

a power derivation network responsive to said high voltage monitor signal and said high voltage current monitor signal to derive a monitored power signal;

a first comparator network responsive to a power reference and to said monitored power signal to derive a lower load resistance defined first program signal;

a second comparator network responsive to a voltage reference and to said high voltage monitor signal to derive a higher load resistance defined second program signal; and a controller network responsive to said first or second program signal of load resistance defined to derive said first inverter control input.

42. The electrosurgical generator of claim 41 in which said first inverter control network derives said first inverter control input to effect a resonant transition phase shift control of said first inverter network.

43. The electrosurgical generator of claim 41 in which said first inverter control network comprises:

a power monitoring circuit responsive to said electrical cutting energy input to derive a program signal; and a controller network responsive to said program signal to derive said first inverter control input.

44. The electrosurgical generator of claim 41 in which said power derivation network comprises:

a multiplier circuit responsive to said high voltage monitor signal and to said high voltage current monitor signal to derive a product output; and an integrator network responsive to said product output to derive said monitored power signal.

45. The electrosurgical generator of claim 41 comprising:

a control assembly actuable to derive a boost voltage signal for a boost interval; and said first inverter control network is responsive to said boost voltage signal to derive a said first inverter control input effecting derivation of said first alternating voltage output second value at a boost voltage value, and is responsive thereafter to derive said first inverter control input effecting derivation of said first alternating voltage output second value at a normal cut voltage value less than said boost voltage value.

46. The electrosurgical generator of claim 45 in which said boost voltage value is greater than said normal cut voltage value by a factor within a range from about 1.2 to about 1.5.

47. The electrosurgical generator of claim 41 including an isolation transformer having a primary side coupled with said first alternating output and a secondary side providing said first alternating voltage output to said rectifier network.

48. The electrosurgical generator of claim 41 in which said second inverter network comprises a resonant tank circuit.

49. The electrosurgical generator of claim 46 in which said boost interval is about 100 to about 1000 milliseconds.

50. The electrosurgical generator of claim 46 in which said boost interval is about 250 to 750 milliseconds.

51. The electrosurgical generator of claim 46 in which said boost voltage value effects derivation of a said electrosurgical voltage level of about 1000 volts peak-to-peak to about 2000 volts peak-to-peak.

52. The electrosurgical generator of claim 46 in which in which said boost voltage value effects derivation of a said electrosurgical level of about 1200 volts, peak-to-peak to about 1500 volts, peak-to-peak.

53. The electrosurgical generator of claim 51 in which said normal cut voltage value effects derivation of said electrosurgical cutting voltage level of about 700 volts, peak-to-peak to about 1200 volts, peak-to-peak.

54. The electrosurgical generator of claim 52 in which said normal cut voltage value effects derivation of said electrosurgical cutting voltage level of about 800 volts, peak-too-peak to about 1000 volts, peak-to-peak.

55. The electrosurgical generator of claim 41 in which said input treatment network comprises:

a boost converter network responsive to a converter control input to derive said interim voltage of first value; and a converter control network responsive to said power input and to said interim voltage first value to derive a said converter control input effective to provide power factor correction.

56. The electrosurgical generator of claim 41 comprising:

a relay switch connected between said rectifier network and said second inverter network input and responsive to a relay control input to convey or terminate conveyance of said link output to said second inverter network; and a control assembly responsive to a fault condition to derive a said relay control input terminating conveyance of said link output to said second inverter network input.

57. The electrosurgical generator of claim 56 in which:

said first inverter control network comprises a power monitoring circuit responsive to said electrical cutting energy input to derive a power signal corresponding with the level of power exhibited by said electrical cutting energy input; and said control assembly is responsive to derive a said relay control input terminating said conveyance of said link output when said power signal exceeds a power threshold level.

58. The electrosurgical generator of claim 56 wherein
said control assembly is responsive to derive a said relay control input terminating said conveyance of said link output when said high voltage monitor signal exceeds a high voltage threshold level.

59. The electrosurgical generator of claim 56 wherein
said control assembly is responsive to derive a said relay control input terminating said conveyance of said link output when said high voltage current monitor signal exceeds a current threshold level.

60. The electrosurgical generator of claim 56 comprising:
a link voltage monitor responsive to said rectifier network link output to derive a link monitor signal corresponding with said link output d.c. voltage level; and
said control assembly is responsive to derive a said relay control input terminating said conveyance of said link output when said link monitor signal corresponds with a said link output d.c. voltage level which exceeds a link over-voltage threshold level.

61. The electrosurgical generator of claim 60 in which said control assembly is responsive to derive said relay control input terminating said conveyance of said link output when said link monitor signal corresponds with a said link output d.c. voltage level which is below a predetermined under-voltage threshold level.

62. The system of claim 41 wherein
said first inverter control network comprises:
a comparator network responsive to a predetermined electrosurgical cutting voltage level and to said high voltage monitor signal to derive a program signal; and
a controller network responsive to said program signal to derive said first inverter control input.

63. The system of claim 62 in which said controller network is configured derive said first inverter control input as a slowly applied said program signal.

64. The system of claim 63 in which said first inverter control network comprises:
a link voltage monitor responsive to said link output to provide a link voltage controlling feedback signal; and
said controller network is further responsive to said link voltage controlling feedback signal to derive said first inverter control input.

* * * * *